US005536839A

United States Patent [19]

Cross et al.

[11] Patent Number: 5,536,839

[45] Date of Patent: Jul. 16, 1996

[54] (2-IMIDAZOLIN-2-YL) FUSED HETEROPYRIDINE COMPOUNDS

[75] Inventors: Barrington Cross, Rocky Hill; Marinus Los, Pennington; Robert F. Doehner, Jr., East Windsor; David W. Ladner, Hamilton Square; Jerry L. Johnson, Lawrenceville, all of N.J.

[73] Assignee: American Cyanamid Company, Madison, N.J.

[21] Appl. No.: 460,448

[22] Filed: Jun. 2, 1995

Related U.S. Application Data

[62] Division of Ser. No. 123,827, Sep. 20, 1993, which is a division of Ser. No. 465,569, Jan. 16, 1990, Pat. No. 5,252,538, which is a continuation of Ser. No. 178,408, Apr. 6, 1988, abandoned, which is a continuation of Ser. No. 876,599, Jun. 20, 1986, abandoned, which is a continuation-in-part of Ser. No. 808,578, Dec. 13, 1985, abandoned, and Ser. No. 612,531, May 21, 1984.

[51] Int. Cl.[6] .................. A01N 43/90; C07D 471/04; C07D 491/04; C07D 513/04

[52] U.S. Cl. .................. 546/113; 546/114; 546/115; 546/116; 546/117; 546/118; 546/120; 504/246

[58] Field of Search .................. 504/246; 546/113, 546/114, 115, 116, 117, 118, 120

[56] References Cited

U.S. PATENT DOCUMENTS

| | | | |
|---|---|---|---|
| 3,336,326 | 8/1967 | Godefroi et al. | 546/123 |
| 4,170,462 | 10/1979 | O'Neal et al. | 546/123 |
| 4,188,487 | 2/1980 | Los | 546/116 |
| 4,297,128 | 10/1981 | Los | 546/115 |
| 4,404,012 | 9/1983 | Orwick et al. | 546/123 |
| 4,459,409 | 7/1984 | Ladner | 546/115 |
| 4,608,079 | 8/1986 | Los | 546/116 |
| 4,638,068 | 1/1987 | Los | 546/116 |
| 4,656,283 | 4/1987 | Doehner | 546/170 |
| 4,696,694 | 9/1987 | Numata | 546/115 |
| 4,701,208 | 10/1987 | Los | 71/92 |
| 4,752,323 | 6/1988 | Los et al. | 71/90 |

FOREIGN PATENT DOCUMENTS

| | | | |
|---|---|---|---|
| 198522A | 10/1986 | European Pat. Off. | 546/123 |
| 0259687 | 8/1987 | European Pat. Off. | |
| 245860A | 11/1987 | European Pat. Off. | 546/123 |
| 3601688 | 7/1987 | Germany | 546/123 |
| 78-69835 | 6/1978 | Japan | |
| 62-230782A | 10/1987 | Japan | 546/116 |

OTHER PUBLICATIONS

M. J. Weiss, J. Amer. Chem. Soc., 79, 1266 (1957).
D. Baker et al., Synthesis, 1978, 478–9.
Hirsch & Wang, Syn. Comm. 12, 333 (1982).
O. Meth-Cohn, J. Chem. Soc., Park, I, 1537–43 (1981).
E. Bottorff, J. Am. Chem. Soc 73, 4380 (1951).
J. I. DeGraw, J. Het. Chem. 19, 1461 (1982).
R. Jones, J. Am. Chem. Soc. 73, 3684 (1951).
Nelson, et al. J. Pharm. Sci., 59, 1676 (1970).
D. N. Reinhoudt, Recueil, 92, 865 (1973).
S. K. Brownstein, J. Org. Chem., 23, 113 (1958).
Abstract of JP6 3295–575–A (1988).
Abstract of JP6 1109–790 (1986).
Abstract of JP6 3170–373–A (1988).
D. J. Brien et al.., J. Chem. Soc., Chem Comm., 1982 pp. 133–134.
R. Grigg et al., Tet. Lett., 23, pp. 2691–2692 (1982).
R. Jones, J. Am. Chem. Soc., 73, pp. 5244–5246 (1951).
T. Kurihara et al., Heterocycles, 6, pp. 547–550 (1977).
T. Kurihara et al., Chem. Pharm. Bull., 28, pp. 2972–2979 (1980).
Abstract of British Patent No. 721,295 (1955).
Schroder, et al. Eur. J. Med. Chem. Chim. Ther. 1979, 14(4), 309–15.
Klingsberg, E., "Pyridine and its Derivatives Part I" (1960).
M. Los., Abstract with structures of EPO 41623, May/1981.
H. Amschler, et al., Abstract with structures of DE32459950, Dec./1981.
F. Arndt, et al., Abstract with structures of DE3616849, May/1986.
A. F. Hawkins, et al., Abstract with structures of GB 2099421A, May/1981.
P. Caluwe, Tetrahedron 36, 2359 (1980).
O. Meth-Cohn, J. Chem. Soc., Perkin I, 2509 (1981).
G. Seitz and S. Dietrich, Arch. Pharm., 317, 379 (1984).
H. E. Foster and J. Hurst, J. Chem. Soc. Perkin 1, 507 (1976).
T. G. Majewica and P. Caluwe, Jr. Org. Chem. 39, 720 (1974).
Chem. Pharm. Bull. 27, 2861 (1979).
Hellberg, L. H., Juaarez, A., Tet. Lett., 3553 (1974).
Verhoeven et al., Tet. Lett., 207–210 (1977).

*Primary Examiner*—Robert W. Ramsuer
*Assistant Examiner*—Laura R. Cross
*Attorney, Agent, or Firm*—John W. Hogan, Jr.

[57] ABSTRACT

There are provided novel (2-imidazolin-2-yl) fused hetero-pyridine compounds, and intermediate compounds for the preparation thereof, and a method for controlling a wide variety of annual and perennial plant species therewith.

4 Claims, No Drawings

(2-IMIDAZOLIN-2-YL) FUSED HETEROPYRIDINE COMPOUNDS

This is a divisional of copending application Ser. No. 08/123,827 filed on Sept. 20, 1993, which is a divisional of application Ser. No. 07/465,569 filed Jan. 16, 1990, now U.S. Pat. 5,252,538, which is a continuation of U.S. Ser. 07/178,408 filed Apr. 6, 1988, now abandoned, which is a continuation of U.S. Ser. No. 06/876,599 filed Jun. 20, 1986, now abandoned, which is a continuation-in-part of U.S. Ser. No. 06/808,578 filed Dec. 13, 1985, now abandoned and U.S. Ser. No. 612,531 filed May 21, 1984.

BACKGROUND OF THE INVENTION

Novel herbicidal imidazolinyl benzoic acids, esters and salts, their preparation and use are disclosed in U.S. Pat. No. 4,188,487, and U.S. Pat. No. 4,297,128 and pending application for U.S. patent application Ser. Nos. 579,224, 631, 283 and 629,296, while various novel pyridine and quinoline imidazolinone compounds are described in pending applications for U.S. patent application Ser. Nos. 382,041 and 616,747. Pending Application for U.S. patent application Ser. No. 676,133, filed Nov. 29, 1984, describes herbicidal (2-imidazolin-2-yl)-thieno-and furo[2,3-b] and (3,2-b]pyridines, their preparation and use.

It is an object of this invention to provide the novel herbicidal (2-imidazol in-2-yl) fused heteropyridine compounds of the general formula:

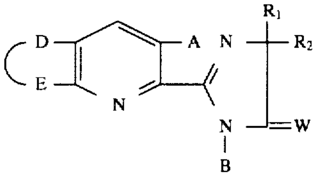

wherein D–E together with the two aromatic carbon atoms to which they are joined, represents a five or six membered ring containing from one to three heteroatoms, which may contain a variety of substituents: a method for their preparation; and the use of said compounds for controlling a wide variety of annual and perennial plant species therewith.

SUMMARY OF THE INVENTION

The invention is novel herbicidal (2-imidazolin-2-yl) fused heteropyridine compounds having the structures I to XXIV below

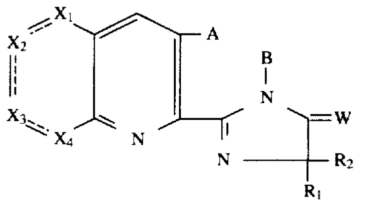

(I)

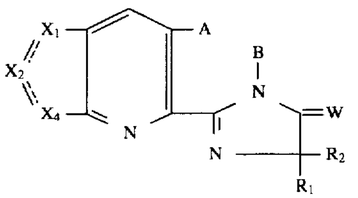

(II)

-continued

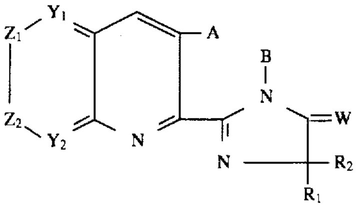

(III)

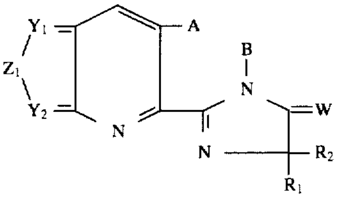

(IV)

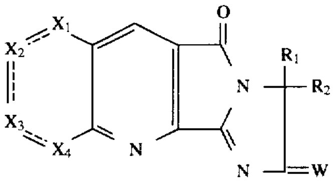

(V)

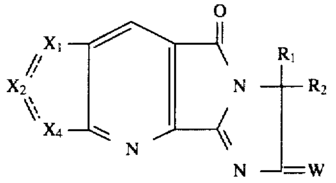

(VI)

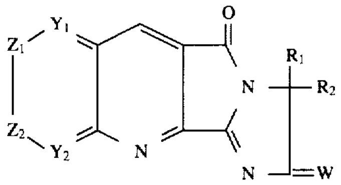

(VII)

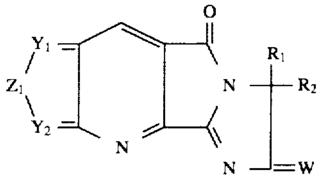

(VIII)

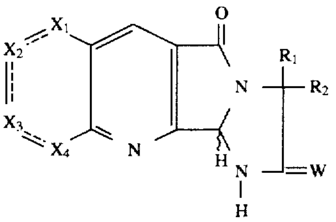

(IX)

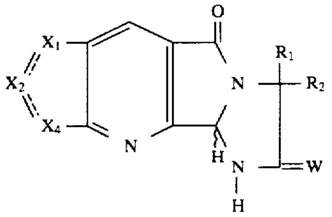

(X)

-continued
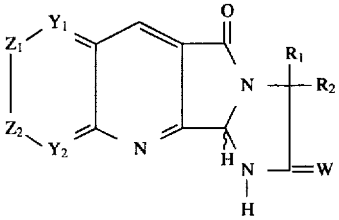
(XI)
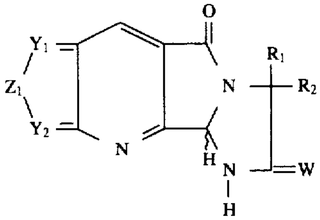
(XII)
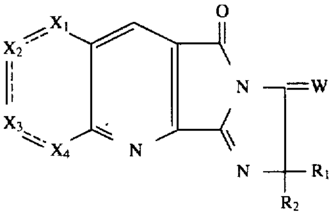
(XIII)
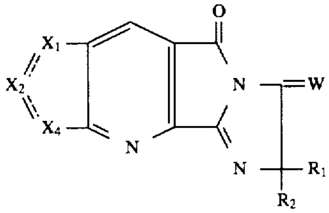
(XIV)
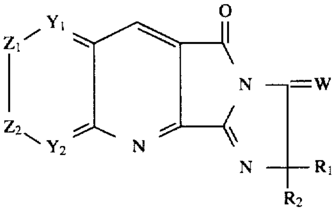
(XV)
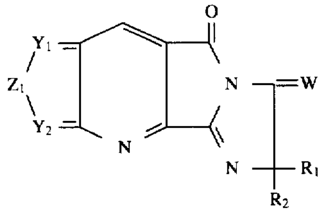
(XVI)
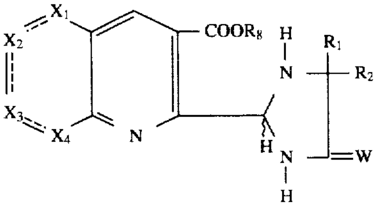
(XVII)
-continued
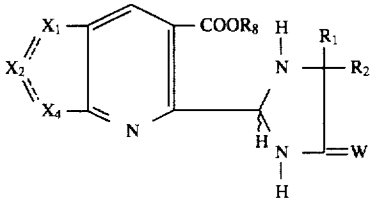
(XVIII)
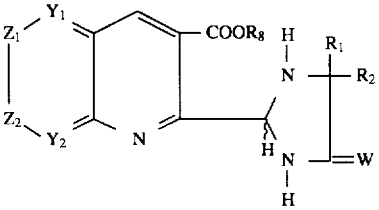
(XIX)
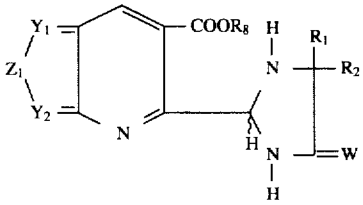
(XX)
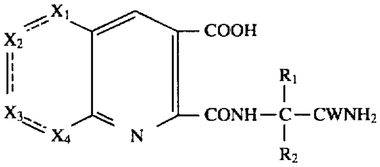
(XXI)
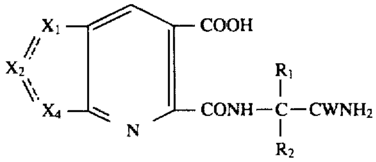
(XXII)
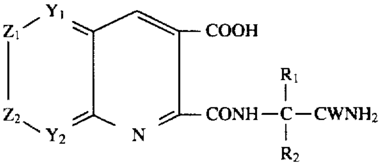
(XXIII)
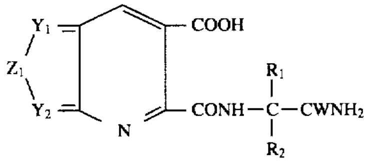
(XXIV)
wherein A is $COOR_8$, CHO, $CH_2OH$, $COCO_2OH$, $CONH_2$, $CH_2CO_2OH$, CONHOH or
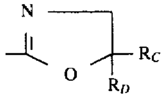
$R_C$ and $R_D$ are each hydrogen or $C_1$–$C_4$ alkyl;

$R_8$ is hydrogen, $C_1$–$C_4$ alkyl, which may be interrupted by O or S, or is optionally substituted with $C_1$–$C_4$ alkoxy, halogen, hydroxy, $C_3$–$C_6$ cycloalkyl, benzyloxy, furyl, phenyl, furfuryl, halophenyl, $C_1$–$C_4$ alkylphenyl, $C_1$–$C_4$ alkoxyphenyl, nitrophenyl, carboxyl, $C_1$–$C_4$ alkoxycarbonyl, cyano or $C_1$–$C_4$ trialkylammonium; $C_3$–$C_6$ alkenyl, optionally substituted with one or two $C_1$–$C_3$ alkoxy, phenyl or halogen groups; $C_3$–$C_6$ cycloalkyl, optionally substituted with one or two $C_1$–$C_3$ alkyl groups; $C_3$–$C_{10}$ alkynyl, optionally substituted with phenyl, halogen, loweralkoxy; or a cation;

B is H, $COR_9$ or $SO_2$ $R_{10}$, $R_9$ is $C_1$–$C_{11}$ alkyl, chloromethyl, $C_1$–$C_4$ loweralkoxyl or phenyl optionally substituted with one chloro, one nitro, one methyl, or one methoxy group; $R_{10}$ is $C_1$–$C_5$ alkyl, phenyl, or phenyl optionally substituted with one methyl, halogen, nitro, or $C_1$–$C_4$ alkoxy;

$R_1$ is $C_1$–$C_4$ alkyl;

$R_2$ is $C_1$–$C_4$ alkyl or $C_3$–$C_6$ cycloalkyl; and when taken together with the carbon to which they are attached, $R_1$ and $R_2$ may represent $C_3$–$C_6$ cycloalkyl, optionally substituted with methyl;

—represents a single or double bond;

W is O or S;

$X_1$, $X_2$, $X_3$ and $X_4$ are any combination of from zero to three $CR_4$ or $CR_5R_6$; from zero to three N or $NR_3$ and from zero to two O or S; $Y_1$ and $Y_2$ are N or $CR_4$ and are the same or different; $Z_1$ and $Z_2$ are O, S, $NR_3$ or $CR_5R_6$, and are the same or different, with the proviso that at least one of $X_{1-4}$, $Y_{1-2}$, or $Z_{1-2}$ is a heteroatom in each of Structure I–XXIV compounds;

$R_3$ is $C_1$–$C_4$ alkyl, which may be optionally substituted with phenyl or one or more halogens; $C_3$–$C_6$ alkenyl, optionally substituted with phenyl or one or more halogens; $C_3$–$C_6$ alkynyl, optionally substituted with phenyl or halogen; $C_1$–$C_4$ alkoxy, optionally substituted with phenyl or one or more halogens; $C_3$–$C_6$ alkenyloxy, optionally substituted with phenyl or one or more halogens; $C_3$–$C_6$ alkynyloxy optionally substituted with halogen or phenyl or $C_2$–$C_6$ alkanoyloxy, optionally substituted with halogen or phenyl;

$R_4$ is hydrogen, halogen, $C_1$–$C_6$ alkyl; $C_1$–$C_4$ alkoxy; $C_2$–$C_6$ alkanoyloxy; $C_1$–$C_4$ alkylthio; phenoxy; $C_1$–$C_4$ haloalkyl; $C_1$–$C_4$ haloalkoxy; nitro, $C_1$–$C_4$ alkoxycarbonyl; $C_1$–$C_4$ dialkylamino; $C_1$–$C_4$ alkylsulfonyl or phenyl, optionally substituted with one or two $C_1$–$C_4$ alkyl, $C_1$–$C_4$ alkoxy, halogen or haloalkyl;

$R_5$ and $R_6$ are each hydrogen, $C_1$–$C_4$ alkyl; $C_1$–$C_4$ alkoxy, $C_1$–$C_4$ haloalkoxy; nitro, $C_1$–$C_4$ alkylsulfonyl or phenyl optionally substituted with one or two $C_1$–$C_4$ alkyl, $C_1$–$C_4$ alkoxy, halogen or haloalkyl: or any combination of these groups except when $R_5$ and $R_6$ are the same group, they are either both hydrogen or both $C_1$–$C_4$ alkyl; and when taken together, $R_5$ and $R_6$ may form a ring in which $R_5R_6$ are represented by the structure $—(CH_2)_n—$ where n is an integer of 4 or 5, or when taken together, $R_5$ and $R_6$ may form a group =O or $—NR_7$ wherein $R_7$ is phenyl, $C_1$–$C_4$ alkyl, $C_1$–$C_4$ alkoxy or $C_1$–$C_4$ alkylamino;

$R_3$, $R_4$, $R_5$ or $R_6$ when present on adjacent positions may, along with the atoms to which they are attached, form a ring and such $R_3$–$R_6$ pairs can be represented by the structure $—(CH_2)_m—$ or $—(CH)_m—$ where m is an integer of 3 or 4;

with the provisos that in structures II, VI, X, XIV, XVIII and XXII, when $X_1$ is O or S, at least one of $X_2$ and $X_4$ may not be $CR_4$ or $CR_5R_6$; when $X_4$ is O or S, at least one of $X_1$ and $X_2$ may not be $CR_4$ or $CR_5R_6$; in structures IV, VIII, XII, XVI, XX and XXIV when $Z_1$ is O, $Y_1$ and $Y_2$ may not be $CR_4$;

—represents a single bond between:

$X_1$ and $X_2$ when either $X_1$ or $X_2$ is S, O, $NR_3$ or $CR_5R_6$;

$X_2$ and $X_3$ in structures I, V, IX, XIII, XVII and XXI, when either $X_2$ or $X_3$ is O, S, $NR_3$ or $CR_5R_6$;

$X_3$ and $X_4$ in structures I, V, IX, XIII, XVII and XXI, when either $X_3$ or $X_4$ is O, S, $NR_3$ or $CR_5R_6$;

$X_2$ and $X_4$ in structures II, VI, X, XIV, XVIII and XXII. when either $X_2$ or $X_4$ is O, S, $NR_3$ or $CR_5R_6$;

when one of $X_{1-4}$ is oxygen, the $X_{1-4}$ to which it is attached is N, $NR_3$, $CR_4$ or $CR_5R_6$;

and in structures III, VII, XI, XV, XIX and XXIII, when one of $Z_{1-2}$ is oxygen, the $Z_{1-2}$ to which it is attached is $NR_3$ or $CR_5R_4$;

when B is $COR_9$ or $SO_2$ $R_{10}$ and $R_8$ is hydrogen, then — represents an aromatic bond, $R_3$ is $C_1$–$C_4$ alkyl and $R_4$, $R_5$ and $R_6$ may not be halogen.

Structure I–XXIV compounds also include tautomers thereof, agriculturally acceptable acid addition salts and other addition compounds thereof, the N-oxides thereof when A is COORS; and when $R_1$ and $R_2$ are not the same, the optical isomers thereof.

This invention also includes novel herbicidal compounds of the formula

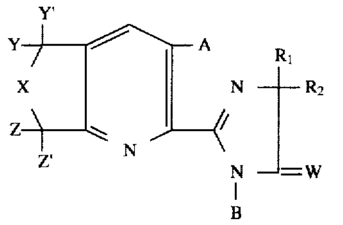

XXXVII or

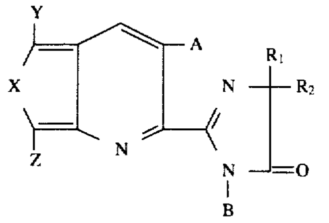

XXXVIII wherein $R_1$ is $C_1$–$C_4$ alkyl; $R_2$ is $C_1$–$C_4$ alkyl or $C_3$–$C_6$, cycloalkyl; and when $R_1$ and $R_2$ are taken together with the carbon to which they are attached they may represent $C_3$–$C_6$ cycloalkyl optionally substituted with methyl; A is $COOR_8$, CHO, $CH_2OH$, $COCO_2OH$, $CONHCH_2OH$, CONHOH, or

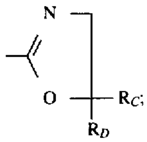

$R_8$ is hydrogen, $C_1$–$C_{12}$ alkyl optionally substituted with one of the following groups: $C_1$–$C_3$ alkoxy, halogen, hydroxy, $C_3$–$C_6$ cycloalkyl, benzyloxy, furyl, phenyl, furfuryl, halophenyl, loweralkylphenyl, loweralkoxyphenyl, nitrophenyl, carboxyl, loweralkoxycarbonyl, cyano, $C_1$–$C_4$ alkylthio or triloweralkylammonium, in addition the alkyl chain may be interrupted by one or more O or S; $C_3$–$C_6$ alkenyl optionally substituted with one of the following groups: $C_1$–$C_3$ alkoxy, phenyl, halogen or with two $C_1$–$C_3$ alkoxy groups or two halogen groups: $C_3$–$C_6$ cycloalkyl optionally substituted with one or two $C_1$–$C_3$ alkyl groups; $C_3$–$C_{10}$ alkynyl optionally substituted with phenyl, halogen or $CH_2OH$; or a cation selected from the group consisting of alkali metals, alkaline earth metals, (Ca, Ba) and manganese.

copper, iron, ammonium and organic ammonium; $R_C$ and $R_D$ are H, or $CH_3$; B is H, $COR_9$ or $SO_2R_{10}$, provided that when B is $COR_9$ or $SO_2R_{12}$, and A is $COOR_8$, $R_8$ cannot be hydrogen or a salt-forming cation; $R_{11}$ is $C_1$–$C_{11}$ alkyl, chloromethyl or phenyl optionally substituted with one chloro, one nitro, one methyl, or one methoxy group; $R_{10}$ is $C_1$–$C_5$ alkyl or phenyl optionally substituted with one methyl group, chloro or nitro; W is O or S; X is O, S, or —S=O; Y and Y', Z and Z' are hydrogen, halogen, $C_1$–$C_6$ alkyl, $C_1$–$C_4$ hydroxyloweralkyl, $C_1$–$C_6$ alkoxy, $C_1$–$C_6$ acyloxy, benzoyloxy optionally substituted with one or two $C_1$–$C_4$ alkyl, $C_1$–$C_4$ alkoxy, halogen; $C_1$–$C_4$ alkylthio, phenoxy, $C_1$–$C_4$ haloalkyl, $C_1$–$C_4$ haloalkoxy, nitro, cyano, $C_1$–$C_4$ alkylamino, $C_1$–$C_4$ dialkylamino, $C_1$–$C_4$ alkylsulfonyl or phenyl optionally substituted with one or two $C_1$–$C_4$ alkyl, $C_1$–$C_4$ alkoxy, halogen, or any combination of two of these groups and wherein Y and Z are the same group provided that Y and Z are H, halogen, alkyl or alkoxy, and when Y and Y' or Z and Z' are the same group they are hydrogen or alkyl: and the pyridine N-oxides thereof, when W is O or S and A is $COOR_8$; and when $R_1$ and $R_2$ are not the same, the optical isomers thereof, and, except when $R_8$ is a salt-forming cation, the acid addition salts thereof.

Ring systems formed by $X_{1-4}$, $Z_{1-2}$ and $Y_{1-2}$ and encompassed by this invention include six-membered rings containing:

one heteroatom, where one of $X_{1-4}$, $Y_{1-2}$ or $Z_{1-2}$ is O, S, N, or $NR_3$. Examples of these are pyrano-. thiopyrano-, tetrahydropyrido-, pyrido-, dihydropyrano-. dibydropyrido-, and dibydrotbiopyrano-pyridines.

two heteroatoms, where two of $X_{1-4}$, $Y_{1-2}$ and $Z_{1-2}$ are O, S, N or $NR_3$, examples of which are dioxino-, dithiino-, oxazino-, oxathiino, pyrazino-, thiazino-, pyridazino-and pyrimidino-pyridines; and the di- and tetrahydro derivatives of these ring systems;

three heteroatoms, where three of $X_{1-4}$, $Y_{1-2}$ and $Z_{1-2}$ are N or $NR_3$. Examples of these are triazino-, dihydrotriazino- and tetrahydrotriazino-pyridines.

Five-membered ring systems include five-membered rings containing:

one heteroatom, where one of $X_{1-4}$, $Y_{1-2}$ or $Z_{1-2}$ is N or $NR_3$, such as the pyrrolopyridines and the dihydropyrrolopyridines;

two heteroatoms, where two of $X_{1-4}$, $Y_{1-2}$ and $Z_{1-2}$ are each O, S, N or $NR_3$ such as dioxolo-, dithiolo-. imidazo, imidazolino-, pyrazolo-, pyrazolino-, oxazolo-. oxazolino-, isoxazolo-, isoxazolino-, thiazolo-, thiazolino-, isothiazolo-, isotbiazolino-, and oxathiolo-pyridines;

three heteroatoms where three of $X_{1-4}$, $Y_{1-2}$ and $Z_{1-2}$ are N, $NR_3$, O or S such as thiadiazolo-, thiadiazolino-, oxadiazolo-, oxadiazolino-, triazolino- or triazolopyridines.

Preferred heteropyridine ring systems of structure I—XXIV compounds are pyranopyridines, pyrrolopyridines, pyrazolopyridines, imidazopyridines, oxazolopyridines, isoxazolopyridines, dithiolopyridines, dioxolopyridines, dioxinopyridines, dithiinopyridines, pyridopyridines (naphthyridines) , thinoyranopyridines, oxazinopyridines, oxathiinopyridines and thiazinopyridines; and the dihydro and tetrahydro derivatives of these ring systems:

wherein $R_1$ is methyl or ethyl, $R_2$ is ethyl, propyl or isopropyl, and when $R_1$ and $R_2$ are taken together, they represent a cyclohexyl ring, optionally substituted with methyl; $R_3$ is $C_1$–$C_3$ alkyl, $C_1$–$C_4$ alkoxy, allyloxy, $CF_3O$—, $CF_2HO$— or $CF_3$;

$R_4R_5$ and $R_6$ are each hydrogen, chlorine, bromine, $C_1$–$C_3$ alkyl, $C_1$–$C_3$ alkoxy, $C_1$–$C_3$ alkylthio, $C_1$–$C_2$ dialkylamino, or when $R_5$ and $R_4$ are taken together form the doubly bonded oxygen of a carbonyl group;

A is $COOR_8$ where $R_8$ is H, $C_1$–$C_4$ alkyl, which may be interrupted by O or S and is optionally substituted with furyl, propynyl, phenyl or halophenyl; $C_1$–$C_4$ alkylphenyl, $C_1$–$C_4$ alkoxyphenyl or nitrophenyl, or a cation;

B is H, acetyl, $C_1$–$C_4$ alkylsulfonyl or phenylsulfonyl optionally substituted with $C_1$–$C_4$ loweralkyl, nitro, chloro or $C_1$–$C_4$ loweralkoxy; W is O or S.

A more preferred group of structures are those of I–XXIV where only one or two of $X_{1-4}$, $Y_{1-2}$ and $Z_{1-2}$ are each O, S, N, or $NR_3$;

A is $COOR_8$ where $R_8$ is hydrogen, methyl, ethyl, methoxyethyl, ethoxyethyl, methylthiomethyl, methylthioethyl, propargyl, phenyl-substituted alkyl, furfuryl, or a sodium, calcium, lithium, potassium, magnesium, ammonium, or organic ammonium cation;

B is H, benzoyl acetyl, methanesulfonyl or p-toluenesulfonyl;

$R_1$ is methyl and $R_2$ is isopropyl;

$R_3$ is methyl, ethyl, methoxy, ethoxy and allyloxy;

$R_4$, $R_5$ and $R_6$ are each methyl, ethyl, chloro, bromo, hydrogen, methoxy and ethoxyl, or $R_5R_6$, when taken together are =O;

and W is O.

A more preferred group of structures are those of formula I-XXIV in which the heterocyclic rings are pyrano-, thiopyrano, dioxino, pyrrolo, pyrazolo, and dioxolopyridines.

wherein $R_1$ is methyl, $R_2$ is isopropyl, $R_3$ is $CH_3$ or $OCH_3$, B is hydrogen, W is oxygen, A is COOH and the agriculturally acceptable salts and esters of these acids.

A most preferred group of structures are those of formula I–IV in which the heterocyclic rings are pyrano-, thiopyrano, dioxino, pyrrolo, pyrazolo and dioxolopyridines wherein $R_1$ is methyl, $R_2$ is isopropyl, $R_3$ is $CH_3$ or $OCH_3$, B is hydrogen, W is oxygen, A is COOH and the agriculturally acceptable salts and esters of these acids.

In formulas I to IV and XVIII to XX above, preferred cations include alkali metals such as: sodium, potassium and lithium, but sodium is generally preferred: or organic ammonium which is defined as a group consisting of a positively charged nitrogen atom joined to from one to four aliphatic groups, each containing from one to 20 carbon atoms. Among the organic ammonium groups which are illustrative for the preparation of the aliphatic ammonium salt of the formulas I to IV and XVIII to XX—imidazolinyl fused heteropyridine acids herein are: monoalkylammonium, dialkylammonium, trialkylammonium, tetraalkylammonium, monoalkenylammonium, dialkenylammonium, trialkenylammonium, monoalkynylammonium, dialkynylammonium, trialkynylammonium, monoalkanolammonium, dialkanolammonium, trialkanolammonium, $C_5$–$C_6$-cycloalkylammonium, piperidinium, morpholinium, pyrrolidinium, benzylammonium and equivalents thereof.

In general, and for convenience, the compounds of the invention may be represented by structures XXV–XXX below

XXV

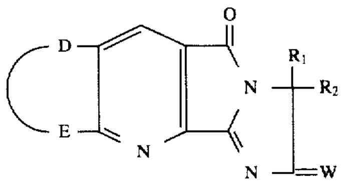

-continued

XXVI

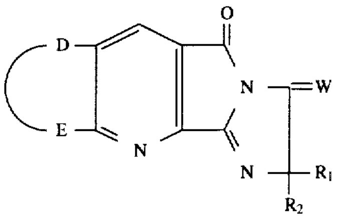

XXVII

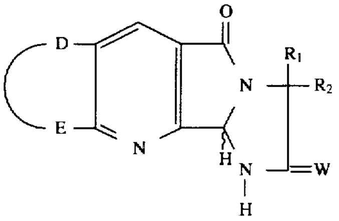

XXVIII

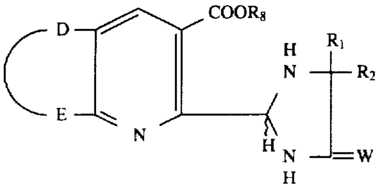

XXIX

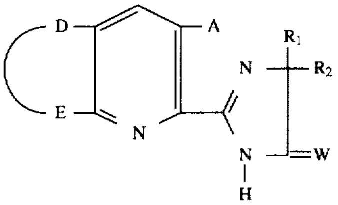

XXX

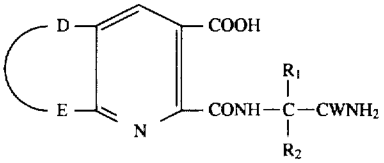

wherein D–E together with the two aromatic carbons to which they are joined, represents a five or six membered ring as described in formulas I to XXIV above.

The compounds of the present invention may conveniently be prepared from the appropriately substituted fused heteropyridinedicarboxylic acids and esters, which may be represented in general by the formula

XXXI

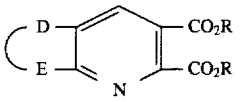

wherein D–E forms part of a five-or six-membered ring as previously described for formulas I-XXIV above.

Thus, diesters of the above general formula XXXI may be hydrolyzed to the corresponding heteropyridine-2,3-carboxylic acids of formula XXXIa and by reaction thereof with a strong base such as potassium hydroxide or sodium hydroxide. Acid anhydrides of formula XXXII may then be prepared by treatment of the formula XXXIa heteropyridinedicarboxylic acids with, for example, acetic anhydride. Reaction of formula XXXII anhydrides with an appropriately substituted aminocarboxamide or aminothiocarboxamide depicted by formula XXXIII yields carbamoyl heteropyridine acids of formula XXX. Treatment of the thus-formed formula XXX carbamoyl heteropyridine acids with about two to ten molar equivalents of aqueous or aqueous alcoholic sodium or potassium hydroxide, preferably under a blanket of inert gas such as nitrogen, cooling and acidifying to pH 2 to $_4$ with a strong mineral acid such as hydrochloric acid or sulfuric acid gives herbicidally effective formula XXIXa (4,4-disubstituted-5-oxo-(or thioxo)-2-imidazolin-2-yl) fused heteropyridine nicotinic acids, as illustrated in Flow Diagram I below.

FLOW DIAGRAM I

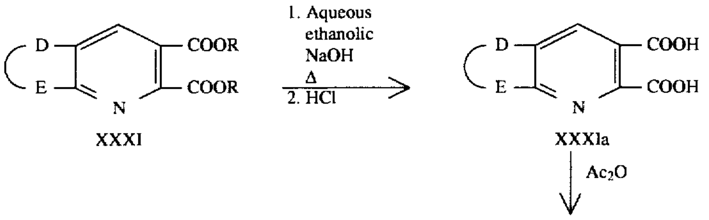

XXXI XXXIa

-continued

FLOW DIAGRAM I

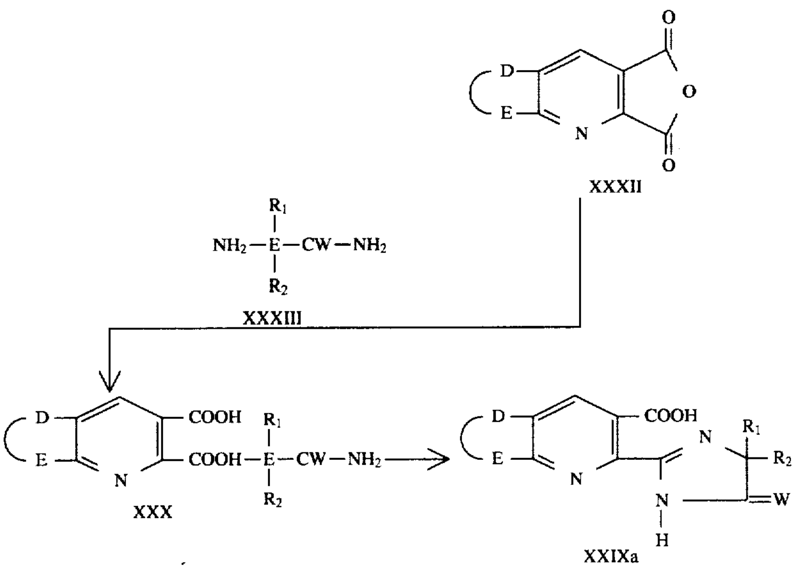

XXXII

XXXIII

XXX

XXIXa

General formula XXIXb (2-imidazolin-2-yl) fused heteropyridine esters, wherein $R_8$ represents a substituent other than hydrogen or a salt-forming cation, can be prepared by reacting a novel fused imidazopyrrolo-heteropyridinedione, represented by the general formula XXV or XXVI, hereinbelow, in Flow Diagram II, with an appropriate alcohol and corresponding alkali metal alkoxide at a temperature ranging between about 20° C. and about 50° C.

Formula XXVI novel fused imidazopyrroloheteropyridinediones may conveniently be prepared from formula XXIXa acids by treatment with one equivalent of dicyclohexylcarbodiimide in an inert solvent such as methylene chloride as illustrated in Flow Diagram II below.

Formula XXV imidazopyrroloheteropyridinediones may be prepared from formula XXIXa compounds by treatment with one to three equivalents of acetic anhydride in pyridine.

Treatment of formula XXIXb esters with an acylating agent such as acetyl chloride or acetic anhydride or a sulfonating agent such as p-toluenesulfonyl chloride in an inert solvent such as tetrahydrofuran gives the formula XXIXb esters where B is other than hydrogen as defined above. The compounds of formula XXIXd are prepared by selective cleavage of the benzyl esters of formula XXIXc with hydrogen and a palladium catalyst.

Reduction of formula XXIXb esters with, for instance, sodium cyanoborohydride, provides the dihydroimidazolinone esters of formula XXVIII which can be hydrolyzed in base to the corresponding acid compounds of formula XXVIIIa. An alternate synthesis of formula XXVIII compounds is by treatment of formula XXXIV compounds with about one equivalent of an amino amide compound of formula XXXII and a catalytic amount of p-toluenesulfonic acid in toluene, The ester aldehyde compounds of formula XXXIV may be prepared by reduction of the diesters with diisobutyl aluminum hydride, The acid compounds of formula XXVIIIa may be treated with acetic anhydride in pyridine to give the dihydro imidazopyrroloheteropyridine diones of formula XXVII.

FLOW DIAGRAM II

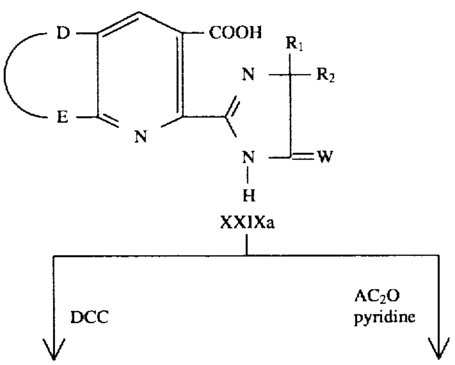

XXIXa

-continued
FLOW DIAGRAM II
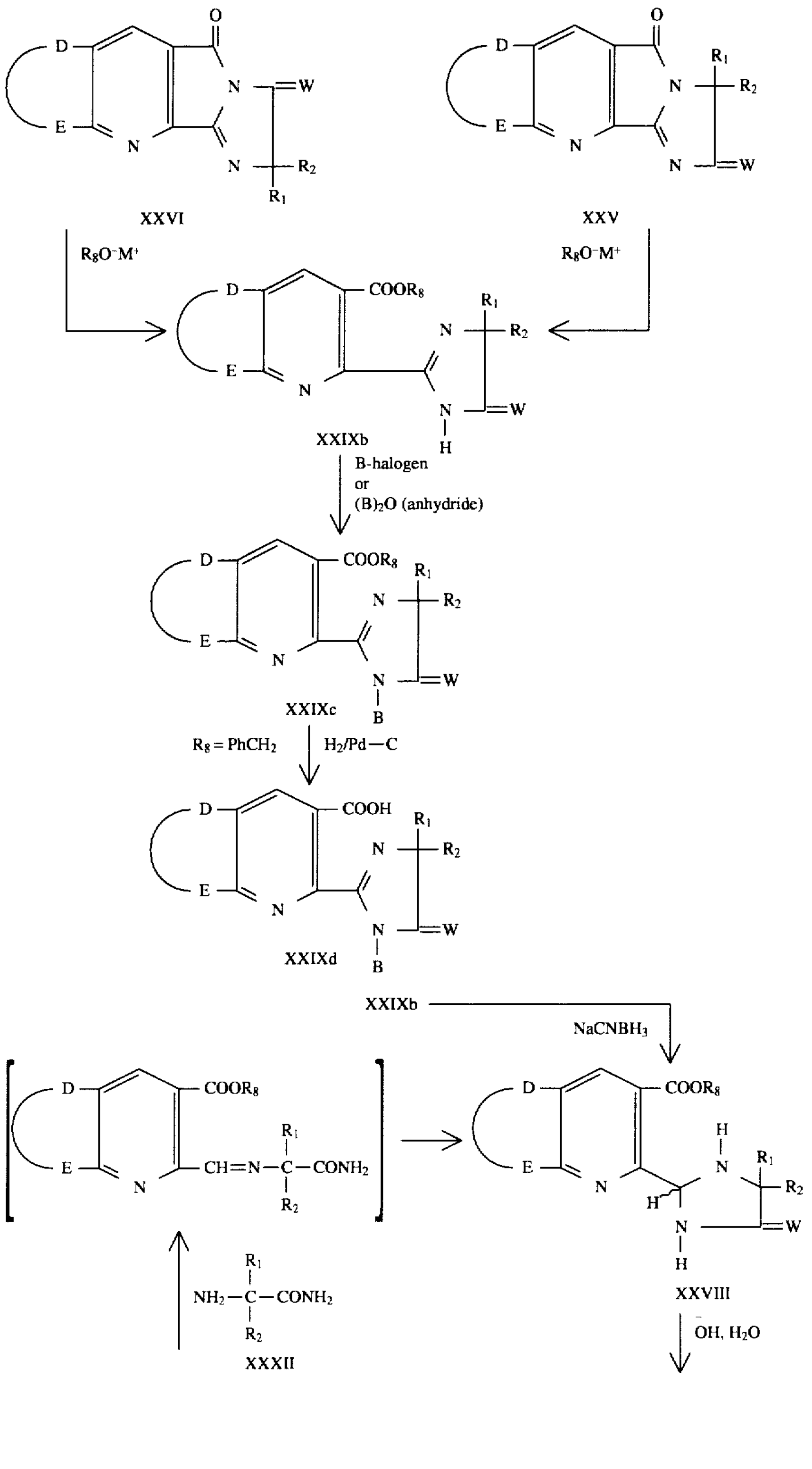

-continued

FLOW DIAGRAM II

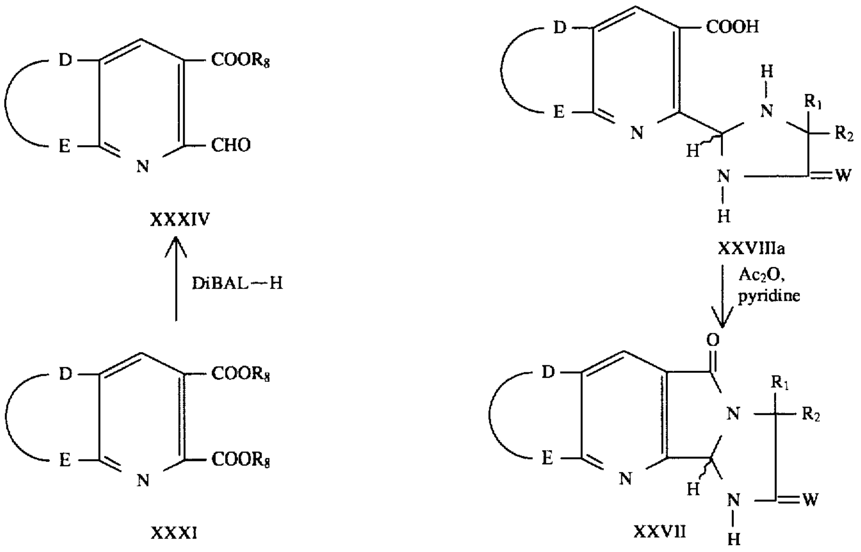

XXXIV XXVIIIa XXXI XXVII

Many heteropyridine diesters having the general formula XXXI above are either known in the art, or can be prepared by reacting an amino or enamino heterocycle with oxalacetic esters or acetylenedicarboxylate ester.

An amino-substituted heterocycle with at least one unsubstituted ortho carbon may be condensed with oxalacetic acid esters or added to acetylene dicarboxylic esters to give an intermediate enamine. This can then be treated with one or two equivalents of Viismeier reagent as described in pending application for U.S. Patent of R. Doehner, Ser. No. 698,192 filed Feb. 4, 1985 which is incorporated herein by reference thereto, to give the desired diester.

Certain o-amino-heterocyclic aldehydes may be reacted with DMAD or oxalacetic esters in a manner as described by P. Caluwe, Tetrahedron 36, 2359 (1980), to give the desired diesters directly.

A novel process of this invention is preparing 5-substituted, 6-substituted and 5,6-disubstituted pyridine-2,3-dicarboxylates from enamines, which may be prepared from heterocyclic rings containing a carbonyl functionality, by allowing them to react with an ethoxymethylene compound. The initial product is not isolated but is treated directly with an ammonia source, such as ammonium acetate, to give the diester, which is described more fully after Flow Diagram III below.

These reactions are illustrated in Flow Diagram III below, wherein D–E together with the carbons to which they are joined, represents a five- or six-membered heterocyclic ring; R is methyl or ethyl; R' is hydrogen or CHO: R" and R"' are each hydrogen, $C_1$–$C_6$ alkyl, or taken together with the nitrogen atom to which they are attached may form a five- or six-membered saturated ring containing a total of, at most, two hereto atoms.

FLOW DIAGRAM III

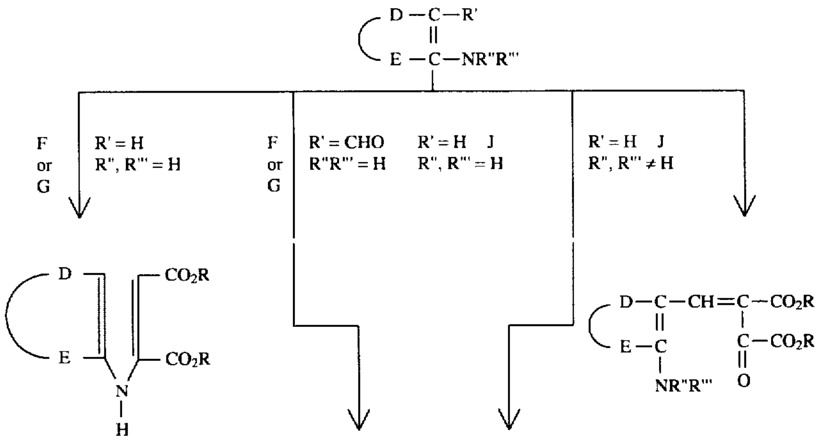

-continued

FLOW DIAGRAM III

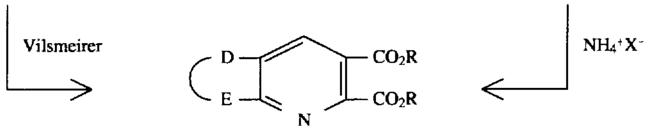

XXXI

F = 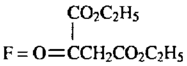

G = $CH_3O_2C—C≡C—CO_2CH_3$

J = 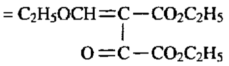

When R" and R'"≠H, the above novel enamine reaction is a method for the preparation of 5-substituted, 6-substituted and 5,6-disubstituted pyridine 2,3-dicarboxylates of formula XXXIb

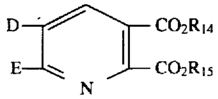

(XXXIb)

wherein E is hydrogen, $C_1$–$C_6$ alkyl or phenyl optionally substituted with methyl;

D is hydrogen, $C_1$–$C_6$ alkyl or phenyl optionally substituted with methyl or D and E taken together with the carbons to which they are attached may form a four to seven membered ring which may contain one oxygen or sulfur, which may be optionally substituted with a methyl group, comprising reacting an enamine of formula XXXIV

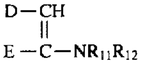

(XXXIV)

wherein each of $R_{11}$ and $R_{12}$ is $C_1$–$C_6$ alkyl, or taken together with the nitrogen atom to which they are attached $R_{11}$ and $R_{12}$ may form a five or six membered saturated ring containing at most two hetero atoms wherein E is hydrogen, $C_1$–$C_6$ alkyl, or phenyl optionally substituted with methyl;

D is hydrogen, $C_1$–$C_6$ alkyl, or phenyl optionally substituted with methyl or D and E taken together with the carbons to which they are attached may form a four to seven membered ring which may contain one oxygen or sulfur, which may be optionally substituted with a methyl group with an oxymethylene oxalacetate of formula XXXV

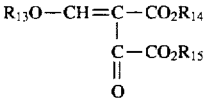

(XXXV)

wherein each of $R_{13}$, $R_{14}$ and $R_{15}$ is hydrogen or $C_1$–$C_4$ alkyl in an alcoholic, ketonic, halogenated hydrocarbon, hydrocarbon or aromatic solvent or acetonitrile from five minutes to 24 hours at a temperature of from −78° C. to 50° C., and reacting the thus-formed adduct with an ammonia source such as $NH_3$ or $NH_4X^-$;

wherein X is OH, carboxyl or halogen; in a solvent selected from alcohols, ether-alcohol mixtures, halogenated hydrocarbon-alcohol mixtures, halogenated hydrocarbon-water mixtures or acetic acid for from thirty minutes to 72 hours, at a temperature of from 0° C. to the boiling point of the solvent system, as illustrated in Flow Diagram IV below.

FLOW DIAGRAM IV

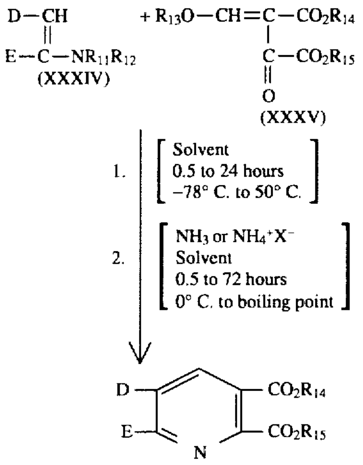

The resulting 5-substituted, 6-substituted and 5,6-disubstituted pyridine-2,3-dicarboxylates are useful intermediates for the preparation of herbicidal 2-(2-imidazolin-2-yl)pyridine and quinoline acids, esters and salts such as those disclosed in European Patent Application Number 81103638.3 filed Dec. 1, 1981, as illustrated in Flow Diagram V below.

FLOW DIAGRAM V

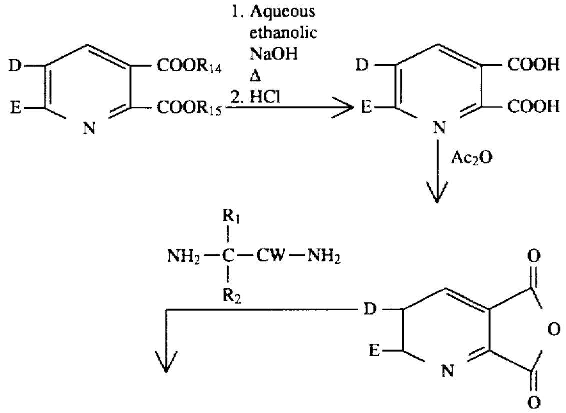

-continued

FLOW DIAGRAM V

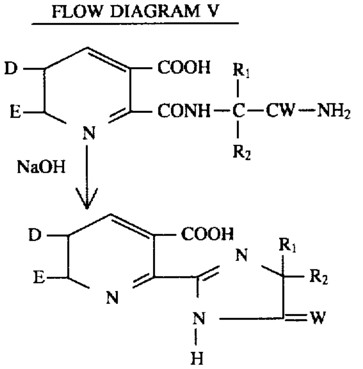

wherein $R_1$ is $C_1$–$C_4$ alkyl; $R_2$ is $C_1$–$C_4$ alkyl or $C_3$–$C_6$ cycloalkyl; and when $R_1$ and $R_2$ are taken together with the carbon to which they are attached they may represent $C_3$–$C_6$ cycloalkyl optionally substituted with methyl; W is O or S; and D and E are as defined for formula XXXIb above.

Additionally the method of the present invention provides a novel method for the preparation of 2,3-dihydrofuro[3,2-b]and dibydrothieno[3,2-b]pyridines described in pending Application for U.S. Letters Pat. Ser. No. 500,219, filed Jun. 2, 1983 of Marinus Los, David William Ladnet and Barrington Cross, by the reaction of diethylethoxymethylene oxalacetate with a mixture of enamines derived from 3-keto-tetrahydrofuran or 3-ketotetrahydrothiophene, followed by treatment with ammonia or ammonium salts, as illustrated in Flow Diagram VI below.

FLOW DIAGRAM VI

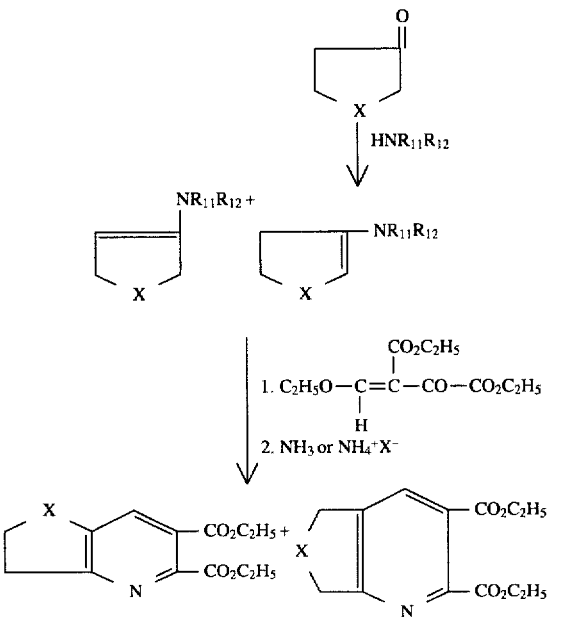

wherein X is O or S; and $R_{11}$ and $R_{12}$ are as previously described for formula XXXIV above.

Uniquely, as illustrated in Flow Diagram VI above the method of the present invention also provides a facile and novel method for the preparation of novel dihydrofuro[3,4-b] and dihydrothieno[3,4-b]pyridine 2,3-dicarboxylates of formula XXXVI

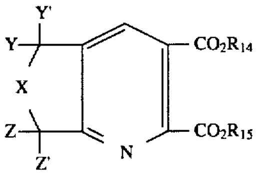

(XXXVI)

wherein $R_{14}$ and $R_{15}$ are as described for formula XXXV above; Y and Y' and Z and Z' are hydrogen, halogen, $C_1$–$C_6$ alkyl, $C_1$–$C_4$ hydroxyloweralkyl, $C_1$–$C_6$ alkoxy, $C_1$–$C_4$ alkylthio, phenoxy, $C_1$–$C_4$ haloalkyl, $C_1$–$C_4$ haloalkoxy, nitro, cyano, $C_1$–$C_4$ alkylamino, $C_1$–$C_4$ dialkylamino, $C_1$–$C_4$ alkylsulfonyl or phenyl optionally substituted with one or two $C_1$–$C_4$ alkyl, $C_1$–$C_4$ alkoxy, halogen, or any combination of two of these groups and wherein Y and Z are the same group provided that Y and Z are H, halogen, alkyl or alkoxy, and when Y and Y' or Z and Z' are the same group, they are hydrogen or alkyl.

The novel formula XXXVI compounds may in turn be converted by the procedure illustrated in Flow Diagram V to novel herbicidal 5,7-dihydro-2-(.2-imidazolin-2-yl)thieno and furo[3,4-b]pyridine compounds having the structure XXXVII

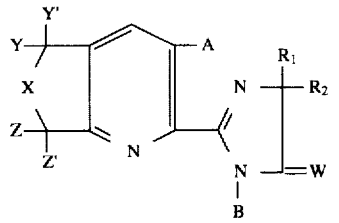

(XXXVII)

wherein $R_1$ is $C_1$–$C_4$ alkyl; $R_2$ is $C_1$–$C_4$ alkyl or $C_3$–$C_6$ cycloalkyl; and when $R_1$ and $R_2$ are taken together with the carbon to which they are attached they may represent $C_3$–$C_6$ cycloalkyl optionally substituted with methyl; A is $COOR_8$, CHO, $CO_2OH$, $COCO_2OH$, $CONHCH_2CO_2OH$, CONHOH, or

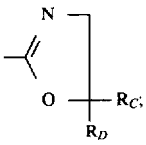

$R_8$ is hydrogen, $C_1$–$C_{12}$ alkyl optionally substituted with one of the following groups: $C_1$–$C_3$ alkoxy, halogen, hydroxy, $C_3$–$C_6$ cycloalkyl, benzyloxy, furyl, phenyl, furfuryl, halophenyl, loweralkylphenyl, loweralkoxyphenyl, nitrophenyl, carboxyl, loweralkoxycarbonyl, cyano, $C_1$–$C_4$ alkylthio or triloweralkylammonium, in addition the alkyl chain may be interrupted by one or more O or S; $C_3$–$C_6$ alkenyl optionally substituted with one of the following groups: $C_1$–$C_3$ alkoxy, phenyl, halogen or with two $C_1$–$C_3$ alkoxy groups or two halogen groups: $C_3$–$C_6$ cycloalkyl optionally substituted with one or two $C_1$–$C_3$ alkyl groups; $C_3$–$C_{10}$ alkynyl optionally substituted with phenyl, halogen or $CH_2OH$: or a cation selected from the group consisting of alkali metals, alkaline earth metals, (Ca, Ba) and manganese, copper, iron, ammonium and organic ammonium; $R_C$ and $R_D$ are H, or $CH_3$; B is H, $COR_9$ or $SO_2R_{10}$, provided that when B is $COR_9$ or $SO_2R_{10}$, and A is $COOR_8$, $R_8$ cannot be hydrogen or a salt-forming cation; $R_9$ is $C_1$–$C_{11}$ alkyl, chloromethyl or phenyl optionally substituted with one chloro, one nitro, one methyl, or one methoxy group; $R_{10}$ is $C_1$–$C_5$ alkyl or phenyl optionally substituted with one methyl group, chloro or nitro; W is O or S; X is O, S, or —S=O; Y and Y' Z and Z' are hydrogen, halogen, $C_1$–$C_6$ alkyl, $C_1$–$C_4$ hydroxyloweralkyl, $C_1$–$C_6$ alkoxy, $C_1$–$C_6$ acyloxy, benzoyloxy optionally substituted with one or two $C_1$–$C_4$ alkyl, $C_1$–$C_4$ alkoxy, halogen; $C_1$–$C_4$ alkylthio, phenoxy, $C_1$–$C_4$ haloalkyl, $C_1$–$C_4$ haloalkoxy, nitro, cyano, $C_1$–$C_4$ alkylamino., $C_1$–$C_4$ dialkylamino, $C_1$–$C_4$ alkylsulfonyl or phenyl optionally substituted with-one or two $C_1$–$C_4$ alkyl, $C_1$–$C_4$ alkoxy, halogen, or any combination of two of these groups and wherein Y and Z are the same group provided that Y and Z are H, halogen, alkyl or alkoxy, and when Y and Y' or Z and Z' are the same group they are hydrogen or alkyl; and the pyridine N-oxides thereof, when W is O or S and A is $COOR_8$; and when $R_1$ and $R_2$ are not the same, the optical isomers thereof, and, except when $R_8$ is a salt-forming cation, the acid addition salts thereof.

Oxidation of compounds of formula XXXVII when X is S yields novel thieno[3,4-b]pyridine 2,3-dicarboxylates which in a like manner to that described above and illustrated in Flow Diagram V above yields novel herbicidal 2-(2-imidazolin-2-yl)thieno[3,4-b]pyridine compounds of formula XXXVIIIb

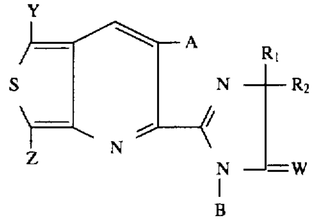

(XXXVIIIb)

wherein $R_1$, $R_2$, A, B, W, Y and Z are as described for formula XXXVI above.

The novel method of the present invention provides a means of preparing a wide variety of 5-substituted, 6-substituted and 5,6-disubstituted pyridine-2,3-dicarboxylates including the novel formula XXXIb thieno[3,4-b]and furo [3,4-b]pyridine 2,3-dicarboxylates described above.

Literature methods for preparing 5,6-dialkyl and 5,6-alkyl-arylpyridine-2,3-dicarboxylates are limited, often requiring oxidation of alkyl or aryl substituents at positions 2 and 3 in order to obtain diacids. R. Jones, J. Am. Chem. Soc. 73, 4380 (1951) describes a method in which reaction of a primary enamine yields 6-alkylpyridine-2,3-dicarboxylates which contain electron withdrawing substituents such as $COCH_3$, CN or $CO_2Et$ in the 5-position. This method cannot be used to prepare 5,6-dialkyl or alkylaryl pyridine-2,3-dicarboxylates because primary enamines without electron withdrawing substituents cannot readily be prepared, i.e., the reaction of ammonia with aliphatic ketones produces imines which do not tautomerize to enamines and, unless trapped in situ, polymerize. Other methods employing malononitriles such as those described in Japanese Patent 78 69,835 and that of 3. I. DeGraw, J. Het. Chem. 19, 1461 (1982), can yield 5, and 5,6-dialkylpyridines but not with the desired 2,3-dicarboxylate substitution directly.

The method of the present invention utilizing enamines of formula XXXIV which react with formula XXXV oxymethylene oxalacetates and subsequent addition of an ammonia source produces pyridine 2,3-dicarboxylates with substituents in the 5, 6, or 5 and 6 positions directly and does not limit these substituents to those which are electron withdrawing.

Thus, pyridine-2,3-dicarboxylates containing substituents in the 5 and/or 6 position may conveniently be prepared by admixing essentially equimolar amounts of a formula XXXIV enamine and a formula XXXV oxalacetate in a suitable solvent and stirring the resulting reaction mixture for from five minutes to 24 hours at a temperature of from −78° C. to 50° C. Treatment of the thus-formed adduct with a minimum of 1 molar equivalent of ammonia or an ammonia source and continued stirring for from 0.5 to 72 hours at a temperature of from 0° C. to the boiling point of the mixture gives the desired pyridine-2,3-dicarboxylate which may be isolated by standard laboratory techniques such as extraction or column chromatography.

Many fused heteropyridine diesters of the general formula XXXI may be obtained by oxidative cleavage of appropriately substituted heteroquinoline compounds which may be prepared by the method of O. Meth-Cohn, J. Chem. Soc., Perkin I, 2509 (1981), directly, or cleavage followed by reactions with amines, hydrazines, hydroxide or hydrogen sulfide or a sulfide salt as illustrated in Flow Diagram VII below:

FLOW DIAGRAM VII

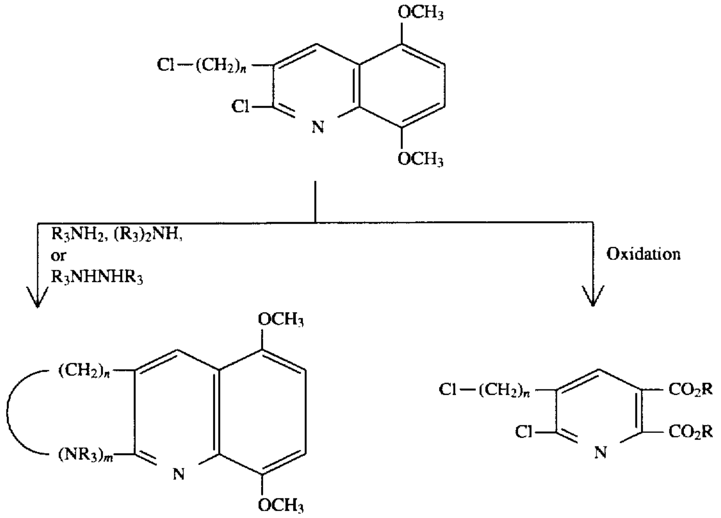

-continued

FLOW DIAGRAM VII

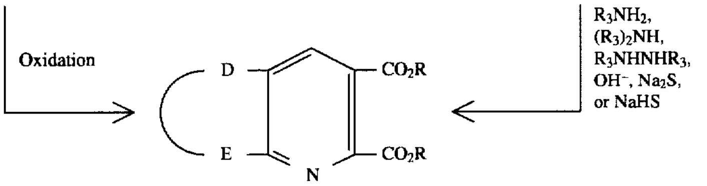

XXXI wherein D–E together with the aromatic carbons to which they are joined, represents a five- or six-membered fused heterocyclic ring containing one or two N or $NR_3$; oxygen or sulfur; m is an integer of 1 or integer 2; .n is an integer of from 1 to 3 but must be 3 in the case of reaction with $Na_2S$ or NaSH; m plus n=3 or 4; R is hydrogen, $CH_3$ or $C_2H_5$ and $R_3$ is as described in Formula I–XXIV.

Another general approach to obtaining fused heteropyridine diesters which are useful as intermediates for the preparation of the novel formula I–XXIV compounds of the invention is ring closure of 5-nitro-6-disubstituted pyridine-2,3-dicarboxylic acid esters, which may be prepared by the reaction of an ethoxymethyleneoxalacetate ester with nitroacetone or nitroacetamide.

For example, pyrrolopyridines may be prepared by condensation of 5-nitro-6-methylpyridine-2,3-dicarboxylates with N,N-dialkyl carboxylic amide diacetals, followed by reduction and concomitant cyclization, depending on reaction conditions. Alkylation of the product gives a mixture of two $NR_3$ compounds, where $R_3$ is alkyl or alkoxy, as illustrated in Flow Diagram VIII below, wherein $R_3$ and $R_4$ are as described for formulas I–XXIV above.

FLOW DIAGRAM VIII

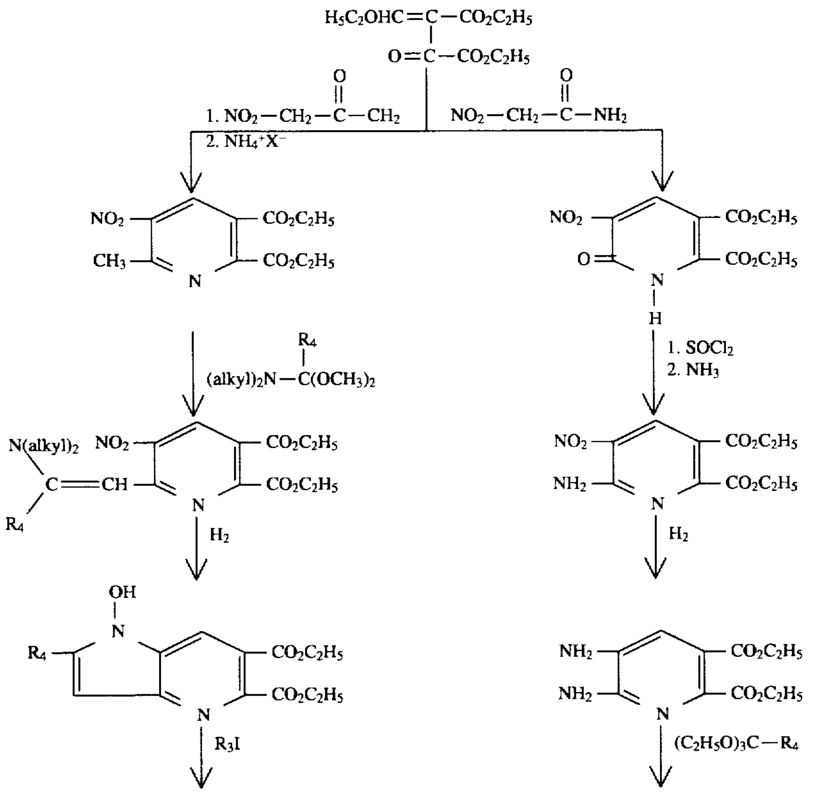

-continued
FLOW DIAGRAM VIII

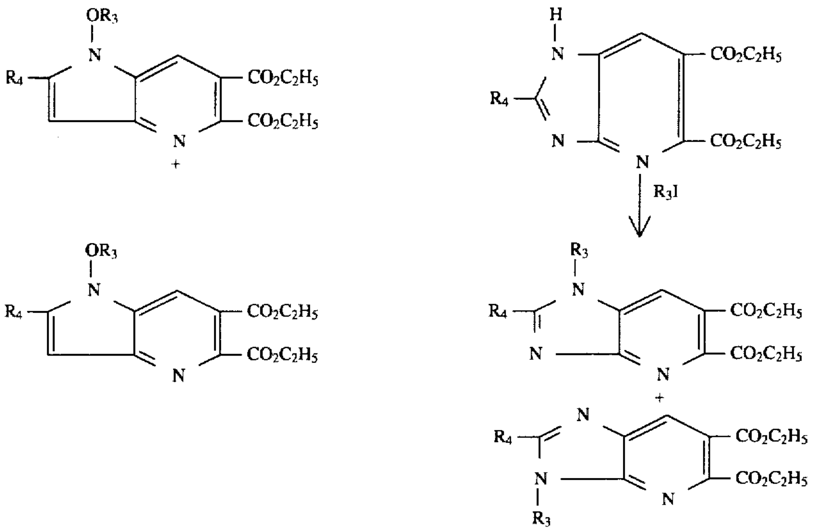

wherein $R_3$ is $C_1$–$C_4$ alkyl.

5-Acetyl-1,6-dihydro-6-oxo-2,3-pyridinedicarboxylic acid esters, [referred to as keto-pyridone diesters, which may readily be prepared by adding sodium acetate to a stirred mixture of dialkyl (ethoxymethylene) oxalacetate and acetoacetamide in an alcohol] provide a source of a variety of fused heteropyridine-2,3-dicarboxylate esters which are useful as intermediates for the preparation of herbicidal (2-imidazolin-2-yl) fused heteropyridine compounds of the invention.

Pyranopyridine diesters may be prepared from the 5-acetyl-6-pyridone-2,3-dicarboxylates, by condensation with N,N-dialkyl carboxylic acid dineopentyl acetals giving enaminone intermediates which cyclize with acid to the pyranone compounds. Further reduction and/or alkylation and dehydration can give a variety of intermediates depending on the selected conditions.

FLOW DIAGRAM IX

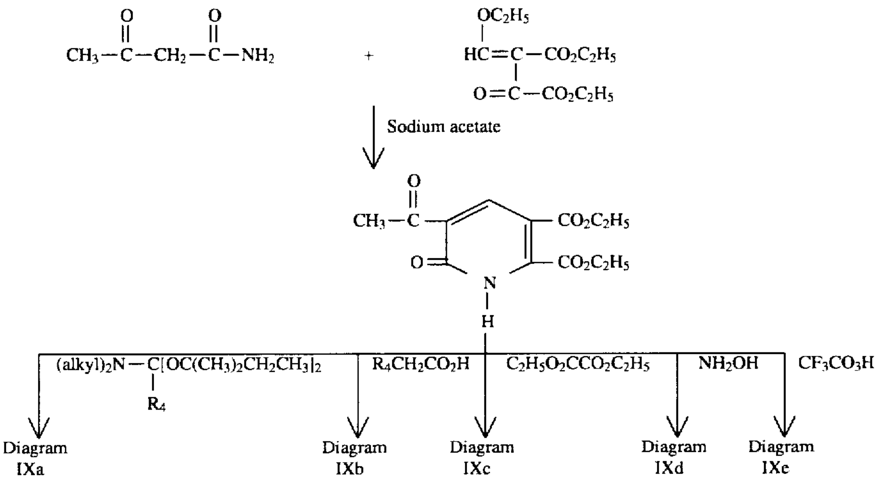

Additionally, an acetyl pyridone may be condensed with an appropriately substituted carboxylic acid (phenylacetic acid for example), which may be reduced to the pyranopyridine diesters. Other keto-pyridone diesters give similar compounds with various alkyl substituents in place of 4-methyl.

Condensation of ketopyridones with dialkyl oxalates give intermediates which are cyclized by acid catalysis.

5-Acetyl-6-pyridone-2,3-dicarboxylates also can undergo reaction with peracids to give the 5-hydroxy-6-pyridine-2,3-dicarboxylates, or form oximes which can undergo rearrangement and after hydrolysis, yield 5-amino-6-pyridone-2,3-dicarboxylates.

These 5-amino and 5-hydroxy compounds may be utilized as intermediates for the preparation of oxazolo, morpholino, dioxolo and dioxanopyridine diesters. These reaction sequences are in general illustrated in Flow Diagrams IXa to IXe below.

FLOW DIAGRAM IXa
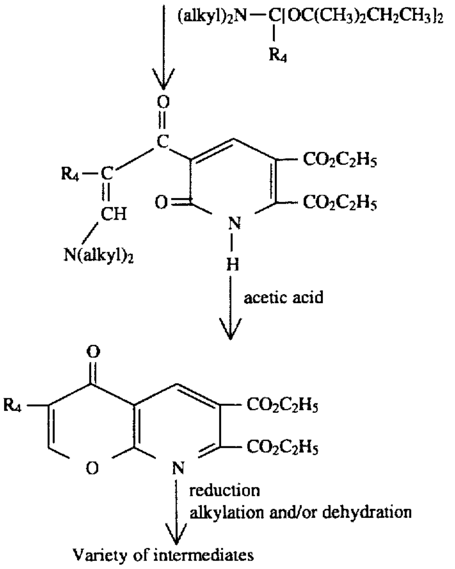
FLOW DIAGRAM IXb
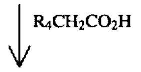
-continued
FLOW DIAGRAM IXb
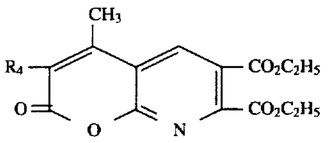
FLOW DIAGRAM IXc
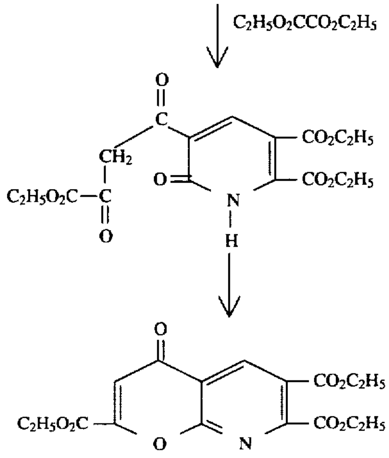
FLOW DIAGRAM IXd
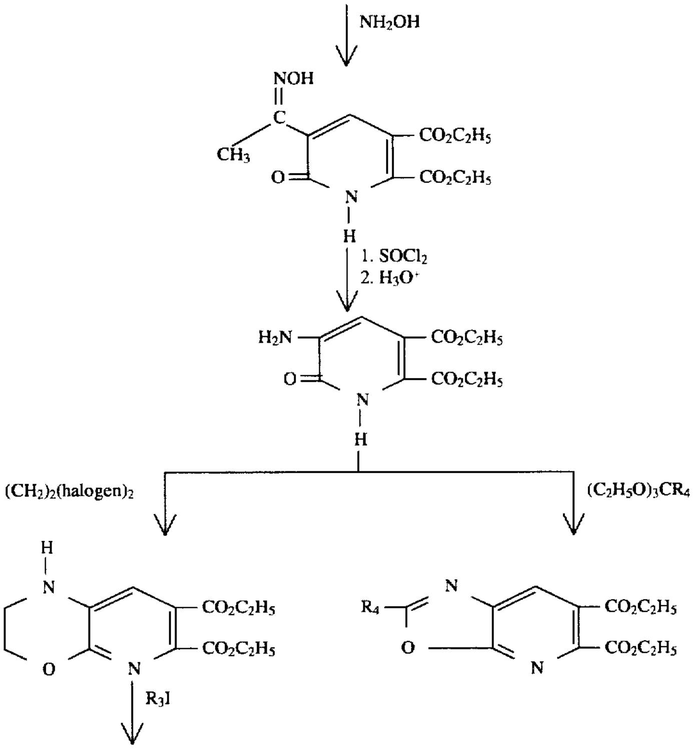

-continued

FLOW DIAGRAM IXd

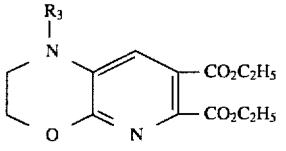

FLOW DIAGRAM IXe

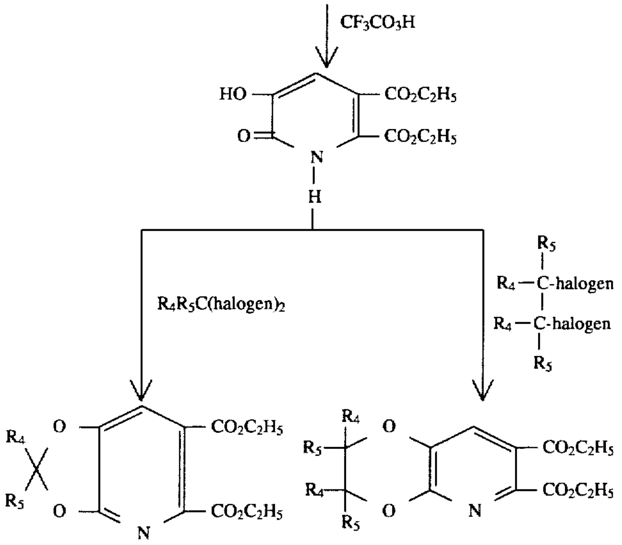

6-Pyridone-2,3,5-tricarboxylic esters can be prepared by condensation of an ester amide with an ethoxymethylene oxalacetate ester and then converted to the 6-chloro compound. The later chloro compound may then be employed in the synthesis of pyrrolopyride diesters by reaction of an N-substituted amino acid ester, with added base, followed by cyclization using alkoxide as illustrated in Flow Diagram X below. The resulting pyrrolopyridine compounds can be further alkylated, selectively decarboxylated, reduced and/or debydrated to a variety of substituted compounds.

FLOW DIAGRAM X

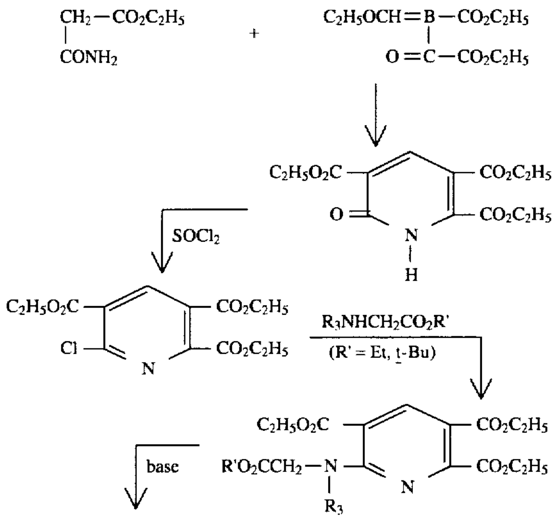

-continued

FLOW DIAGRAM X

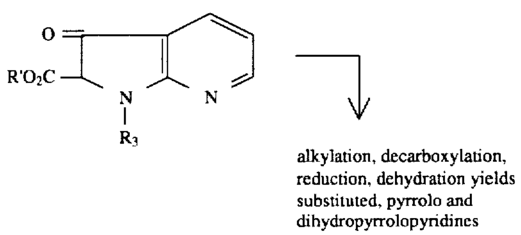

Other diester compounds are prepared by a novel reaction which employs a thermal Dieis-Alder Reaction of an appropriately substituted asymmetric triazine diester, followed by loss or nitrogen. An example of this type of reaction sequence is described by G. Seitz and S. Dietrich, Arch. Pbarm., 317,379 (1984). Asymmetic triazine diesters which are useful in this reaction are prepared from substituted open chain precursors, containing one or more heteroatoms in the chain, by reaction with dialkyl 2,3-dioxosuccinate. Open chain precursors may be prepared, for example, from methylthiosemicarbazide and an 1-alkynyl alcohol, amine or mercaptan. Certain other triazine intermediates may be prepared from an amidrazone, prepared via the nitrile. The triazine need not be isolated; heating can continue until the desired product is formed.

These reactions are illustrated in Flow Diagrams XI and XII below.

FLOW DIAGRAM XI
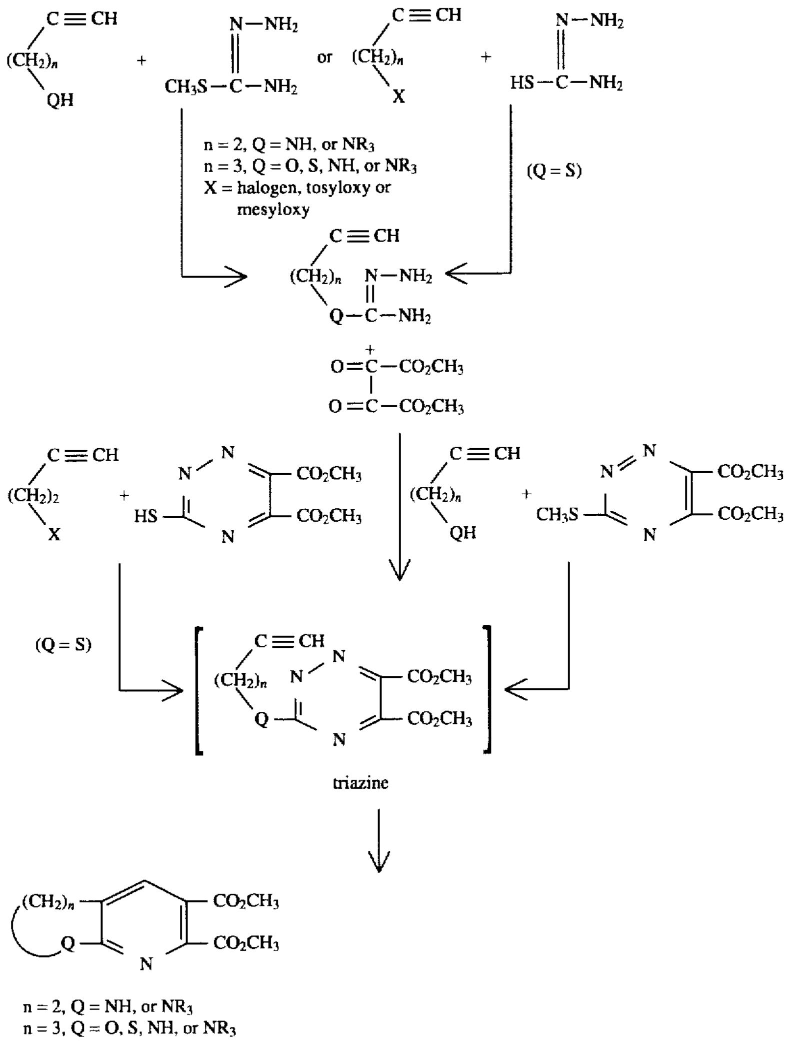
FLOW DIAGRAM XII
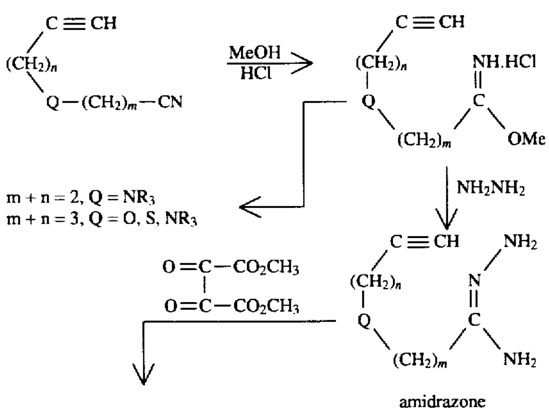
-continued
FLOW DIAGRAM XII
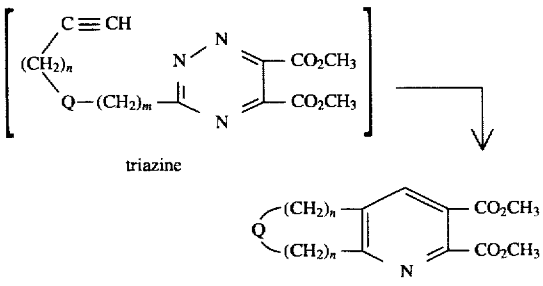
The formula I-IV and XVII-XX (2-imidazolin-2-yl)heteropyridines and the formula V-XVI imidazopyrrolopyridinediones of the present invention are exceedingly effective herbicidal agents useful for the control of an exceptionally wide variety of herbaceous and woody annual and perennial monocotyledonous and dicotyledonous plants. Moreover, these compounds are herbicidally effective for controlling weeds indigenous to both dry land and wet land areas. They are also useful as aquatic herbicides and are unique in their effectiveness in controlling the above-said plants when applied to the foliage thereof or to the soil or water containing seeds or other propagating organs of said plants such as tubers, rhizomes or stolons, at rates of from about 0.016 to 4.0 kg/ha, and preferably at rates from about 0.032 to 2.0 kg/ha.

It is of course obvious that the rates of application above the 4.0 kg/ha level can also be used to effectively kill undesirable plant species; however, rates of application of toxicant above the level necessary to kill the undesirable plants should be avoided since application of excessive amounts of toxicant is costly and serves no useful function in the environment.

Among the plants which may be controlled with the compounds of this invention are: *Elatine triandra, Sagittaria pygmaea, Scirpus hotarui, Cyperus serotinus, Eclipta alba, Cyperus difformis, Rotala indica, Lindernia pyridonoria, Echinochloa crus-galli, Digitaria sanguinalis, Setaria viridis, Cyperus rotundus, Convolvulus arvensis, Agropyron repens, Datura stramonium, Alopercurus myosuroides, Ipomoea spp., Sida spinosa, Ambrosia artemisiifolia, Eichornia crassipes, Xanthium pensylvanicum, Sesbahia exaltata, Arena fatua, Abutilon theophrasti, Bromus tectorum, Sorghum halepense, Lolium spp., Panicum dichotomiflorum, Matricaria spp., Amaranthus retroflexus, Cirsium arvense* and *Rumex iaponicus.*

It has been found that the formula I–IV, and XVII-XX (2-imidazolin-2-yl)fused heteropyridines and the formula V–XVI imidazopyrroloheteropyridinediones are generally selective herbicides, particularly effective for controlling undesirable weeds in the presence of leguminous crops such as soybeans, and cereal crops such as wheat, barley, oats and rye. However, certain compounds are less selective than others in this series.

It has also been found that several of the formula (2-imidazolin-2-yl) fused heteropyridines are effective as antilodging agents in cereal crops when applied at rates of application between about 0.5 to 2000 g per hectare. At rates of application not exceeding about 2000 g per hectare, it has also been found that certain of these compounds are effective for increasing branching of leguminous crops and tillering of cereal crops. At rates of application not exceeding 2000 g per hectare, certain of these compounds are useful as dwarflug agents for turf.

Those imidazolinyl fused heteropyridines and derivatives, wherein $R_8$ is a salt-forming cation, which are water soluble, can simply be dispersed in water and applied as a dilute aqueous spray to the foliage of plants or to soil containing propagating organs thereof. These salts also lend themselves to formulation as flowable formulations.

Other fused heteropyridine compounds wherein $R_8$ is a salt-forming cation or represents an ester which is not water soluble lend themselves to formulation as emulsifiable concentrates, thus providing a wide range of formulation options for specific purposes.

The (2-imidazolin-2-yl) fused heteropyridines can also be formulated as wettable powders, flow concentrates, granular formulations and the like.

Wettable powders can be prepared by grinding together about 20% to 45% by weight of a finely divided carrier such as kaolin, bentonire, diatomaceous earth, attapulgite, or the like, 45% to to 80% by weight of the active compound, 2% to 5% by weight of a dispersing agent such as sodium lignosulfonate, and 2% to 5% by weight of a nonionic surfactant, such as octylphenoxy polyethoxy ethanol, nonylphenoxy polyethoxy ethanol or the like.

A typical flowable liquid can be prepared by admixing about 40% by weight of the active ingredient with about 2% by weight of a gelling agent such as bentonire, 3% by weight of a dispersing agent such as sodium 1 ignosulionate, 1% by weight of polyethylene glycol and 54% by weight of water.

A typical emulsifiable concentrate can be prepared by dissolving about 5% to 25% by weight of the active ingredient in about 65% to 90% by weight of N-methylpyrrolidone, isophorone, butyl cellosolve, methylacetate or the like and dispersing therein about 5% to 10% by weight of a nonionic surfactant such as an alkylphenoxy polyethoxy alcohol. This concentrate is dispersed in water for application as a liquid spray.

When the compounds of the invention are to be used as herbicides where soil treatments are involved, the compounds may be prepared and applied as granular products. Preparation of the granular product can be achieved by dissolving the active compound in a solvent such as methylene chloride, N-methylpyrrolidone or the like and spraying the thus prepared solution on a granular carrier such as corncob grits, sand, attapulgite, kaolin or the like.

The granular product thus prepared generally comprises about 3% to 20% by weight of the active ingredient and about 97% to 80% by weight of the granular carrier.

In order to facilitate a further understanding of the invention, the following examples are presented primarily for the purpose of illustrating certain more specific details thereof. The invention is not to be deemed limited thereby except as defined in the claims. Unless otherwise noted, all parts are by weight.

EXAMPLE 1

Preparation of diethyl 1,6-dihydro-5-nitro-6-oxo-2,3-pyridinedicarboxylate

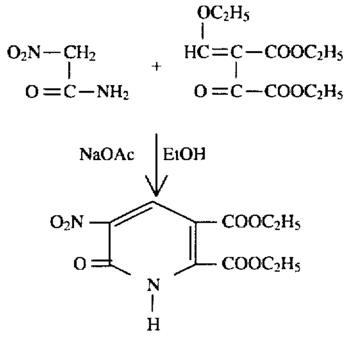

Diethyl(ethoxymethylene)oxalacetate (5.63 g, 0.023 mol,) is dissolved under $N_2$ atmosphere in 20 mL of absolute ethanol and cooled to 0° C. Nitroacetamide (2.00 g, 0.019 mol,) (S. K. Brownstein, J. Org. Chem 23, 113 (1958)) and sodium acetate (1.56 g, 0.019 mol,) are added and the mixture is stirred at room temperature for 15 hours. The suspension is diluted with 15 mL of absolute ethanol and acidified to pH 2 with concentrated HCl. The inorganics are removed by filtration and the filtrate is concentrated to an oily solid which is gravity chromatographed, first with methylene chloride and then 2% methanol in methylene chloride. The fractions are combined and stripped to give 4.28 g of the title product as a yellow solid, 78.4% yield, melting point 144°–145° C.

EXAMPLE 2

Preparation of diethyl 6-chloro-5-nitro-2,3-pyridinedicarboxylate

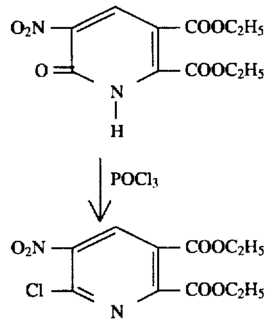

Diethyl 1,6-dihydro-5-nitro-6-oxo-2,3-pyridinedicarboxylate (26.23 g, 0,092 mol) is partially dissolved under $N_2$ atmosphere in 250 mL of phosphorous oxychloride and the mixture is heated to 80° C. for 15 hours. The mixture is cooled and concentrated and the resulting oil dissolved in ethyl acetate and washed with water, 10% $K_2CO_3$ and brine. The organic layer is dried over $MgSO_4$, filtered and the solvent removed to yield a solid which is recrystallized from absolute ethanol/water to give 20.65 g of the produce as a brown solid in 73.9% yield, having a melting point of 84.5°–86° C.

EXAMPLE 3

Preparation of diethyl 6-amino-5-nitro-2,3-pyridinedicarboxylate

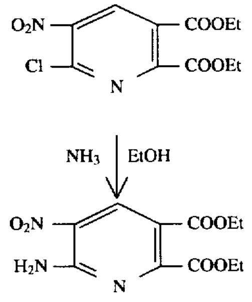

Diethyl 6-chloro-5-nitro-2,3-pyridinedicarboxylate (20.59 g, 0.068 mol) is suspended in 500 mL of absolute ethanol and the solution cooled to 0° C. Gaseous ammonia is bubbled in for one hour, causing an exotherm to 20° C. The mixture is concentrated to a brown solid and partitioned between ethyl acetate and water. The organic layer is dried over $Na_2SO_4$, filtered and the solvent removed to yield a yellow solid, melting point 120°–122° C.

EXAMPLE 4

Preparation of diethyl 5,6-diamino-2,3-pyridinedicarboxylate

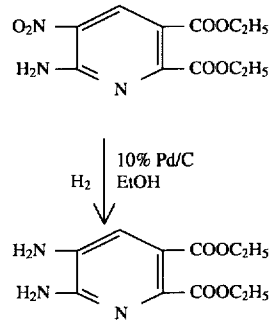

Diethyl 6-amino-5-nitro-2,3-pyridinedicarboxylate (5.00 g, 0.0176 mol) is suspended in 250 mL of absolute ethanol and the mixture cooled to 0° C. Palladium on carbon (50 g of 10% is added and the mixture is shaken under 50 psi hydrogen in a Parr apparatus for four hours. The catalyst is removed by filtration through a pad of Celite, and the filtrate is concentrated to yield 4.21 g (94.2%) of product as a yellow solid, melting point 143°–146.5° C.

EXAMPLE 5

Preparation of diethyl 2-methyl-imidazo[4,5-]b]pyridine-5,6-dicarboxylate

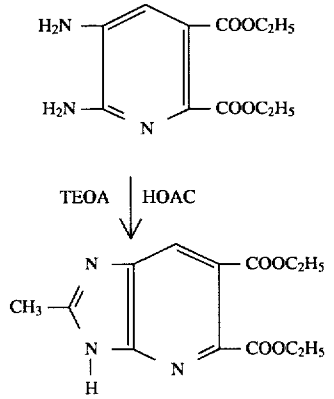

Diethyl 5,6-diamino-2,3-pyridinedicarboxylate (10.38 g, 0.041 mol) is stirred under an $N_2$ atmosphere in 100 mL glacial acetic acid, to give a clear orange solution. Triethylorthoacetate (TEOA), (0.19 mol) is then added and the mixture is heated to reflux for 15 hours. The cooled solution is poured into ice water and neutralized with ammonium hydroxide. The solution is extracted with ethyl acetate, the combined organic layers washed with brine, dried over $Na_2SO_4$, filtered and concentrated to an oil. The oil is taken up in ethyl acetate and the desired product is precipitated by the addition of hexanes in two crops of beige solid, totalling 8.11 g (71.3%), having a melting point of 164°–165° C.

EXAMPLE 6

Preparation of diethyl 1,2-dimethyl-1H-imidazo[5,4-b]-pyridine-5,6-dicarboxylate (Isomer A) and diethyl 1,2-dimethyl 1H-imidazo[4,5-b]pyridine-5,6-dicarboxylate (Isomer B)

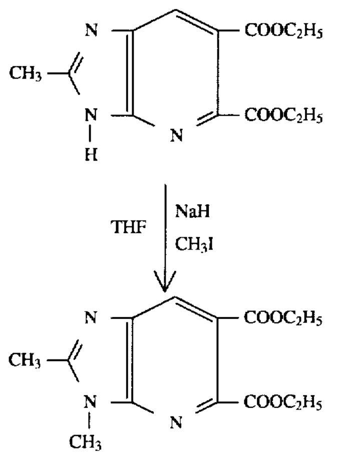

Isomer A

+

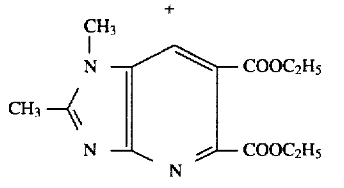

Isomer B

Diethyl 2-methylimidazo[4,5-b]pyridine-5,6-dicarboxylate (8.11 g, 0.029mol,) is suspended in 250 mL THF. Sodium hydride (1.61 g, 607, dispersion in mineral oil, 0.040 mol) is added in one portion, causing an exotherm to 34° C. Methyl iodide (3.6 mL, 0.058 tool) is added, causing the precipitation of a large amount of solid. THF, 150 mL is then added and the suspension stirred at room temperature for 15 hours. The mixture is poured into 500 mL water and the mixture extracted with methylene chloride. The organic layers are combined, washed with brine, dried over $Na_2SO_4$ and concentrated to give 5.59 g of a brown solid.

The aqueous layer is concentrated to a solid which is triturated with ethyl acetate and filtered. The filtrate is concentrated to yield 0.59 g of a black oil and the solid is suspended in acetone and heated to reflux. The suspension is filtered, and the filtrate is stripped to 1.82 g of a yellow solid.

The solid obtained by extraction and the oil are mixtures of isomers. The yellow solid obtained from the boiling acetone is primarily isomer B.

The isomer mixture is separated by chromatography, first using methylene chloride, then 1% methanol in methylene chloride, yielding the purified faster moving isomer A as an oil (0.9 g). Structural assignments of A and B are made on the basis of $^{13}C$ NMR spectroscopy.

EXAMPLE 7

Preparation of 4-amino-1-methylpyrazole

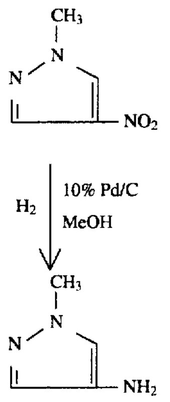

1-Methyl-4-nitropyrazole (6.00 g, 0.047 tool) (M. E. Foster and J. Hurst, J. Chem. Soc. Perkin 1,507, (1976)) is dissolved in 185 mL of methanol and cooled while 0.47 g of 10% palladium on carbon is added. The mixture is shaken for 15 hours under 50 psi hydrogen in a Parr hydrogenator. The catalyst is removed by filtration through a pad of celite and the filtrate concentrated to give a red oil which is used immediately without characterization or purification.

EXAMPLE 8

Preparation of dimethyl [1-methylpyrazol-4-yl)amino]butenedicarboxylate

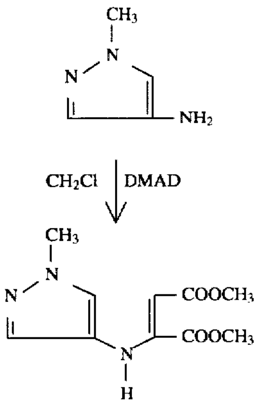

Dimethylacetylenedicarboxylate (6.4 mL, 0.052 mol) is dissolved in 75 mL methylene chloride and the mixture cooled to 0° C. Unpurified 4-amino-l-methylpyrazole (assumed to be 4.58 g, 0.047 mol) is dissolved in 25 mL methylene chloride and added dropwise so that the reaction temperature remains below 5° C. The solution is stirred for one hour, and is then allowed to warm to room temperature and stirred for 65 hours. The mixture is concentrated and the resulting oil is used without characterization or purification.

EXAMPLE 9

Preparation of dimethyl 1-methylpyrazolo[4,3-b]pyridine-5,6-dicarboxylate

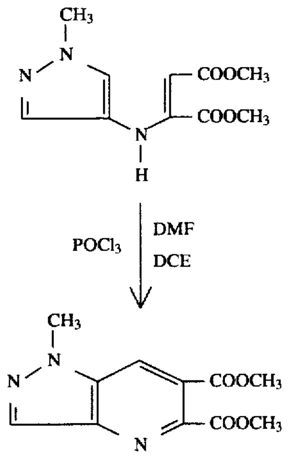

Dimethylformamide (7.4 mL, 0.096 mol) is dissolved in 125 mL dichloroethane and the mixture cooled to −5° C. in an acetone/ice bath. Phosphorous oxychloride (8.9 mL, 0.095 mol) is added in one portion and the clear colorless solution is allowed to warm slowly to room temperature, gradually turning yellow. The unpurified dimethyl [(1-methylpyrazol-4-yl)amino]-butenedicarboxylate is dissolved in 75 mL of dichloroethane and added to the chilled Viismeier reagent dropwise keeping the reaction temperature below 5° C. The mixture is allowed to warm slowly to room temperature over four hours, and then is heated to reflux for one hour. The mixture is concentrated to a solid which is chromatographed using 3:1 hexanes/ethyl acetate. The fractions containing the desired product are combined and concentrated to give the product as a white solid (16.93 g, 71.4%), melting point 148°–149° C.

EXAMPLE 10

Preparation of 3-methyl-5-amino isoxazole

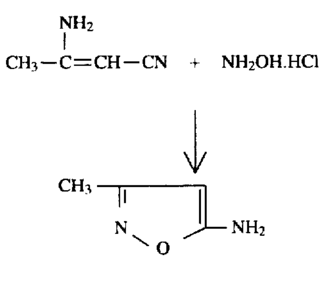

Hydroxylamine hydrochloride (34.81 g, 0.50 mol) is dissolved in 100 mL water and the solution cooled in an ice bath for ten minutes. Then 3-aminocrotononitrile (48.30 g of 85%, 0.50 mol) is added portionwise over ten minutes. After stirring for 30 minutes, the solution turns orange and a solid precipitates. The solid is collected by filtration and recrystallized from benzene, giving the product (30.98 g, 63.2%) as a white solid, having a melting point of 77°–79° C.

EXAMPLE 11

Preparation of diethyl 3-methylisoxazolo[5,4-b]pyridine-5,6-dicarboxylate

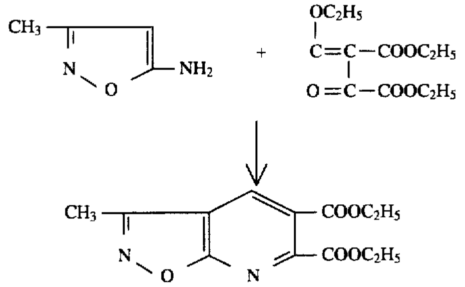

5-Amino-3-methylisoxazole (12.25 g, 0.125 mol) and diethyl(ethoxymethylene)oxalacetate (33.55 g, 0.138 mol) are dissolved in 200 mL glacial acetic acid under an $N_2$ atmosphere. The solution is heated to reflux for two hours, then stirred at room temperature for 65 hours. The solution is poured into ice water, causing the precipitation of a red solid. The solid is collected by filtration, redissolved in 175 mL glacial acetic acid and reprecipitated with the addition of ice. The resulting yellow solid is collected by filtration and air dried, giving 14.20 g of product, yield 40.8%, having melting point 95°–99° C. A small amount is recrystallized from hexanes/ethyl acetate, melting point 100°–101° C.

EXAMPLE 12

Preparation of diethyl 6,7-dihydro-5H-pyridine-2,3-dicarboxylate

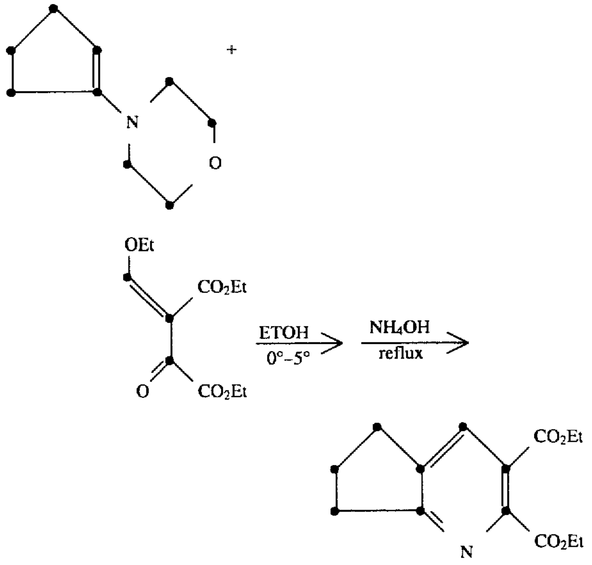

To a solution of diethyl ethoxymethyleneoxalacetate (10.25 g, 0.042 tool)dissolved in ethanol (100 mL) at 0° is added 1-morpholinocyclopentene (6.8 mL, 0.042 mol). After an initial exotherm to 9°, the reaction is stirred at 5° for 20 minutes. Concentrated $NH_4OH$ (20 mL) is added and the reaction solution is heated to reflux for 30 minutes, concentrated in vacuo to an oil, diluted with $H_2O$ (100 mL), and extracted with $CH_2Cl_2$. Chromatography of the extract over silica gel with hexane-ethyl acetate (7:3) elution gives the product as an oil (5.06 g. 0.019 mol, 46%).

EXAMPLE 13

Preparation of diethyl 5-ethylpyridine-2,3-dicarboxylate

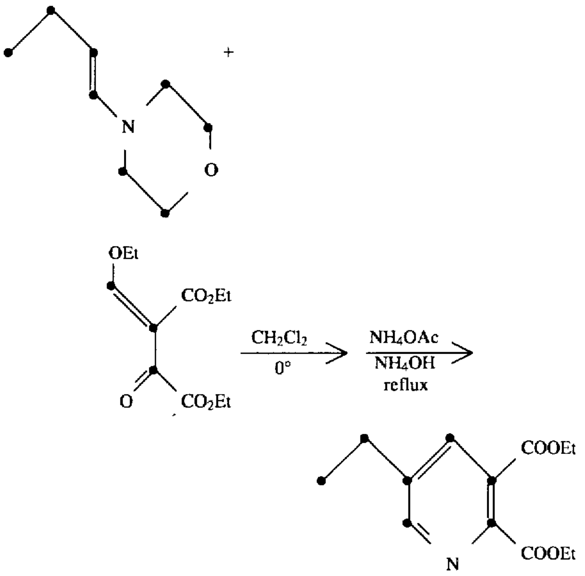

Diethyl ethoxymethyleneoxalacetate (3.17 g, 0.013 mol) is added to a solution of 1-morpholinobutene (1.84 g, 0,013 mol) dissolved in $CH_2C_{12}$ (40 mL) at 0°. The solution is concentrated in vacuo, and ammonium acetate (50 g), ammonium hydroxide (10 mL), tetrahydrofuran (20 mL) and 95% ethanol (20 mL) are added. The solution is heated to reflux for 30 minutes, then held at 3° for 72 hours. The reaction solution is then partitioned between water and ethyl acetate. The organic layer is dried over sodium sulfate and concentrated in vacuo to give the product (1.85 g, 0.0074 mol, 57%).

EXAMPLE 14

Preparation of diethyl 5-ethylpyridine-2,3-dicarboxylate

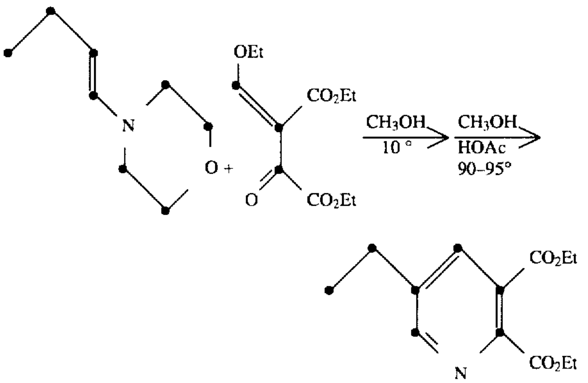

To a solution of diethyl ethoxymethyleneoxalacetate (43.2 g, 0.16 mol) dissolved in $CH_3OH$ (150 mL) at −10° under $N_2$ is added 1-morpholinobutene (25 g, 0.16 mol). The reaction is slowly warmed to room temperature over three hours, after which the $CH_3OH$ is removed in vacuo. The residue is dissolved in acetic acid (100 mL) and this solution slowly added to $NH_4Cl$ (34.2 g, 0.64 mol) dissolved in acetic acid (200 mL) at 50°–70°. The reaction is then heated to 90°–95° for two hours and 30 minutes, concentrated in vacuo, partitioned between water and the $CH_2Cl_2$, and the organic phase chromatographed over silica gel with $CH_2Cl_2$–$CH_3CN$ (95:5) elution to give the product as an oil. Distillation at 123°–155° at 0.15mm gives the product (23.4 g, 83% pure, 55%).

EXAMPLE 15

Preparation of diethyl 6,7-dihydro-5H-pyridine-2,3-carboxylate

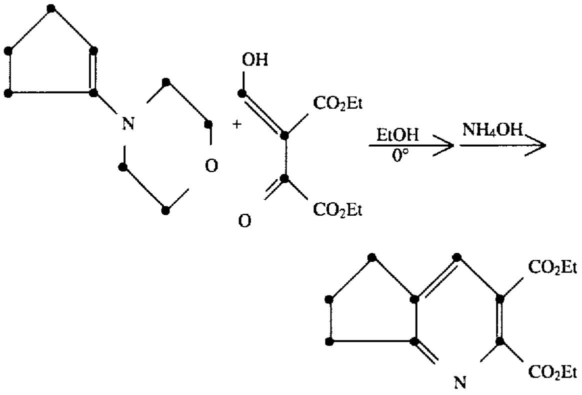

Diethyl hydroxymethyleneoxalacetate is prepared by the method of R. Jones, *J. Am. Chem. Soc.* 73, 3684 (1951).

Diethyl hydroxymethyleneoxalacetate (5.0 g, 0.0231 mol) is dissolved in ethanol (50 mL) under $N_2$ and cooled to 3°. To this is added 1-morpholinocyclopentene (3.7 mL, 0.231 mol). The reaction is stirred for 20 minutes at a temperature of 3°–7° C., then treated with concentrated $NH_4OH$ (10 mL), stirred at room temperature overnight, then concentrated in vacuo. The residue is partitioned between $CH_2Cl_2$ and $H_2O$, and after further extraction of the aqueous layer with $CH_2Cl_2$, the combined organic layers are dried over $Na_2SO_4$ and concentrated in vacuo to an orange oil. Chromatography over silica gel with hexane-ethylacetate (4:1) elution gives the product as a yellow oil (0.85 g, 0.0032 mol, 14%).

EXAMPLE 16

Preparation of diethyl 5,7-dihydro[3,4-h]pyridine-2,3-dicarboxylate and diethyl 2,3-dihydrofuro[2,3-b]pyridine-5,6-dicarboxylate

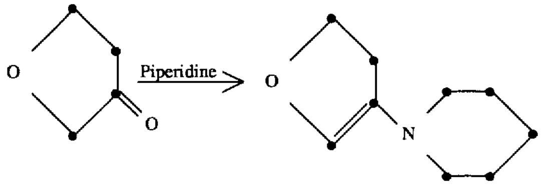

I and +

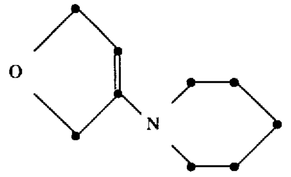

II

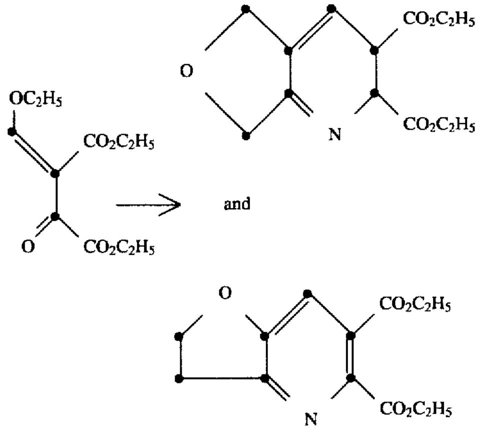

and

To a solution of tetrahydrofuran-3-one (J. Pharm. Sci., 59, 1678 (1970); 46.5 g, 0.540mol) in benzene (250 mL), stirred at room temperature, is added piperidine (45.98 g, 0.540 mol) and p-toluenesulfonic acid monohydrate (0.46 g, 0.002mol). The mixture is heated at reflux under a Dean-Stark trap for four hours, cooled and stripped to a dark brown oil consisting of a 1:1 mixture of 2,3- and 2,5-dihydrofuran enamines (I and II; Recl. Trav. Chim., 92,865 (1973)). Then ethanol (500 mL) and diethyl ethoxymethylene oxalacetate (178.79 g, 1.35 mol) is added and stirring continued for 45 minutes. Ammonium acetate (1.24.87 g, 1.62 tool) is added and the mixture is beated at reflux for 45 minutes. After cooling, the solvents are removed and the off-white solids diethyl dihydrofuro[3,4-b]pyridine-5,6-carboxylate and diethyl dihydrofuro[3,2-b]pyridine-5,6-carboxylate are separated by chromatography, on silica gel, eluting with hexaneethyl acetate. The mass spectrum shows the parent peak (M+H/e) for both compounds at 266.

EXAMPLE 17

Preparation of 5,7-dihydro[3,4-b]pyridine-2,3-dicarboxylic acid

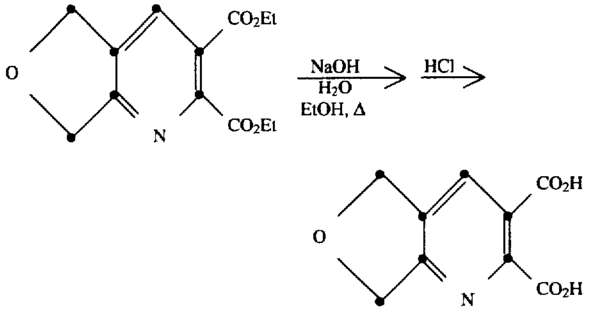

The diester (6.64 g, 0,025 tool) is added to ethanol (50 mL) and water (50 mL), the mixture treated with NaOH (10.0 g, 0.25 mol) and stirred at room temperature for three days. The mixture is then heated to reflux for one hour, diluted with water (50 mL) to dissolve remaining solids, and again heated to reflux for three hours. The ethanol is removed from the reaction in vacuo, leaving an aqueous solution that is acidified with concentrated HCl, then concentrated in vacuo to a solid. The solid is extracted with first acetone, and then hot ethanol. The combined extracts are concentrated in vacuo to give the diacid (2.93 g, 0.014 tool, 56% yield).

EXAMPLE 18

Preparation of 5,7-dihydro[3,4-b ]pyridine-2,3-dicarboxylic acid anhydride

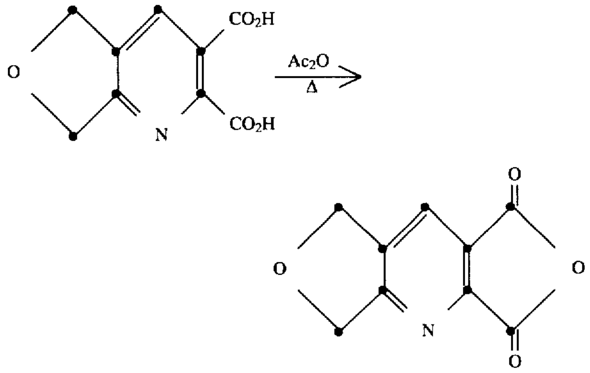

The diacid 5,7-dihydrofuro[3,4-b]pyridine-2,3-dicarboxylic acid (2.93 g, 0,014 tool) is added to the acetic anhydride (100 mL) and the mixture heated to 90° for three hours. Solids (0.25 g) are removed by filtration and the filtrate concentrated in vacuo. The initial precipitate is combined with the concentrate to give 5 7-dihydro[3 4-b] pyridine-2 3-dicarboxylic acid anhydride.

EXAMPLE 19

Preparation of 5,7-dihydro-3-(4-isopropyl-4-methyl-5-oxo-2-imidazolin-2-yl)furo[3, 4-b]pyridine-2-carboxylic acid

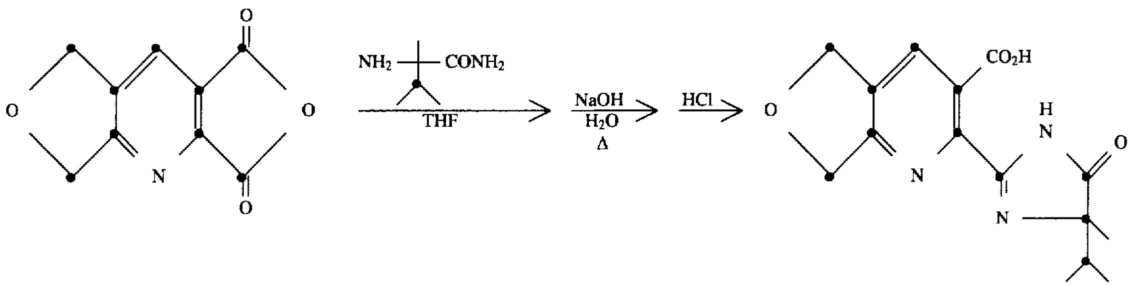

The anhydride (2.52 g, 0.013 mol) is dissolved in THF (100 mL) and treated with the amino amide (1.95 g, 0.015 mol). This mixture is stirred at room temperature overnight, then another portion of amino amide (1.95 g, 0.015 mol) is added. The reaction is refluxed for 2.5 hours, cooled and concentrated in vacuo. The residue is dissolved in $H_2O$ (80 mL) and NaOH (3.12 g, 0.078 mol). This solution is heated at 8.5° for one hour, then stirred at room temperature overnight. The reaction is then heated again at 85° for two hours, cooled, acidified with conc. HCl to pH 2–3, and filtered. The desired product is found in the filtrate which is concentrated in vacuo, then disolved in methanol and passed thru a small pad of silica gel to remove the polar material. The methanol fractions are column chromatography over silica gel with Hexane: EtOAc (19:1) elution to give the product as a pale yellow solid (0.55 g, mol, 14% yield); mp 115°–118° . Mass spectrum M+H=304.

EXAMPLE 20

Preparation of diethyl dihydrothieno[3,2-b]pyridine-5,6-dicarboxylate

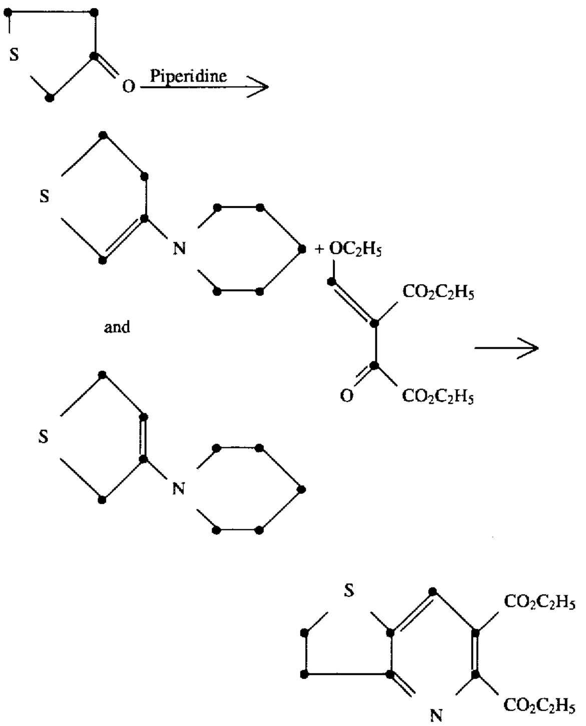

and

To a solution of tetrahydrothiopene-3-one (Maybridge Chem. Co.; 20.0 g, 0.196 mol) in benzene (100 mL), stirred at room temperature, is added piperidine (16.7 g, 0.196 tool) and p-toluenesulfonic acid monohydrate (0.20 g, 0.001 mol). The mixture is heated at reflux under a Dean-Stark trap for four hours, cooled and stripped to a dark brown oil consisting of a 1:1 mixture of 2,3- and 2,5-dihydrothiophene enamines (Recl. Trav. Chim., 92, 865 (1973)).

To the above enamine mixture is added ethanol (100 mL) and diethyl ethoxymethylene oxalacetate (72.1 g, 0.294 mol) and stirred for 45 minutes. Ammonium acetate (45.3 g, 0.588 tool) is added in one portion and the mixture is heated at reflux for 45 minutes.

After cooling, the solvents are stripped and the yellow solid diethyl dihydrothieno[3,2-b]pyridine-5,6-dicarboxylate product is obtained by chromatography after eluting with nexane-ethyl acetate. The mass spectrum shows the parent peak (M+H/e) at 28?

Utilizing the above procedure and substituting the appropriate enamine yields the compounds listed in Table I below.

TABLE I
| Enamine | Solvent A | Time A | Temp A | Ammonium Source | Solvent B | Time B | Temp B | Yield | Product |
|---|---|---|---|---|---|---|---|---|---|
| 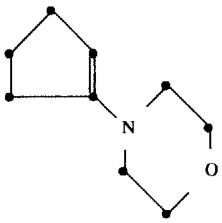 | THF | 2 hrs | 0–25° | EtOH + $NH_4OAc$ | | | | | 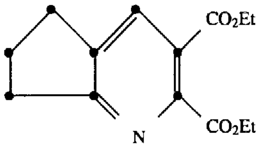 |
| 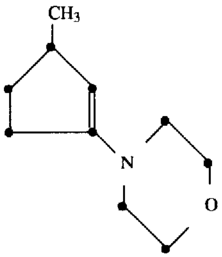 1:1 mixture + 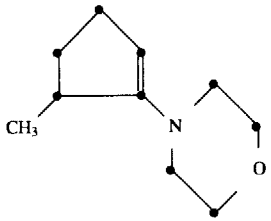 | EtOH | 90 min | 3–7° | $NH_4OH$ | EtOH | 45 min | Reflux | 60% | 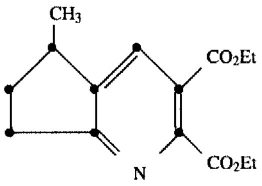 + 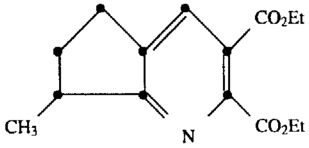 1:1 mixture |
| 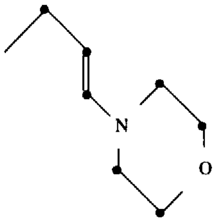 | EtOH | 150 min | 0–50° | $NH_4OH$ + $NH_4OAc$ | EtOH | 24 hrs at 25° then 1 hr at 60° | 25–600 | | 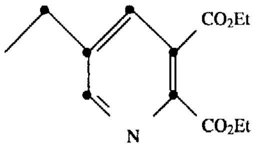 |

TABLE I-continued
| Enamine | Solvent A | Time A | Temp A | Ammonium Source | Solvent B | Time B | Temp B | Yield | Product |
|---|---|---|---|---|---|---|---|---|---|
| 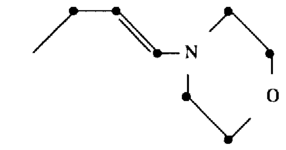 | $CH_2Cl$ | | 0° | $NH_4OH$ + $NH_4OAc$ | THF + EtOH (1:1) | 30 min at reflux then 48 hrs at 5° | 5°–reflux | 43% | 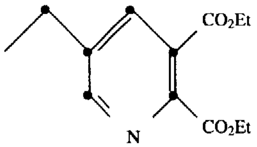 |
| 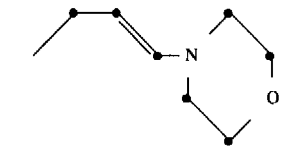 | $CH_3OH$ | 3 hrs | 10–25° | $Nl_4Cl$ | HOAc | 2.5 hrs | 90–95° | 54% | 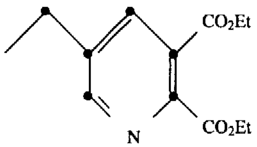 |
| 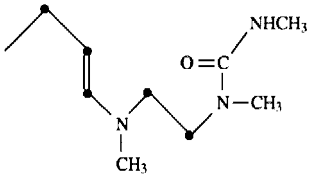 | THF | 2 hrs | 0–25° | $NH_4OH$ + $NH_4OAc$ | EtOH | | | | 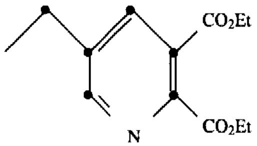 |
| 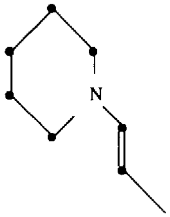 | $CH_2Cl_2$ | 2 hrs | 3–25° | $NH_4OH$ + $NH_4OAc$ | $CH_2Cl_2$—$H_2O$ | 65 hrs | 25° | 40% | 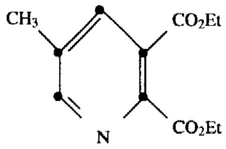 |
| 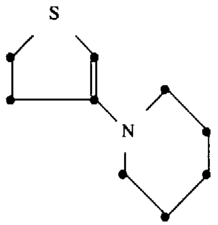 | EtOH | 45 min | 25° | $NH_4OAc$ | EtOH | 45 min | reflux | 34% | 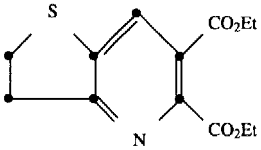 |

TABLE I-continued
| Enamine | Solvent A | Time A | Temp A | Ammonium Source | Solvent B | Time B | Temp B | Yield | Product |
|---|---|---|---|---|---|---|---|---|---|
| 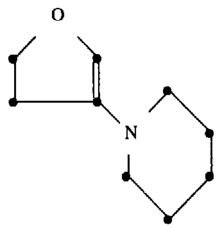 + | EtOH | 45 min | 25° | $NH_4OAc$ | EtOH | 45 min | Reflux | 8% | 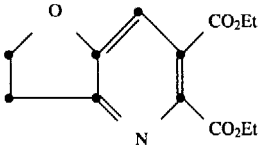 |
| 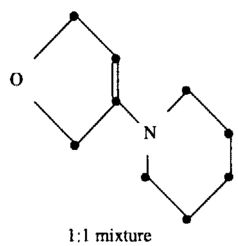 1:1 mixture | | | | | | | | 10% | 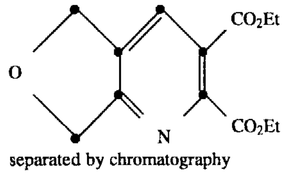 separated by chromatography |

EXAMPLE 21

Preparation of triethyl 5-(3-carboxy-3-hydroxyacryloyl)-1,6-dihydro-6-oxo-2,3-pyridenedicarboxylate

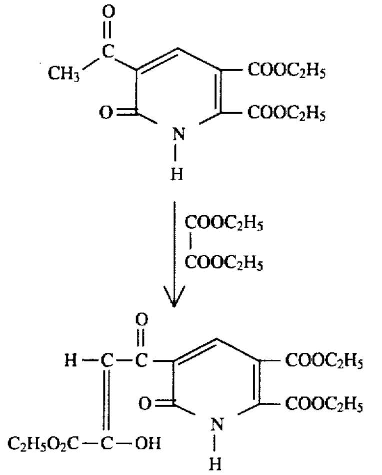

To absolute ethanol 900 mL is added Na pellets (20.61 g, 0.896 tool, 5 eq), giving a clear colorless solution. Diethyl 5-acetyl-1,6-dihydro-6-oxo-2,3-pyridinedicarboxylate (50.00 g, 0.178 mol,) is added in one portion, giving a finely divided pale yellow suspension which is stirred at room temperature for one and one-half hours. Diethyl oxalate (170 mL, 1.25 mol) diluted to 500 mL with absolute ethanol is added over 45 minutes, giving a bright yellow suspension, which is stirred at room temperature for one and one-half hours. The mixture is poured into 1500 mL water and acidified to pH 2 with concentrated HCl, giving the product as a yellow solid which is collected by filtration, having a melting point 162°–164° C.

EXAMPLE 22

Preparation of triethyl 4-oxo-pyrano[2,3-b]pyridine-2,6,7-tricarboxylate

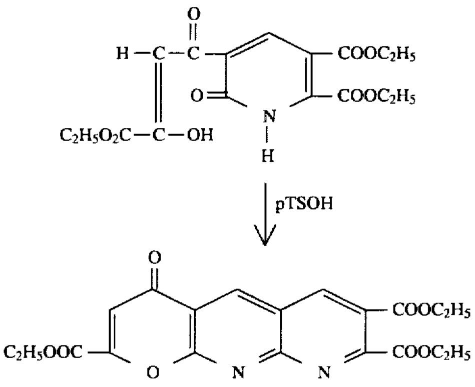

The crude triethyl 5-(3-carboxy-3-hydroxyacryloyl)-1,6-dihydro-6-oxo-2,3-pyridinedicarboxylate (82.16 g, 0.178 mol) is suspended under $N_2$ in 1000 mL xylene with stirring. 2-Toluenesulfonic acid (1.00 g) is added and the suspension is heated to reflux for twelve hours. The solution is filtered to remove the impurities from the starting material and the filtrate is concentrated to a solid, which is recrystallized from methylene chloride/hexanes, giving the product as a yellow solid, (41.85 g. 64.8% over two steps having a melting point 106°–106.5° C.

EXAMPLE 23

Preparation of diethyl 1,8-naphthyridine-2,3-dicarboxylate

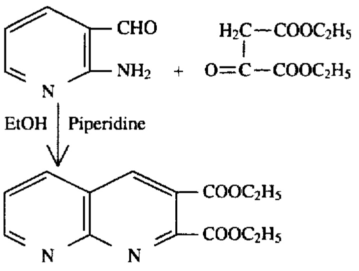

2-Amino-3-formylpyridine (T. G. Majewicz and P. Caluwe, J. Org. Chem. 39, 720 (1974); 37.1 g, 0.30 mol) is suspended under $N_2$ in 400 mls absolute ethanol with stirring. Then piperidine (3 mL) and diethyloxalacetate (115 g, 0.61 mol, 2 eq) are added and the mixture is heated to reflux for 20 hours. Another 17 g diethyloxalacetate (0.09 mol) is added and heating is continued for two hours. The mixture is cooled and concentrated to an oil which is chromatographed using 4:1 hexanes/ethyl acetate, to give the product as a white to pale yellow solid (52.00 g, 62.4%) melting point 88.5°–89.5° C.

Likewise, 1-methyl-4-amino-1,2,3-triazole-5-carboxaldehyde (ref: Chem. Pharm. Bull 27, 2861 (1979) is prepared in situ and condensed under the above conditions to give diethyl 1-methyl-1,2,3-triazole[5,4-b]pyridinedicarboxylate.

EXAMPLE 25

Preparation of diethyl 3-(p-chloropbenyl)-4-methyl-2-oxo-2H-pyrano[2,3-b]pyridine-6,7-dicarboxylate

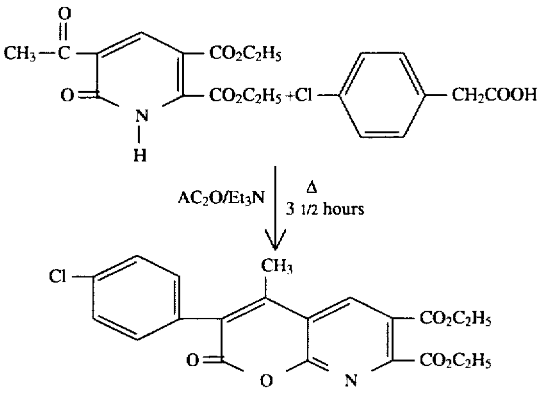

Diethyl 5-acetyl-1,6-dihydro-6-oxo-2,3-pyridinedicarboxylate, (6.0 g, 0.0213 mol), 4-chlorophenyl acetic acid (3.64 g, 0.0213 mol) and triethylamine (3.0 g,.1.5 eq) are refluxed in 50 mL of acetic anhydride for three and one-half hours and then stirred at room temperature overnight. The reaction mixture is poured into 100 mL of ice cold water and the pH is adjusted to 8 with an ammonium hydroxide solution. The crystalline solid is filtered, washed with water, dried and dissolved in 100 mL of methylene chloride. The solution is dried over anhydrous sodium sulfate and the solvent removed under reduced pressure to give the desired product (8.8 g, 99%), which is crystallized from ethyl acetate to give the pure product having a melting point 179°–181° C.

EXAMPLE 26

Preparation of diethyl 3-(m-chlorophenyl)-4-methyl-2-oxo-2H-pyrano[2,3-b]pyridine-6,7-dicarboxylate

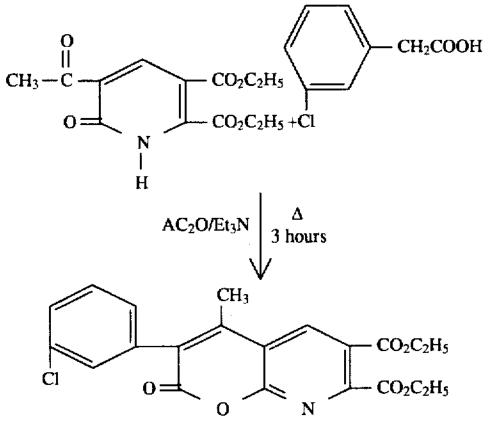

Diethyl 5-acetyl-1,6-dihydro-6-oxo-2,3-pyridinedicarboxylate (12.0 g, 0.043 mol), 3-chlorophenyl acetic acid (7.33 g, 0,043 mol) and triethylamine (6.52 g) are refluxed in 120 mL of acetic anhydride for three hours. The reaction mixture is cooled, poured into 120 mL of ice-cold water and made alkaline to pH 8 with an ammonium hydroxide solution. The crystalline solid is filtered and washed with water to give (17.0 g, 95%) of the product after drying. Recrystallization from ethyl acetate affords the pure product (13.29, 74% yield), melting point 170°–172° C.

EXAMPLE 27

Preparation of diethyl 5-[3-(dimethylamino)acryloyl]-1,6-dihydro-6-oxo-2,3-pyridinedicarboxylate

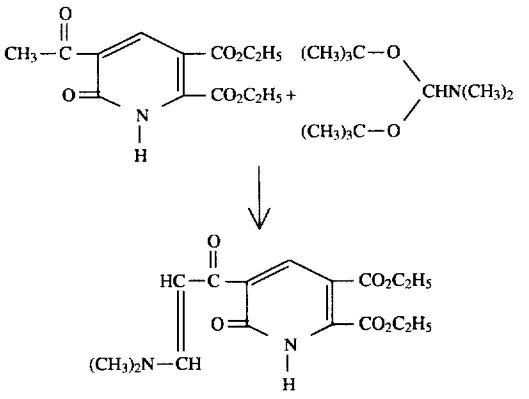

Diethyl 5-acetyl-1,6-dihydro-6-oxo-2,3-pyridinedicarboxylate, (25 g, 0,089 mol) and N,N-dimethylformamide dineopentyl acetal (50 mL, 98%, 40.62 g, 0.176 mol) are heated for 30 minutes at 80°–100° C. After cooling to room temperature, the product is obtained as a precipitate and is filtered and washed with hexane to yield 23.4 g, 70% yield, of solid which is recrystallized from isopropanol to give a pure product, melting point 182°–183° C.

EXAMPLE 28

Preparation of diethyl 4-oxo-4H-pyrano[2,3b-]pyridine6,7-dicarboxylate

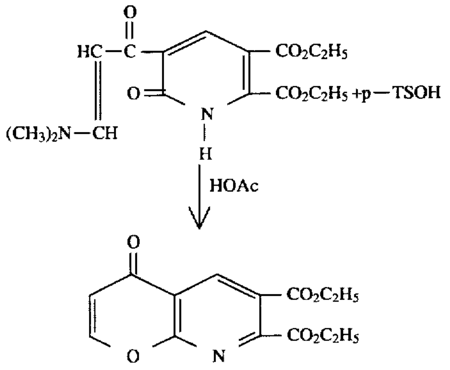

Diethyl 5-[3-(dimethylamino)acryloyl]-1,6-dihydro-6-oxo-2,3-pyridinedicarboxylate (6 g, 0.0178 mol). and p-toluenesulfonic acid (4.5 g, 0.021 tool) in acetic acid (60 mL) are heated at reflux for three hours. The mixture is then evaporated to dryness, neutralized with a saturated $NaHCO_3$ solution and extracted with methylene chloride. The organic solution is dried over $Na_2SO_4$, and concentrated to a thick oil, which solidifies after trituration with hexane-ether (4 g, 77%). The product is recrystallized from isopropanol to give a melting point 71°–72° C.

EXAMPLE 29

Preparation of diethyl 3,4-dihydro-4-hydroxy-2H-pyrano-2,3-b] pyridine-6,7-dicarboxylate and 3,4-dihydro-4-oxo-2H-pyrano[2,3-b] pyridine-6,7-dicarboxylate

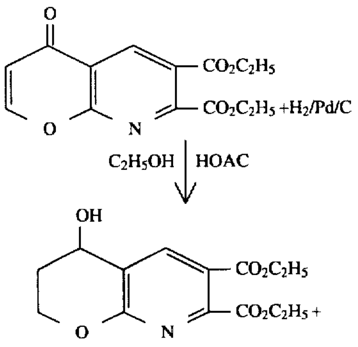

-continued

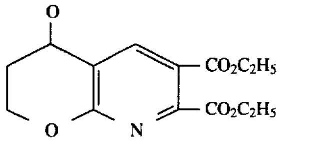

Diethyl 4-oxo-4H-pyrano[2,3-b]pyridine-6,7-dicarboxylate (8 g, 0.027 mol)and palladium on carbon (0.8 g, 10%) suspended in ethanol (250 mL) and acetic acid (25 mL) are shaken under 50 psi hydrogen in a Parr apparatus for 16 hours. The mixture is filtered and the filtrate evaporated to dryness. The residue is neutralized with a saturated $NaHCO_3$ solution and then extracted with methylene chloride and the methylene chloride solution dried over $Na_2SO_4$. Evaporation of the solvent gives the product mixture as an oil (8.34 g) which is purified by column chromatography to give the alcohol (4.4 g, 54%) and the ketone (2.4 g, 28%).

EXAMPLE 30

Preparation of diethyl 2H-pyrano[2,3-b]pyridine-6,7-dicarboxylate and diethyl 3,4-dihydro-2H-pyrano[2,3-b]-pyridine-6,7-dicarboxylate

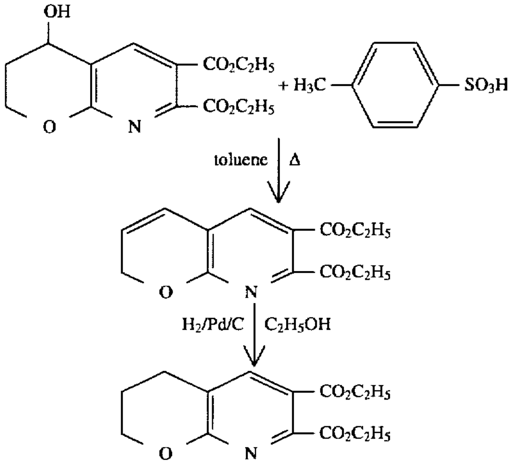

Diethyl 3,4-dihydro-4-hydroxy-2M-pyrano[2,3-b]-pyridine-6,7-dicarboxylate (4.4 g, 0.015 mol), and p-toluenesulfonic acid (3.5 g, 0.018 mol) in toluene 100 mL) are heated at 150° C. for one and one-half hours. The water formed is azeotropically distilled and collected in a Dean-Stark trap. After cooling to room temperature, the reaction mixture is evaporated to dryness and then neutralized with a saturated solution of $NaHCO_3$ and extracted with methylene chloride. The methylene chloride layer is dried over $Na_2SO_4$ and evaporated to give (2.71 g) oil (65%). The mass spectrum of this oil confirms the structure as 2H-pyrano[2,3-b]pyridine-6,7-dicarboxylic acid, diethyl ester.

The oil (2.71 g, 0.0098 mol) and Pd/C (10%, 0.27 g) suspended in ethanol (60 mL) and reacted with 50 psi hydrogen in a Parr apparatus for one and one-half hours. The mixture is filtered and the filtrate evaporated to give (2.34 g) of the desired product as a white solid, which has a melting point 66°–67° C.

EXAMPLE 31

Preparation of dimethyl 5-(2-chloroethyl)-6-chloro-2,3-pyridinedicarboxylate

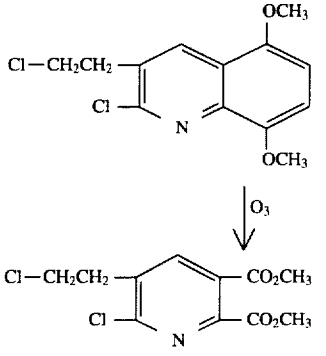

Ozone gas is bubbled into a solution containing 2-chloro-3-(2-chloroethyl )-5,8-dimethoxyquinidine (22.0 g); (O. Meth-Cohn, J. Chem. Soc., Perkin I, 1537–1543). trimethylorthoformate (80 mL) and $H_2SO_4$ (2 mL) in methanol (1.0 L) over five hours and 45 minutes. The mixture is concentrated under vacuum and the remaining oil dissolved in ether and washed with saturated sodium bicarbonate solution. The aqueous layer is extracted with additional ether. The combined ether extracts are washed with a 5% sodium bisulfite solution and then saturated sodium chloride solution. The organic layer is dried over anhydrous magnesium sulfate and concentrated under vacuum affording 16.5 g (71%) of dimethyl 5-(2-chloroethyl)-6-chloro-2,3-pyridinedicarboxylate as an orange oil.

EXAMPLE 32

Preparation of dimethyl 1-methyl-2,3-dihydro-1H-pyrrolo-2, 3-b]pyridine-5,6-dicarboxylate

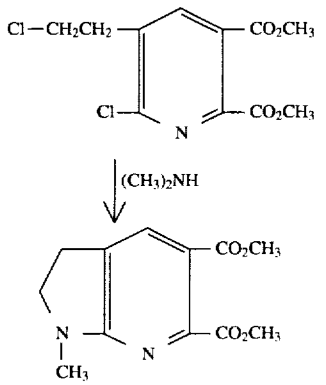

Dimethylamine (7.5 g, 166.6 mol) is bubbled into a solution of dimethyl 5-(2-chloroethyl)-6-chloro-2,3-pyridinedicarboxylate (20.0 g, 66mmol) in methanol (400 mL) over three hours. The resulting solution is stirred for 64 hours at room temperature and then four and one-half hours at reflux. After cooling the mixture is concentrated under vacuum and the crude product chromatographed on 250 g silica using 2:1 hexanes:ethyl acetate and then 1:1 hexanes-:ethyl acetate as eluant, affording 2.32 g (14%) of dimethyl 1-methyl-2,3-dihydro-1H-pyrrolo[2,3-b]pyridine-5,6-dicarboxylate, which is recrystallized from methylene chloride/hexanes, having a melting point 132°–133° C.

EXAMPLE 33

Preparation of dimethyl 1-methyl-1H-pyrrolo[2.3-b]pyridine-5,6-dicarboxylate

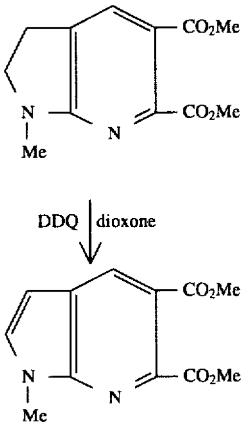

To a solution of 2.53 g (0,010 mol) dimethyl 2,3-dihydro-1-methyl-1H-pyrrolo[2,3-b]pyridine-5,6-dicarboxylate in 40 mL dioxane is added 2.64 g (0.011 mol) 2,3-dichloro-5,6-dicyano-1,4-benzoquinone. The resulting solution is stirred for 17 hours at 250° C. and for three hours at reflux. The dioxane is removed under vacumn and the residue is partitioned between 100 mL $CH_2Cl_2$ and 100 mL at $NaHCO_3$ and filtered. The layers are separated and the aqueous fraction is extracted with 2×75 mL $CH_2Cl_2$. The combined $CH_2Cl_2$ solutions are dried over $MgSO_4$ and are concentrated under vacuum. The crude product is chromatographed on 50 g silica using 2:1-hexanes:ethylacetate as eluant. Affords 1.90 g (75%) of dimethoxy-1-methyl-1H-pyrrolo[2,3-b]-pyridine-5,6-dicarboxylate as a yellow solid, mp 132°–133° C.

EXAMPLE 34

Preparation of triethyl-1,6-dihydro-6-oxo-2,3,5-pyridinetricarboxylate

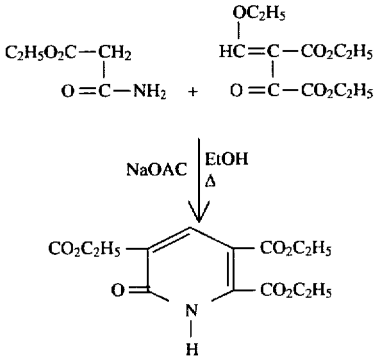

A solution of ethylmalonamate (23.6 g, 0.18 mol) in absolute ethanol (300 mL) is added to a stirred solution of diethyl ethoxymethyleneoxalacetate (44.0 g, 0.18 mol) in ethanol (200 mL) at 0° C., followed by the addition, of solid sodium acetate (14.72 g, 0.18 mol). After stirring for ten minutes at 0° C., the mixture is heated to reflux and stirred for 13.5 hours. After cooling, the ethanol is removed under vacuum, and the residue diluted with water and acidified to pH 2 with concentrated hydrochloric acid. The aqueous solution is extracted with methylene chloride (2×200 mL) and the organic layer washed with 300 mL saturated sodium chloride, then dried over anhydrous magnesium sulfate and concentrated in vacuum to give 45.0 g of the title product as an orange oil.

EXAMPLE 35

Preparation of triethyl 6-chloro-2,3,5-pyridine-tricarboxylate

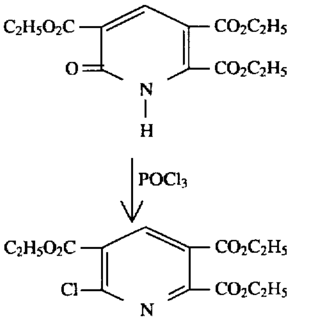

A solution of triethyl 1,6-dihydro-6-oxo-2,3,5-pyridine-tricarboxylate (39.7 g) in 300 mL of phosphorous oxychloride and 0.5 mL dimethylformamide is stirred at 100° C. for four hours and 15 minutes. After cooling, the excess phosphorous oxychloride is removed under vacuum. The residue is taken up in 200 mL methylene chloride and the solution poured into 500 mL of ice water and the layers are separated. The aqueous layer, made basic with concentrated ammonium hydroxide and ice, is extracted with 150 mL methylene chloride. The combined methylene chloride extracts are dried over magnesium sulfate, filtered and concentrated under vacuum, and the resulting crude product is chromatographed on silica using 5:1 hexanes:ethyl acetate and then 4:1 hexanes:ethyl acetate as eluants affording 26.5 g (47%) of the title product as an oil.

EXAMPLE 36

Preparation of tetraethyl 6-[(carboxymethyl)methylamino]2,3,5-pyridinerticarboxylate

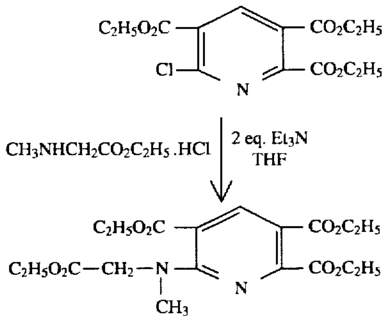

Sarcosine ethyl ester hydrochloride (13.91 g. 0.090 mol) is added to a stirred solution of triethyl 6-chloro-2,3,5-pyridinetricarboxylate (26.2 g, 0.075 mol) in tecrahydrofuran (THF, 200 mL) containing triethylamine (23 mL, 0.166 mol) at 0° C. The resulting solution is stirred for 24 hours at room temperature. The triethylamine hydrochloride is removed by filtration and is washed with 100 mL ether. The filtrate is concentrated under vacuum and the crude product chromatographed on silica using 4:1 hexanes:ethyl acetate as eluant affording 21.1 g (60%) of tetraethyl 6-[(carboxymethyl)methylamino]-2,3,5-pyridinetricarboxylate as a yellow oil.

EXAMPLE 37

Preparation of triethyl-3-hydroxy-1-methyl-1H-pyrrolo[2,3-b] pyridine-2,5,6-tricarboxylate

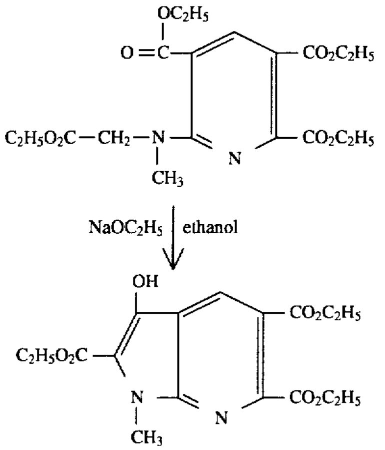

Tetraethyl-6-[(carboxymethyl)methylamino]-2,3.5-pyridinetricarboxylate (0.3 g, 0.73 mmol) in ethanol (10 mL) is added to a freshly prepared solution of sodium ethoxide (2.1 mmol) in ethanol at room temperature. The resulting orange solution is stirred for two hours at room temperature, then is poured into 200 mL water and the pH adjusted to 8 with saturated aqueous sodium bicarbonate. The aqueous solution is extracted with methylene chloride (3×100 mL). The combined methylene chloride extracts are dried over anhydrous magnesium sulfate, filtered and concentrated under reduced pressure, affording triethyl-3-hydroxy-1-methyl-1H-pyrrolo[2,3-b]pyridine-2,5,6-tricarboxylate (0.28 g, 100%), which upon recrystallization from methylene chloride/hexanes has a melting point 129°–130° C.

EXAMPLE 38

Preparation of diethyl 3-methyl-1H-pyrrolo[2,3-b]pyridine-5,6-dicarboxylate

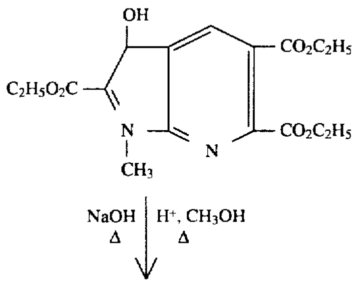

-continued

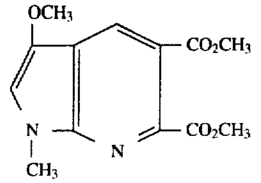

A solution of triethyl 3-hydroxy-1-methyl-1H-pyrrolo[2,3-b]pyridine-2,5,6-tricarboxylate (9.2 g, 0.025 mol) in 75 mL 2N sodium hydroxide is heated at 60° C. for 21 hours. After cooling to 0° C., the reaction mixture is acidified to pH 3 with concentrated hydrochloric acid. The majority of the water is removed by azeotropic distillation with toluene and the remaining solution (25 mL) is diluted with 300 mL) methanol. To this solution is added (3 mL) concentrated sulfuric acid and the resulting solution is heated for 64 hours at reflux. After cooling, the reaction mixture is concentrated under vacuum and the residue partitioned between aqueous sodium bicarbonate (500 mL, 5%) and methylene chloride (300 mL). The layers are separated and the aqueous solution is extracted with additional (200 mL) methylene chloride.

The combined organic extracts are washed with 200 mL saturated sodium chloride solution, dried over anhydrous magnesium sulfate and concentrated under vacuum. The crude product is chromatographed on silica using 2:1 hexanes-ethyl acetate as an eluant, affording 2.04 g (29%) of diethyl 3-methoxy-1-methyl-1H-pyrrolo[2,3-b]pyrrolo-[2,3-b]pyridine-5,6-dicarboxylate, mp 73°–74° C.

EXAMPLE 39

Preparation of diethyl 5-acetyl-1,6-dihydro-6-oxo-2,3-pyridinedicarboxylate, 5-oxime

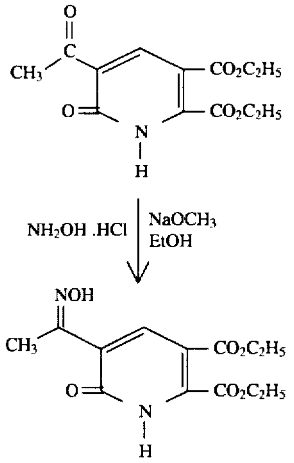

Hydroxylamine hydrochloride (4.94 g, 0.0711 mol) and sodium methoxide (7.68 g, 0.1422 mol) are added to a solution of diethyl 5-acetyl-1,6-dihydro-6-oxo-2,3-pyridinedicarboxylate (20.00 g, 0.0711 mol) dissolved in absolute ethanol (450 mL) under an $N_2$ atmosphere. The reaction mixture is heated to reflux for 40 minutes and is then stirred at room temperature overnight. The mixture is then acidified to pH 4–5 with glacial acetic acid and diluted with water (200 mL). The removal of the ethanol in vacuo results in the precipitation of an off-white solid, which is collected by filtration, washed with water, and air dried to give diethyl 5-acetyl-1,6-dihydro-6-oxo-2,3-pyridinedicarboxylate, 5-oxime, melting point 140°–142° C.

EXAMPLE 40

Preparation of diethyl 5-acetamido-1,6-dihydro-6-oxo-2,3-pyridinedicarboxylate and diethyl 2-methyloxazolo-5,4-b]-pyridine-5,6-dicarboxylate

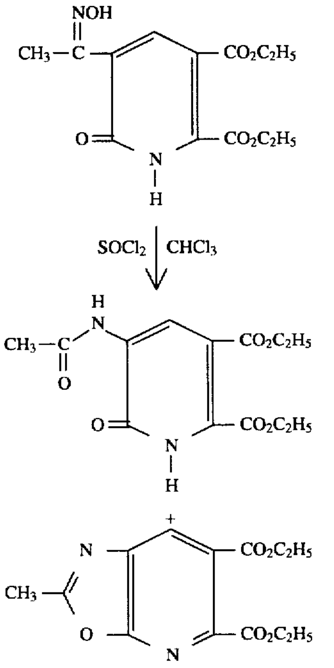

Thionyl chloride (35.5 mL, 0.486 mol) and three drops of N,N-dimethylformamide are added to a solution of diethyl 5-acetyl-1,6-dihydro-6-oxo-2,3-pyridinedicarboxylate, 5-oxime (47.99 g, 0.162 mol) dissolved in chloroform (800 mL) under an $N_2$ atmosphere. The reaction is stirred at room temperature for one hour, then stirred at room temperature overnight.

The solution is concentrated in vacuo and the residue partitioned between methylene chloride and water. The two phase system is neutralized with 2M sodium hydroxide solution and the aqueous layer separated and extracted with methylene chloride. The combined organic solutions are dried over anhydrous sodium sulfate, concentrated in vacuo and chromatographed over silica gel with 1–30%/ethyl acetate in methylene chloride to give diethyl 5-acetamido-1,6-dihydro-6-oxo-2,3-pyridinedicarboxylate in 58% yield, which upon crystallization from methylene chloride/hexane has melting point 149°–151° C.

The fractions enriched with the 2-methyloxazolopyridine are chromatographed over silica gel with hexane/ethyl acetate (3:1) eluant. Recrystallization of the product from methylene chloride/hexane gives diethyl 2-methyloxazolo [5,4-b]pyridine-5,6-dicarboxylate as pale yellow crystals in 17% yield having a melting point 101°–103° C.

EXAMPLE 41

Preparation of diethyl 5-amino-1,6-dihydro-6-oxo-2,3-pyridinedicarboxylate

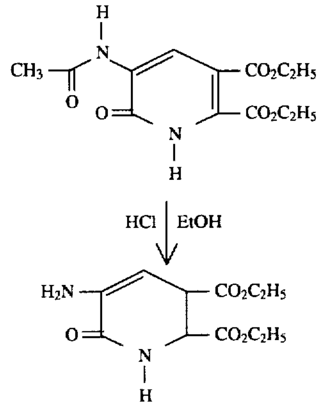

Hydrogen chloride gas is bubbled into a solution of diethyl 5-acetamido-1,6-dihydro-6-oxo-2,3-pyridinedicarboxylate (5.2 g, 0.018 tool) dissolved in absolute ethanol (400 mL) until the solution is saturated at 20° C. The reaction is stirred at room temperature overnight and is then concentrated in vacuo. The resulting residue is dissolved in water, neutralized with solid sodium bicarbonate, and extracted into methylene chloride. The combined organic extracts are dried over anhydrous sodium sulfate, filtered and concentrated in vacuo to give diethyl 5-amino-1,6-dihydro-6-oxo-2,3-pyridinedicarboxylate as a yellow solid in quantitative yield.

EXAMPLE 42

Preparation of diethyl 2-ethyloxazolo[5,4-b]pyridine-5,6-dicarboxylate

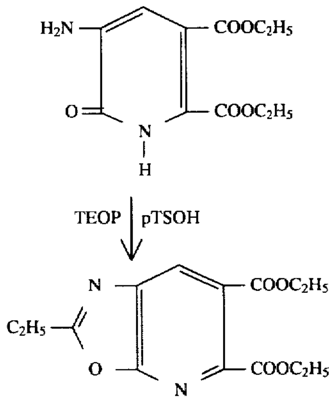

Diethyl 5-amino-1,6-dihydro-6-oxo-pyridine-2,3-dicarboxylate (7.57 g, 0.030 tool ), is suspended in 60 mL triethylorthopropionate (TEOP 0.30 mol). A small amount of p-toluenesulfonic acid is added and the mixture is heated at reflux for 65 hours. The triethylorthopropionate is removed in vacuo and the resulting oil is purified by column chromatography. The tractions containing the pure desired product are combined and stripped to a honey-colored oil weighing 7.38 g, yield 84.8%.

EXAMPLE 43

Preparation of 2-methyloxazole[5,4-b]pyridine-5.6-dicarboxylic acid

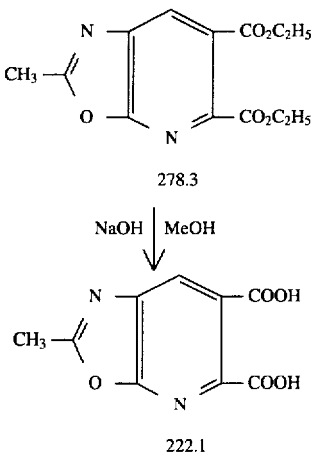

To a solution of diethyl 2-methyloxazolo[5.4-pyridine-5, 6-dicarboxylate (5.42 g, 0.0195 mol) dissolved in absolute methanol (160 mL) is added a 10% aqueous sodium hydroxide solution (36.1 mL, 0.0974 mol). A white precipitate slowly forms. The reaction is stirred at room temperature for one hour, diluted with water (20 mL) to dissolve the precipitate, and concentrated in vacuo The residue is dissolved in water and acidified to pH 2–3 with concentrated HCl. The resulting white precipitate is collected by filtration, washed with water, and air dried to give 2-methyloxazolo[5,4-b] pyridine-5,6-dicarboxylic acid in 61% yield, melting point 235°–236° C. (dec).

EXAMPLE 44

Preparation of 2-methyloxazolo[5,4-b]pyridine-5,6-dicarboxylic anhydride

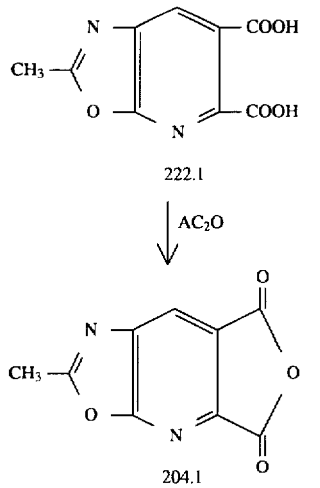

A suspension of 2-methyloxazolo[5,4-b]pyridine-5,6-dicarboxylic acid (4.84 g, 0.0218 tool) in acetic anhydride (150 mL) is slowly heated to 70° C. at which point all the solids dissolve forming a yellow solution. The reaction mixture is heated at 70° C. overnight, cooled to room temperature, and concentrated in vacuo. Xylene is added to remove excess acetic anhydride by codistillation. 2-Methyloxazolo[5,4-b]pyridine-5,6-dicarboxylic anhydride is obtained as a pale yellow solid in 97% yield melting point 194°–196° C.

EXAMPLE 45

Preparation of 2-methyloxazolo[5,4-b]pyridine-5.6-dicarboxylic acid-6-diamide

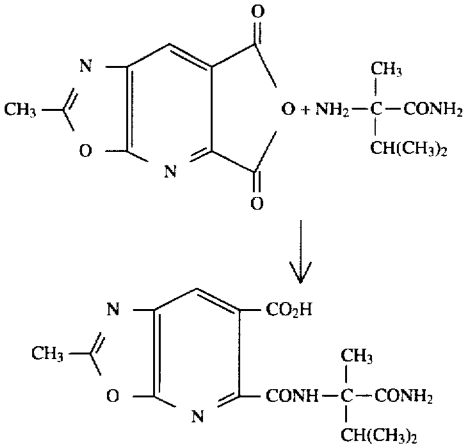

The anhydride (4.33 g) is dissolved in 150 mL of acetonitrile and the solution cooled in an ice bath and 3.03 g of the aminoamide is added. A white precipitate forms immediately. The reaction mixture is warmed to room temperature and allowed to-stir overnight. The solid product is removed by filtration, washed with acetonitrile, and dried in a vacuum oven, giving 6.3 g, 89%, mp 193°–196° C.

In a manner similar to the above other acid diamides and acid amide thioamides are prepared and appear in Table II below.

TABLE II

[1-Carbamoyl-1,2-dimethylpropyl)carbamoyl heteropyridine carboxylic acids

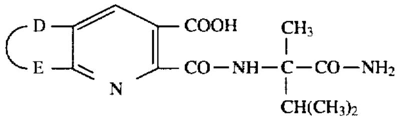

| Heteropyridine | mp°C. |
| --- | --- |
| 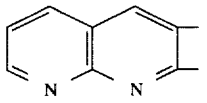 | — |
| 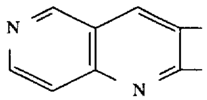 | — |

TABLE II-continued
[1-Carbamoyl-1,2-dimethylpropyl)carbamoyl heteropyridine carboxylic acids
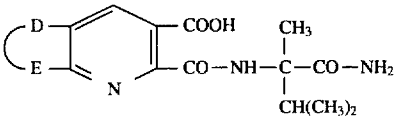
| Heteropyridine | mp°C. |
|---|---|
| 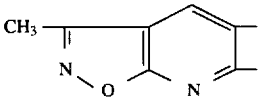 | 124–30 |
| 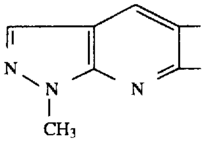 | — |
| 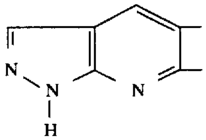 | — |
| 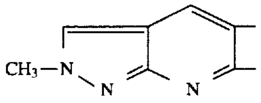 | — |
| 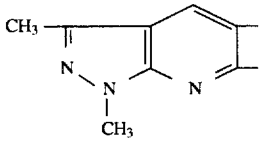 | — |
| 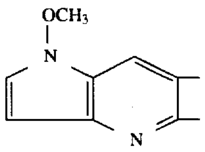 | — |
| 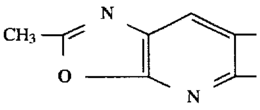 | 193–196 |
| 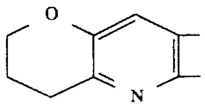 | — |
| 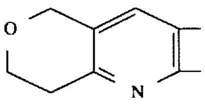 | — |
| 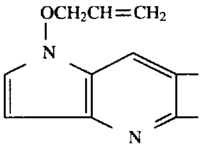 | — |
TABLE II-continued
[1-Carbamoyl-1,2-dimethylpropyl)carbamoyl heteropyridine carboxylic acids
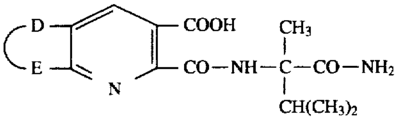
| Heteropyridine | mp°C. |
|---|---|
| 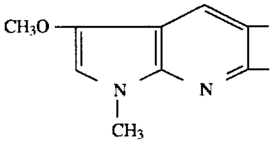 | — |
| 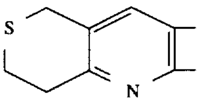 | 116 |
| 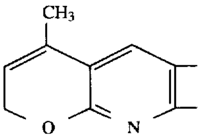 | — |
| 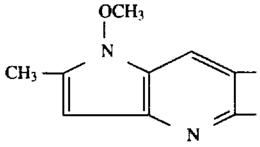 | — |
| 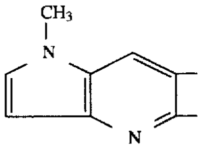 | — |
| 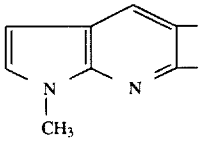 | — |
| 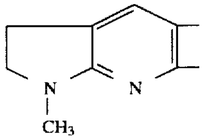 | — |
| 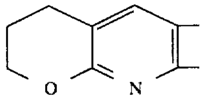 | 193–195 |
| 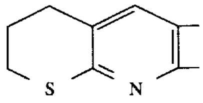 | 188–190 (dec) |

TABLE II-continued
[1-Carbamoyl-1,2-dimethylpropyl)carbamoyl heteropyridine carboxylic acids
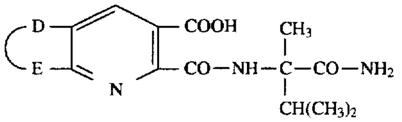
| Heteropyridine | mp°C. |
| --- | --- |
| 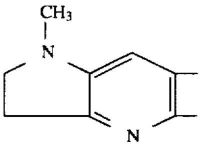 | — |
| 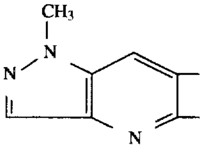 | — |
| 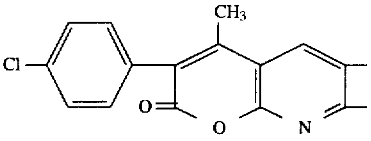 | — |
| 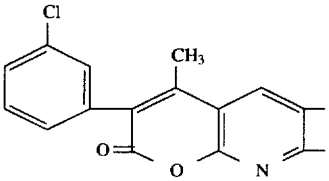 | — |
| 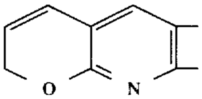 | 138–141 |
| 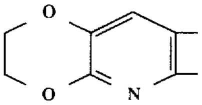 | 118–121 |
| 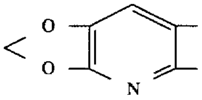 | 72–75 |
| 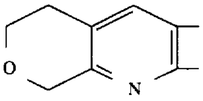 | — |
| 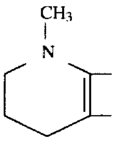 | — |
| 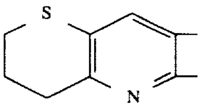 | 192–193 |
TABLE II-continued
[1-Carbamoyl-1,2-dimethylpropyl)carbamoyl heteropyridine carboxylic acids
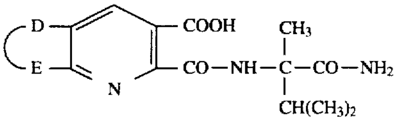
| Heteropyridine | mp°C. |
| --- | --- |
| 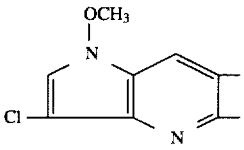 | — |
| 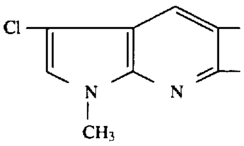 | — |
| 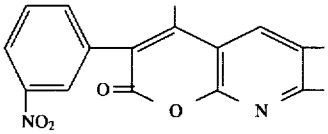 | — |
| 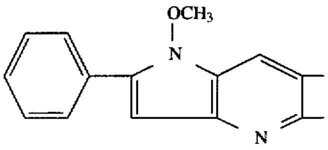 | — |
| 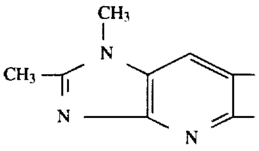 | — |
| 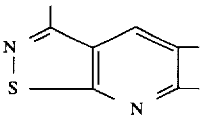 | — |
| 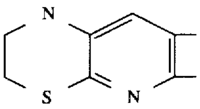 | — |
| 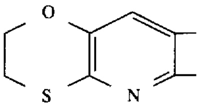 | — |
| 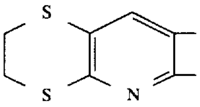 | — |

TABLE II-continued

[1-Carbamoyl-1,2-dimethylpropyl)carbamoyl heteropyridine carboxylic acids

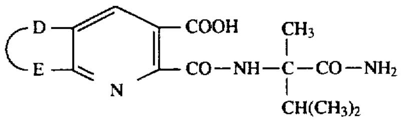

| Heteropyridine | mp°C. |
| --- | --- |
| 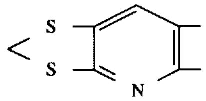 | — |
| 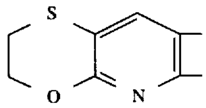 | — |
| 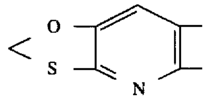 | — |

EXAMPLE 46

Preparation of diethyl 1,6-dihydro-5-hydroxy-6-oxo-2,3-pyridinedicarboxylate

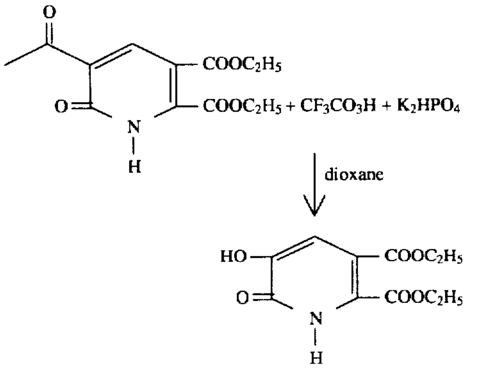

A solution of trifluoroperacetic acid is prepared by dropwise addition of trifluoroacetic acid (154 mL, 1.09 mol) into a 500 mL dioxane solution containing 96 mL (0.94 mol) of 30% $H_2O_2$ at 0° C. under $N_2$ atmosphere.

2,3-Pyridinedicarboxylic acid, 5-acetyl-1,6-dihydro-6-oxo, diethyl ester (43.81 g, 0.156 mol) and $K_2HPO_4$ (124.81 g, 0.716 mol) dissolved in 500 mL dioxane in a three week reaction flask are added dropwise the above trifluoroperacetic and solution under $N_2$ atmosphere. The suspension is heated to 95° C. for 20 hours.

The mixture is filtered to isolate the inorganic salts. Evaporation of the filtrate gives an oil (35.84 g, 90%). NMR indicated about 90% pure of the desired product: MS, m/e =255.

EXAMPLE 47

Preparation of diethyl 1,4-dioxino[2,3-b]pyridine-6,7-dicarboxylate

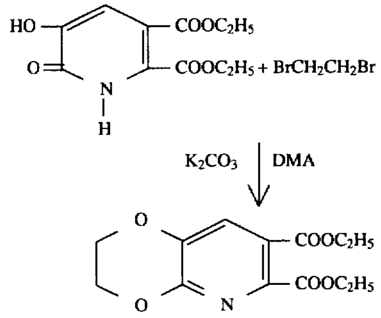

A mixture of 2,3-pyridinedicarboxylic acid, 1,6-dihydro-5-hydroxy-6-oxo-, diethyl ester (17.55 g, 0.069 mol) and K2$CO_3$ (10.4 g, 0.075 mol) suspended in 100 mL of N,N'-dimethylacetamide (DMA) is heated to 100° C. under $N_2$ atmosphere. They 1,2-dibromoethane (14.2 g, 0.076 mol) in 20 mL DHA is added dropwise into the suspension. The resulting mixture is heated to 170° C. for 20 hours.

After cooling to room temperature, the mixture is filtered to remove the insoluble salts. The filtrate is vacuum distilled over the residue is extracted with EtOAc. Evaporation of the EtOAc solution give 8.74 g of dark oil. Mass spectrum of this oil indicates it contains about 50% of the desired product. The pure compound is obtained by liquid column chromatography. MS, m/e=281. Yield of the desired product based on the starting material, 21%.

EXAMPLE 48

Preparation of diethyl 1,3-dioxolo[4,5-b]pyridine-5,6-dicarboxylate

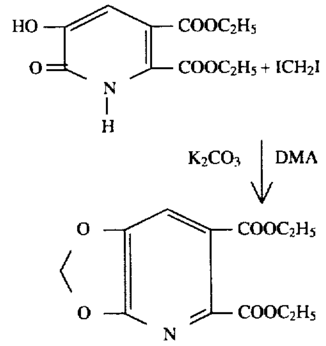

A mixture of 2,3-pyridinedicarboxylic acid, 1,6-dihydro-5-hydroxy-6-oxo-, diethyl ester (7.85 g, 0.031 mol) and $K_2CO_3$ (4.7 g, 0.034 mol) suspended in 80 mL DMA is heated to 100° C. under $N_2$ atmosphere. Then diiodomethane (8.5 g, 0.032 mol) in 20 mL DMA is added dropwise into the suspension. The resulting mixture is heated to 140° C. for 20 hours. The mixture is filtered to remove insoluble salts. The filtrate is vacuum distilled and the residue dissolved in $CH_2Cl_2$. The $CH_2Cl_2$ solution is passed through a thin column of silica-gel and celite. Evaporation of $CH_2Cl_2$ gives a light brown oil (1.83 g). Mass spectrum of this oil suggests it contains about 33% of the desired product. The pure compound is obtained by liquid column chromatography. MS, m/e, 267.

EXAMPLE 49

Preparation of diethyl 7,8-dihydro-5H-pyrano[4,3-b]pyridine-2,3-dicarboxylate

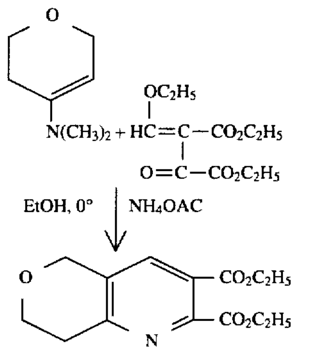

A solution of diethyl ethoxymethyleneoxalacetate (2.33 g, 0.00954 mol) dissolved in absolute ethanol.(40 mL) is added dropwise to a cooled (5° C.) solution of 3,6-dihydro-N,N-dimethyl-2H-pyrano-4-amine (Hellberg, L. H., Juarez, A. Tet. Lett.., 3553 (1974)) (1.00 g, 0.00786 mol) dissolved in ethanol (15 mL). The reaction is stirred at 5° C. for 30 minutes, treated with ammonium acetate (1.80 g 0.0233 mol), and stirred overnight at room temperature. The ethanol is removed in vacuo, and the residue is partitioned between methylene chloride and water. The separated aqueous layer is extracted with methylene chloride. The combined organic solutions are dried over anhydrous sodium sulfate, concentrated in vacuo, and chromatographed over silica gel with hexane/ethyl acetate (3:1) as eluant, to give diethyl 7,8-dihydro-5H-pyrano[4,3-b]pyridine-2.3-dicarboxylate as a yellow oil in 72% yield.

EXAMPLE 50

Preparation of diethyl 7,8-dihydro-5H-thiopyrano[4.3-b]-pyridine-2,3-dicarboxylate

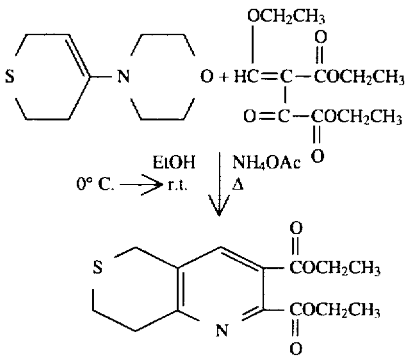

Diethyl ethoxymethylene oxalacetate (6.50 g. 1.5 eq) is slowly added (ten minutes) to a solution of 4-(3,6-dihydro-4H-thiopyran-3-yl)-morpholine (Verhoever et al., Tetrahetron Lit; 209, 1977), (3.25 g, 1 eq) in 30 mL absolute ethanol at 0° C. (ice bath). The mixture is magnetically stirred for one hour, whereupon ammonium acetate (3.75 g, 3 eq) is added and the mixture is heated at reflux and stirred for an additional three hours. The solution is cooled and the solvent removed in vacuo. The viscons red syrup is flash chromatographed eluting with hexanes and gradually increasing the eluant polarity to 15% ethyl acetate/hexanes. The crystalline compound is recrystallized (ether/heptanes) to afford 3.30 g (63%) of white crystals, mp 65°–66° C.

EXAMPLE 51

Preparation of ethyl 2-formyl-7,8-dihydro-5H-pyrano[4,3-b] pyridine-3-carboxylate

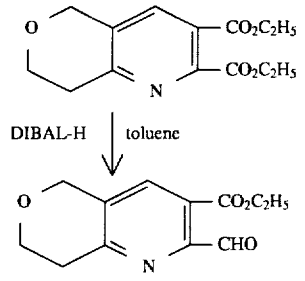

The diester (2.8 g) is dissolved in 100 mL toluene and chilled to −70° C. under a nitrogen atmosphere. Diisobutylaluminum hydride (DIBAL-H), (16 mL, 1 molar solution in toluene) is added dropwise over two hours and then additional acetic acid, water and ether are added. A white solvent is removed by filtration and the filtrate concentrated in vacuo to yield an orange oil which is redissolved in methylene chloride, washed with brine, magnesium sulfate, filtered and the solvent removed to give the product as an oil.

Flash chromatography on silica gel using 1:1 hexanes ether give the aldehyde ester in 30% yield.

EXAMPLE 52

Preparation of ethyl 4-amino-1-methyl-2-pyrrolecarboxylate

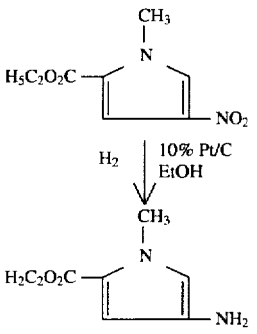

Ethyl 1-methyl-4-nitro-2-pyrrolecarboxylate (16.0 g, 0,081 mol) (M. J. Weiss, J. S. Webb and J. M. Smith, J. Amer. Chem. Soc., 79, 1266 (1957)) is dissolved in (200 mL) ethanol and (1.60 g) of 10% platinum on carbon is then added. The mixture is shaken for 16 hours in a PARR hydrogenator. The catalyst is removed by filtration through a pad of celite and the filtrate is concentrated in vacuo to a yellow oil. The oil is carried on directly without purification.

EXAMPLE 53

Preparation of 5-ethyl, dimethyl [(5-carboxy-1-methylpyrrol-3-yl)amino]maleate

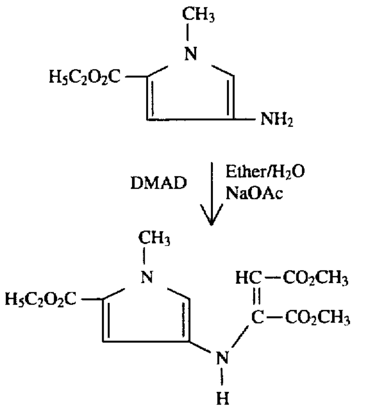

Unpurified ethyl 4-amino-1-methyl-2-pyrrolecarboxylate (0.081 mol) is added to (50 mL) anhydrous ether and (50 mL) water and the mixture cooled to 0° C. Dimethyl acetylenedicarboxylate (DMAD, 10.95 mL, 0.089 mol) is dissolved in 25 mL anhydrous ether and added dropwise to the stirred mixture so that the reaction temperature remains below 15° C. After stirring cold for five minutes, sodium acetate is then added in portions until the pH of the aqueous layer is 9. The two-phase red mixture is then allowed to warm to room temperature and stirred for 15 hours. The layers are separated, and the ethereal layer concentrated in vacuo to give the product as a red oil which is carried on without purification.

EXAMPLE 54

Preparation of 2-ethyl dimethyl 1-methylpyrrolo[3.2-b]pyridine-2,5,6-carboxylate

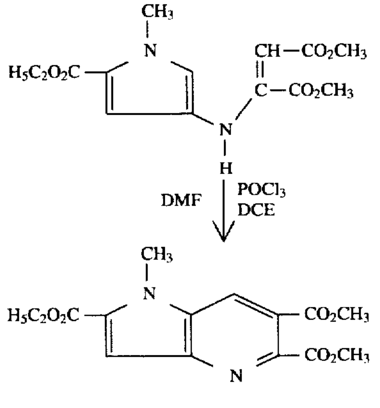

Dimethylformamide (0.089 mol) is dissolved in 100 mL dichloroethane and cooled to 0° C. in an acetone/ice bath. Phosphorous oxychloride (0.089 mol, 8.3 mL) is added dropwise over five minutes. The clear colorless solution is allowed to warm slowly to room temperature, whereupon it gradually turns yellow. Unpurified 5-ethyl dimethyl-[(5-carboxy-1-methylpyrrol-3-yl)amine]maleate (0.081 mol) is dissolved in 50 mL dichloroethane and added dropwise to the cooled reagent so that the reaction temperature remains below 5° C. The mixture is allowed to warm to room temperature and is then stirred for six hours. The solution is quenched with ice and the resulting layers separated. The organic layer is concentrated in vacuo to a brown solid which is recrystallized from ethyl acetate, yielding 21.3 g (82.1%) of the tan solid product, having a melting point 161.5°–163° C.

EXAMPLE 55

Preparation of diethyl 6-methyl-5-nitro-2,3-pyridinedicarboxylate

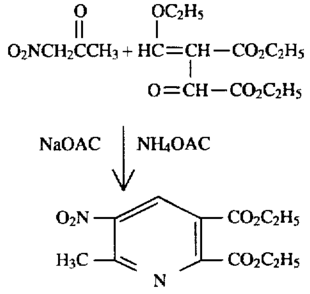

Diethyl ethoxymethyleneoxalacetate (150.4 g, 0.616 mol, 1 eq) is dissolved in 300 mL absolute ethanol under a nitrogen atmosphere and the mixture is cooled to −10° C. in an ice/acetone bath. Unpurified 1-nitro-2-propanone (prepared by the method of D. Baker and S. Putt, Synthesis, 1978, 478-9, assumed to be 63.448 g, 0.616 mol) dissolved in 100 mL absolute ethanol is then added to the stirred solution. Sodium acetate (101.06 g, 1,232 mol) is then added in portions so that the temperature of the reaction remains below 10° C., followed by the addition of ammonium acetate (94.6 g, 1,232 g). The reaction mixture is allowed to warm to room temperature and is then stirred for 16 hours. The mixture is filtered through two pads of silica gel which are then eluted with methylene chloride. The filtrate is concentrated in vacuo to a thick dark oil which is chromatographed using hexanes as eluant, yielding the product in an 18.2% yield (31.4 g), having a melting point 90°–91.5° C.

EXAMPLE 56

Preparation of diethyl 6-[2-(dimethylamino)vinyl]-5-nitro-2,3-pyridinedicarboxylate

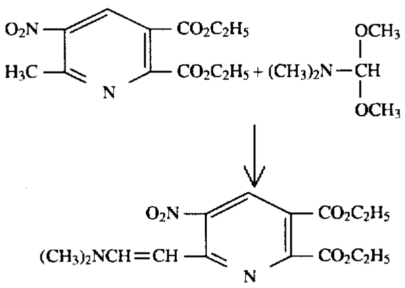

N,N-Dimethylformamide dimethylacetal (18.38 mL. 0.138 mol) is mixed with diethyl 6-methyl-5-nitro-2.3-pyridinedicarboxylate (30.0 g, 0.106 tool). The solid mixture is heated to 55° C. for two hours and the resulting red soltuion is then cooled to room temperature. The solid, which forms upon cooling, is treated with anhydrous ether and the product collected by filtration in 94% yield, having a melting point 128°–129.5° C.

Similarly, diethyl 6-[2-(dimethylamino)propenyl]-5-nitro-2,3-pyridinedicarboxylate, having a melting point 112°–113.5° C., is prepared in 93% yield from N,N-dimethylacetamide dimethylacetal and diethyl 6-methyl-5-nitro-2,3-pyridinedicarboxylate.

Diethyl 6-[2-(dimethylamino)styryl]-5-nitro-2,3-pyridinedicarboxylate is also prepared, using the above method, from N,N-dimethylbenzamide diethyl acetal and diethyl 6-methyl-5-nitro-2,3-pyridinedicarboxylate. A modification in the procedure of the latter is that upon cooling the dark red solution is partitioned between ether and water. The ethereal layer is separated and concentrated in vacuo to a dark red oil, which was carried on without purification.

EXAMPLE 57

Preparation of diethyl 1-hydroxypyrrolo[3,2-b]pyridine-2,3-dicarboxylate

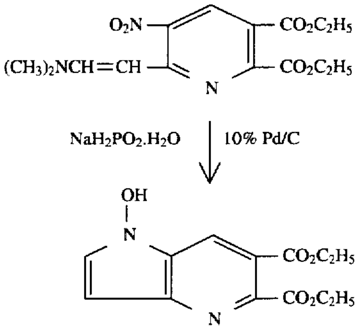

Diethyl 6-[2-(dimethylamino)vinyl]-5-nitro-2,3-pyridinedicarboxylate (30.9 g, 0,092 tool) is dissolved in (500 mL) tetrahydrofuran under nitrogen and 3.1 g of 10% palladium on carbon is added all at once to the red solution. Sodium hypophosphite (121.00 g, 1.375 mol) dissolved in water is then added dropwise to the solution over three hours and hydrogen gas evolution is noted during this time. Ether (500 mL) is added to the pale yellow reaction mixture and the two phase mixture is filtered through a pad of celite. The ethereal layer is separated and concentrated in vacuo to give the product as a pale yellow solid in 987° yield, having a melting point 154°–158° C.

Similarly, diethyl 1-hydroxy-2-methylpyrrolo[3,2-b]pyridine-5,6-dicarboxylate is prepared in 95% yield, having a melting point 178°–179.5° C., from 6-[2(dimethylamino-)propenyl]-5-nitro-2,3-pyridinedicarboxylate.

Diethyl 1-hydroxy-2-phenylpyrrolo[3,2-b]pyridine-5,6-dicarboxylate, having a melting point of 179°–182.5° C., is also prepared from 6-[2-(dimethylamino)styryl]-5-nitro-2,3-pyridinedicarboxylate using the above procedure. The pale yellow solid product is purified by chromatography and recrystallized from ethyl acetate.

EXAMPLE 58

Preparation of diethyl 1-methoxypyrrolo[3,2-b]pyridine-5,6-dicarboxylate and diethyl 1-methylpyrrolo[3,2-b]pyridine-5,6-dicarboxylate

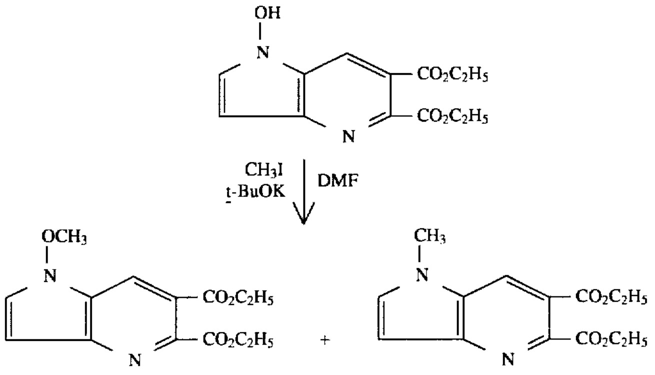

Diethyl 1-hydroxypyrrolo[3,2-b]pyridine-5,6-dicarboxylate (25.2 g, 0.091 mol) is dissolved in 100 mL dimethylformamide and, the solution cooled to 0° C. under nitrogen. Potassium t-butoxide (20.42 g, 0.182 mol) is added over 15 minutes so that the reaction temperature is no higher than 15° C. The red solution is stirred for 15 minutes and methyl iodide (11.33 mL, 0.182 mol) is then added dropwise over 15 minutes, so that the reaction temperature is no higher than 15° C. The mixture is allowed to warm to room temperature then stirred for 16 hours. The resulting suspension is filtered and the mother liquors concentrated in vacuo. The resulting oil is partitioned between ethyl acetate and water (pH 8), and the organic layer separated and concentrated in vacuo. The resulting yellow oil, containing a mixture of diethyl 1-methoxypyrrolo[3,2-b]pyridine-5,6-dicarboxylate, is chromatographed using 9:1 hexane/ethyl acetate and increasing the polarity to 2:1 hexane/ethyl acetate. The fractions containing the methoxy product (confirmed by NMR) are combined and concentrated in vacuo to give 53.2% yield of a pale yellow solid, melting point 87.5°–89° C. The fractions containing the methyl product are combined and concentrated in vacuo to give 23.8% yield of a tan solid, melting point 97°–100° C.

EXAMPLE 59

Preparation of diethyl 1-methoxy-2-phenylpyrrolo[3.2-b]-pyridine-5,6-dicarboxylate

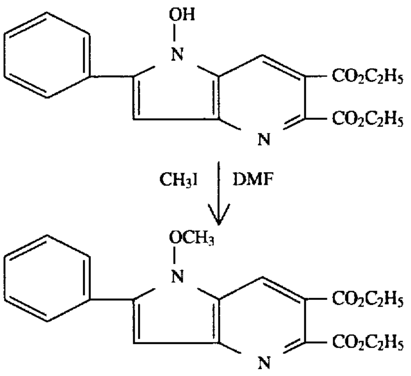

1-Hydroxy-2-phenylpyrrolo[3,2-b]pyridine-5,6-dicarboxylate (1.3 g, 0.0037 mol), is dissolved in 50 mL dimethylformamide and cooled to −30° C. under nitrogen. Potassium t-butoxide (0.85 g, 0.007 mol) is added over ten minutes so that the reaction temperature is no higher than −24° C. The red solution is stirred for five minutes and methyl iodide (0.87 mL, 0.014 mol) is then added dropwise over five minutes so that the reaction temperature is no higher than −20° C. The mixture is then allowed to warm to room temperature and stir for 16 hours. The suspension is concentrated in vacuo. The resulting oil is partitioned between ethyl acetate and water (pH 8). The organic layer is separated and concentrated in vacuo The resulting yellow oily solid is flash chromatograpbed using 9:1 hexane/ethyl acetate. The product is obtained as a pale yellow solid weighing 1.0 g (73.5% yield) having a melting point 95°–96.5° C.

Similarly, diethyl 1-methoxy-2-methylpyrrolo[3,2-b]pyridine-5,6-dicarboxylate is prepared from diethyl 1-hydroxy-2-methylpyrrolo[3,2-b]pyridine-5,6-dicarboxylate in 95% yield having melting point 94.5°–96.5° C.

EXAMPLE 60

Preparation of diethyl 1-(allyloxy)pyrrolo[3,2-b]pyridine-5,6-dicarboxylate

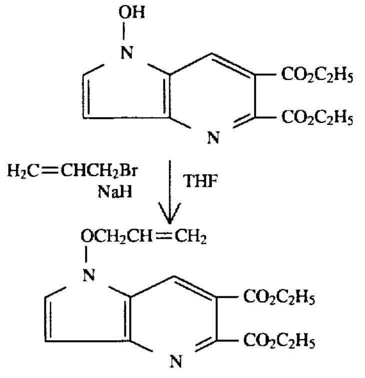

Diethyl 1-hydroxypyrrolo[3,2-b]pyridine-5,6-dicarboxylate (6.2 g, 0.022 mol) is dissolved in (200 mL) dry tetrahydrofuran and cooled to 0° C. under nitrogen. Sodium hydride (0.77 g, 0.033 mol) is added in portions over ten minutes and the reaction is stirred for 30 minutes at 0° C. Allyl bromide (2.01 mL, 0.024 mol) is added all at once to the suspension and the mixture allowed to warm to room temperature and then stirred for 16 hours. The mixture is filtered and the filtrate concentrated in vacuo. The resulting oil is chromatographed using 4:1 hexanes/ethyl acetate and then increasing the polarity to 2:1 hexanes/ethyl acetate to give the product as a yellow oil in 89% yield.

EXAMPLE 61

Preparation of diethyl 1-(difluoromethoxy)pyrrolo[3.2-b]-pyridine-5,6-dicarboxylate and diethyl pyrrolo[3,2-b]-pyridine-5,6-dicarboxylate

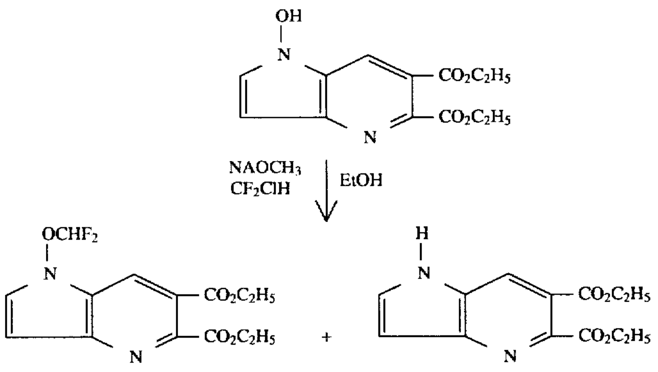

Sodium methoxide (8.1 g, 0.15 g) is added slowly over 15 minutes to diethyl 1-hydroxypyrrolo[3,2-b]pyridine-5,6-dicarboxylate (6.94 g, 0.025 mol), suspended under nitrogen in 100 mL absolute ethanol at 0° C. The mixture is then heated to reflux and Freon 22 gas is bubbled through the reaction suspension for six hours. Additional sodium methoxide (8.1 g, 0.15 mol), is added in portions at reflux and the Freon addition stopped after a total of eight hours. The reflux is continued for 16 hours. Additional sodium methoxide (8.1 g, 0.15 mol ) is added and Freon 22 gas is again bubbled through the suspension for six hours at reflux.

The Freon gas addition is then stopped and the mixture is heated for 72 hours at reflux. The mixture is cooled to room temperature and ethanolic HCl added until a pH 4–5 is achieved. The solid suspension is filtered and the filtrate concentrated in vacuo to a yellow oil which is chromatographed using 4:1 hexane/ethyl acetate, to give the title product as a yellow oil, 16.2% yield. The major side product collected is diethyl pyrrolo[3,2-b]pyridine-5,6-dicarboxylate in 52% yield as a pale yellow solid, having a melting point 109°–111° C.

EXAMPLE 62

Preparation of diethyl 1-methoxy-3-chloropyrrolo[3.2-b]-pyridine-5,6-dicarboxylate

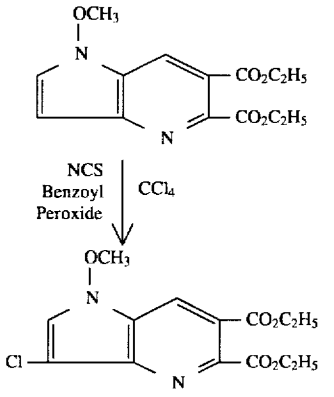

Benzoyl peroxide (0.91 g, 0.037 mol) is added to diethyl 1-methoxypyrrolo[3,2-b]pyridine-5,6-dicarboxylate (1.0 g, 0.003 mol) dissolved in (40 mL) carbon tetrachloride under a nitrogen atmosphere and the suspension stirred for ten minutes. N-Chlorosuccinimide (0.84 g, 0.0063 mol) is then added and the reaction heated at 60° C. for four hours. The mixtue is cooled to room temperature and the inorganics are removed by filtration. The organic mother liquors are washed with water and sodium bisulfate and concentrated in vacuo to an orange oil. The oil is flash chromatographed using hexanes and then 4:1 hexanes/ethyl acetate, giving the title product as an off-white solid in 51% yield, having a melting point 146°–148° C.

The ethereal mother liquors are concentrated in vacuo and dissolved in (100 mL) acetic acid. Palladium on carbon (0.44 g, 5%) is added and the mixture is shaken for 16 hours under 50 psi hydrogen in a part hydrogenator. The reaciton is stopped and the dark solution is filtered through a pad of celite and concentrated in vacuo. The resulting oil is chromatographed using 7:1 hexane/ethyl acetate and then 3:1 hexane/ethyl acetate, to give the title product as a pale yellow solid in 31% yield, having a melting point 109°–111° C.

EXAMPLE 63

Preparation of diethyl pyrrolo[3,2-b]pyridine-5,6-dicarboxylate

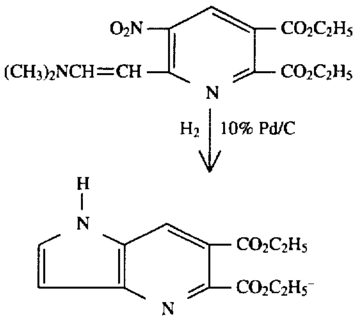

Diethyl 6-[2-(dimethylamino)vinyl]-5-nitro-2,3-pyridinedicarboxylate (20.0 g, 0.059 mol) is partially dissolved in 200 mL acetic acid and then (0.6 g) 5% palladium on carbon is added all at once. The mixture is shaken for 16 hours under psi hydrogen in a Parr hydrogenator. The reaction is stopped and the suspension is diluted with ethanol and filtered through a pad of celite. The mother liquors are concentrated in vacuo to a dark red oil. Trituration with ether gives the N-hydroxy compound as a white solid in 40% yield, having a melting point 154°–158° C.

The ethereal mother liquors are concentrated in vacuo and dissolved in 100 mL acetic acid. Palladium on carbon (0.44 g, 5%) is added and the entire mixture is shaken for 16 hours in a Parr hydrogenator. The reaction is stopped and the dark solution is filtered through a pad of celite and concentrated in vacuo. The resulting oil is gravity chromatographed using 7:1 hexane/ethyl acetate and increasing in polarity to 3:1 hexane/ethyl acetate. A pale yellow solid is collected. Yield: 31%, melting point 109°–111° C.

EXAMPLE 64

Preparation of dimethoxy 3-chloro-1-methyl-1H-pyrrolo[2,3-b] pyridine-5,6-dicarboxylate

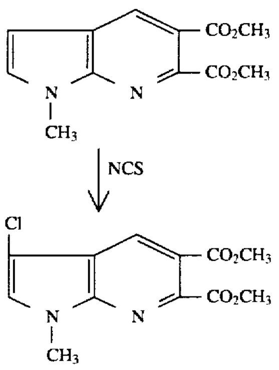

To a solution of (1.74 g, 0.0070 mol) dimethoxy methyl-1H-pyrrolo[2,3-b]pyridine-5,6-dicarboxylate in 50 mL $CCl_4$ is added a mixture of 0.98 g (0.0073 mol) N-chlorosuccinimide and 0.18 g (0.00073 mol) benzoyl peroxide. The resulting solution is stirred for four hours at reflux and 15 hours at 60° C. The solution is cooled to room temperature, diluted with 100 mL $CH_2Cl_2$ and washed with 5%

$NA_2S_2O_5$. The aqueous layer is extracted with an additional 50 mL $CH_2Cl_2$ and the combined organic solutions are dried over $MgSO_4$ and concentrated under vacuum. The crude product is chromatographed on 50 g silica using 3:1 hexanes:ethyl acetate as eluant to afford 0.87 g (44%) of dimethoxy-3-chloro-1-methyl-1H-pyrrolo[2,3-b]pyridine-5,6-dicarboxylate as a yellow solid, mp 129°–137° C.

EXAMPLE 65

Preparation of 1B-pyrazolo[3,4-b]quinoline

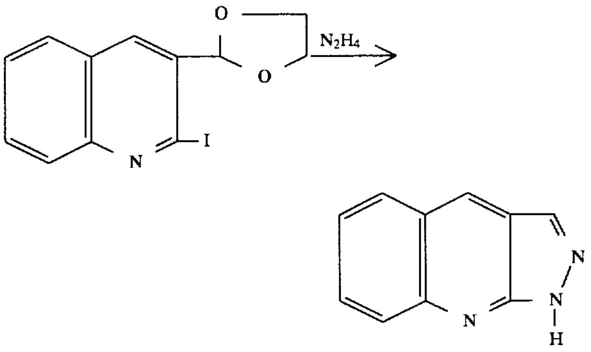

Hydrazine hydrate (10 g, 0.20 mol) is added dropwise to a suspension of 2-iodoquinoline-3-carboxaldehyde ethylene ketal (65.5 g, 0.20tool), (O. Meth-Cohn, J. Chem. Soc., Perkin I, 2509 (1981), m.p. 104.5°–106.5° C. in methanol (250 mL) containing triethylamine 28 mL) at reflux. After refluxing overnight additional hdyrazine hydrate (10 g) is added and the mixture is stirred at reflux for another six and one-half hours. Concentrated hydrochloric acid (75 mL) is then added dropwise, while the mixture is refluxing and the reaction continued for one hour. The reaction mixture is cooled, poured onto ice and allowed to stand for two days. A red solid is removed by filtration and the filtrate is concentrated by rotary evaporation to remove methanol. The remaining solution is adjusted to pH 9 with concentrated ammonium hydroxide and the cream colored precipitate is filtered, washed with water and air dried. Recrystallization from ethanol gives an analytical sample, melting point 207°–208° C., calcd. for $C_{10}H_7N_3$: C, 70.99; H, 4.17; N, 24.84. Found: C, 70.82: H. 4.06; N, 24.18.

EXAMPLE 66

Preparation of
1H-pyrazolo[3,4-b]pyridine-2,3-dicarboxylic acid

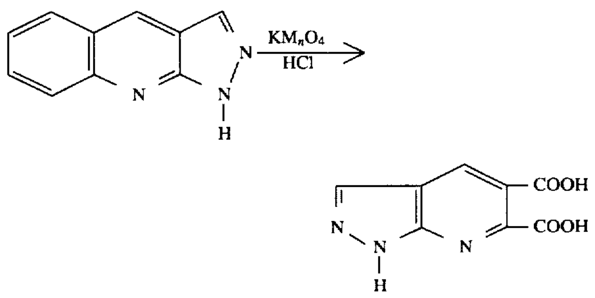

Crude 1H-pyrazolo[3,4-b]quinoline is suspended in water (300 mL) and heated to 60° C. The heat source is removed and a total of 100 g of potassium permanganate (0.64 mol) is added in portions so as to maintain the reaction temperature below 72° C. Additional water (100 mL) is added after addition of one-half of the permangate. Upon completion of the addition the mixture begins to cool, and it is heated to 100° C. for 25 minutes, then cooled to room temperature. The mixture is filtered through celite, and the solids washed with hot water (100 mL). The filtrate is acidified to pH 2 with concentrated hydrochloric acid and the resulting solution is concentrated on the rotary evaporator to 75 mL, and chilled in an ice bath. The solids which precipitate are filtered off and dried in an oven at 50° C. overnight, giving 11 g. Recrystallization from 95% ethanol gives the pure product having mp 270°–285° C. (slow dec).

EXAMPLE 67

Preparation of diethyl
1H-pyrazolo[3,4-b]pyridine-5,6-dicarboxylate

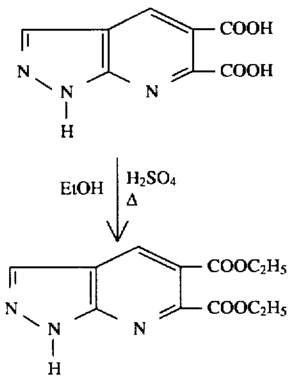

A suspension of 1H-pyrazolo[3,4-b]pyridine-5,6-dicarboxylic acid (62 g) in 500 mL of an ethanol sulfuric acid mixture (10:1 by weight) is heated at reflux for 16 hours. The suspension is cooled and filtered and the filtrate concentrated in vacuo. Column chromatography using hexanes/ethyl acetate (4:1 ) elution gives 4.0 g of the title product as an oil.

EXAMPLE 68

Preparation of diethyl
1-methyl-1H-pyrazolo[3,4-b]pyridine-5,6-dicarboxylate
and diethyl
2-methyl-2H-pyrazolo-3,4-b]pyridine-5,6-dicarboxylate

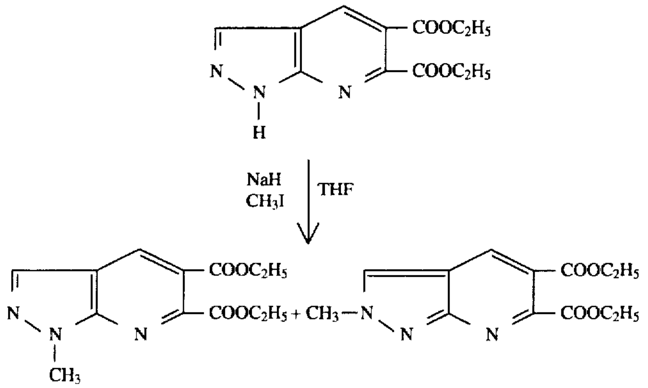

To a solution of diethyl 1H-pyrazolo[3,4-b]pyridine-5,6-dicarboxylate (4.0 g, 0.015 mol) in THF (50 mL) at 5° C. is added a NaH (0.70 g of 60%, 0.018 mol) dispersion in mineral oil. The mixture is stirred for ten minutes and then methyl iodide (2.84 g, 0.020 mol) is added. The mixture is stirred overnight at room temperature, then concentrated in vacuo to give a crude mixture of the isomers which are separated by column chromatography (hexanes/ethyl acetate (4:1) elution), affording 1.2 g (28.5%) of 1H-pyrazolo[3,4-b]pyridine-5,6-dicarboxylate as the faster eluting product, and 2.6 g (61.8%) of the 2H-pyrazolo[3,4-b]pyridine-5,6-dicarboxylate as the slower eluting product as oils.

EXAMPLE 69

Preparation of 3-hydroxytetrahydropyran

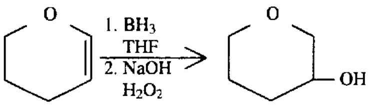

To 33.6 (0.4 mol) of $\Delta^2$-dihydropyran in 240 mL of tetrahydrofuran is added 140 mL of 1.0M solution of borane in tetrahydrofuran (0.015 equiv. of hydride) at 0° to 5° C. The reaction mixture is stirred at this temperature for three hours and then warmed to 25° C. and stirred for an additional two hours. The organic borane is oxidized at 40° to 45° C. by adding 72 mL of 3N sodium hydroxide solution followed by dropwise addition of 48 mL of 30% hydrogen peroxide. After the reaction mixture is stirred for one to two hours at room temperature, a saturated sodium chloride solution is added and the phases are separated. The aqueous phase is extracted with 5×100 mL portions of ether and the combined organic layers are dried over anhydrous sodium sulfate. The solvent is removed under reduced pressure giving the product as a colorless oil, 38.3 g, yield 92.5% which when analyzed by gas chromatography gives a single peak, bp 40°–50° C.

EXAMPLE 70

Preparation of tetrahydropyranone-3

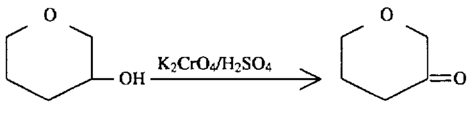

Jones reagent is prepared by adding in portions 74.2 g (0.249 mol) of potassium dichromate dihydrate to a cooled solution of 87.10 g (0.88 mol) of concentrated sulfuric acid in 125 mL of water. This reagent is added dropwise to a cold solution (ice-bath) of (38.28 g, 0.375 mol) 3-hydroxytetrahydropyran, in 125 mL of ether over a period of three hours. The mixture is stirred for three hours at 0° C., after which another 125 mL of ether is added and the mixture is warmed to room temperature and stirred overnight. Ice cold water 100 mL is added and the layers are separated. The aqueous layer is extracted with 4×100 mL portions of ether, the organic phases are combined and dried over anhydrous magnesium sulfate. The solvent is removed under reduced pressure giving the product as a light yellow oil, 26.37 g, 70% yield.

EXAMPLE 71

Preparation of morpholine, 4-(3,4-dihydro-2H-pyran-5-yl)

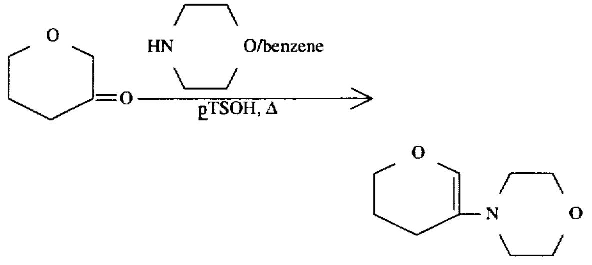

Tetrahydropyranone-3, (25.38 g, 0,253 mol) is refluxed in 75 mL of benzene overnight with 33..0 g (0.38 mol, 1.5 equiv.) of morpholine and a catalytic amount of p-toluene sulfonic acid until the theoretical amount of water (4.7 mL) is separated within a Dean-Stark trap. The benzene is removed on a rotary flash evaporator and the product isolated as a clear red oil in 95% yield.

EXAMPLE 72

Preparation of 2H-pyrano[3,2-b]pyridine-6,7-dicarboxylic acid, 3,4-dihydro-diethyl ester

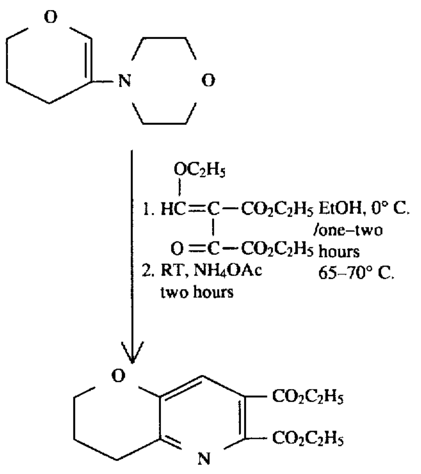

An ethanol solution solution (100 mL) containing diethyl ethoxymethylene oxalacetate (50.2 g, 0.205 mol) is added to a stirred ethanol (200 mL) solution containing the enamine (23.2 g, 0.137 mol) prepared in Example 53 at 0° C. and the mixture stirred for two hours. The reaction mixture is allowed to warm to room temperature and ammonium acetate (42.2 g) is added. After stirring overnight at room temperature, additional ammonium acetate (21.1 g) is added and the mixture is heated at 70° C. for two hours and is then allowed to cool to room temperature. Water (250 mL) is added and the resulting mixture extracted with methylene chloride (5×150 mL). The organic layer is separated, dried over anhydrous $Na_2SO_4$, filtered and the solvent removed under reduced pressure. The resulting oily residue is purified by column chromatography on silica gel with a methylene chloride ethyl acetate mixture (99:1) as the eluant to give the title product as a yellow oil in 17% yield.

EXAMPLE 73

Preparation of diethyl-7,8-dihydro-6H-thiopyrano[3,2-b] pyridine-2,3-dicarboxylate

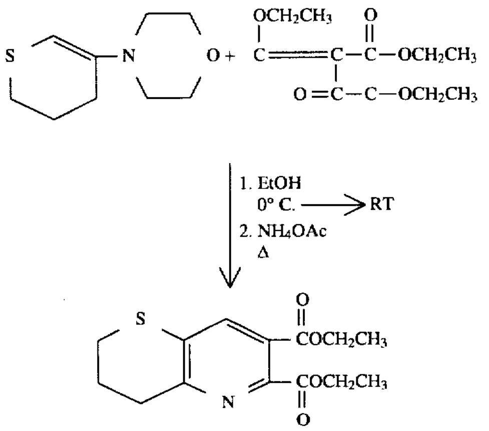

Diethyl ethoxymethylene oxalacetate (28.9 g, 1.1 equiv.) is added slowly, over ten minutes to a solution of 4-(5,6-dihydro-4H-thiopyran-3-yl)morpholine (Hirsh and Wang, *Syn Comm.* 12, 333 (1982) (assumed quantitative yield of morpholino enamine; 0.107 tool; one equiv.) in 300 mL of absolute ethanol cooled to 0° C. (ice bath). The mixture is stirred for one hour whereupon ammonium acetate (21.5 g: 3 equiv.) is added and the mixture heated at reflux and stirred an additional three hours. The mixture is cooled and the solvent removed in vacuo. The red syrup is flash chromatographed eluting with hexanes and gradually increasing eluant polarity to 15% ethyl acetate/hexanes to give 7.81 g (25%) of a clear yellow oil.

EXAMPLE 74

Preparation of methyl 2-aminopyrazine,3-carboxylate

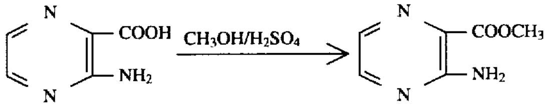

3-Aminopyrazine-2-carboxylic acid (55.5 g, 0.4 mol) is suspended in 400 mL of methanol, cooled in an ice bath and concentrated sulfuric acid (80 mL) is gradually added with stirring and stirring then continued for 48 hours at room temperature. The resulting dark brown solution is poured into 700 mL of water containing sodium bicarbonate (160 g). The brown crystalline solid which precipitates is collected and dried. The crude product is purified by recrystallization from water to yield the product as yellow needles in 63% yield, melting point 169°-170° C.

EXAMPLE 75

Preparation of pyrazine methanol, 3-amino

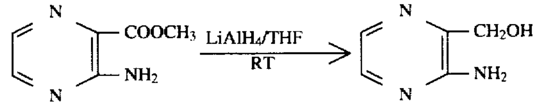

Lithium aluminum hydride (2.4 g, 0.003 mol) is added in increments to a stirred suspension of methyl 3-aminopyrazine-2-carboxylate (9.0 g, 0.059 mol) in 600 mL of tetrahydrofuran, in a 2 liter 4-neck flask fitted with a $N_2$-inlet tube, thermometer, and a condenser over a period of 30 minutes. After the reaction mixture is stirred at room temperature for an additional hour, water 20 mL is added with caution and the solids which form are filtered off. The filtrate is dried over anhydrous sodium sulphate, and filtered. The solvent is removed under reduced pressure, giving a yellow semi-solid residue, 6.5 g, 88% yield. A portion of this solid is extracted with methylene chloride, which gives a crystalline solid, melting point 112°-119° C.

EXAMPLE 76

Preparation of 3-aminopyrazinecarboxaldehyde

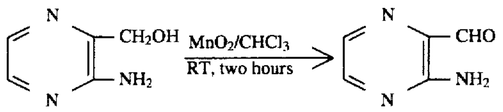

A suspension of 3-aminopyrazine methanol, 6.3 g (0.05 mol) and manganese dioxide (38.0 g) in 400 mL of chloroform is stirred at room temperature for two hours and the resulting solid is filtered off. The filtrate is evaporated to dryness which gives the desired product as a yellow crystalline solid, (5.00g, 82% yield) having a melting point 110°-114° C.

EXAMPLE 77

Pyrido[2,3-b]pyrazine-6,7-dicarboxylic acid, diethyl ester

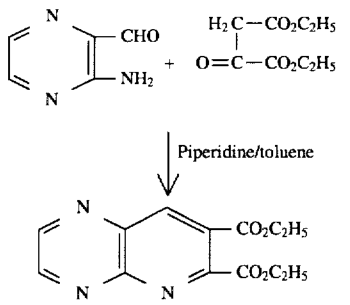

Diethyl oxalacetate, (4.7 g, 0.025 mol) and piperidine (1.66 g, 1.93 mL) are added to 3-aminopyrazine-2-carboxaldehyde (2.4 g, 0.0195 tool ) dissolved in 250 mL of toluene. After the reaction mixture is refluxed for two hours, the toluene is removed under reduced pressure to give a dark red oily residue. The product is purified by column chromatography on silica gel (hexane:EtOAc, 4:1), affording 3.1 g (58% yield), of the crude desired product. Crystallization from ether-hexane (4:1) gives analytically pure compound 1.5 g (28%) having a melting point 83°-85° C.

EXAMPLE 78

Preparation of 4-pentynyl methanesulfonate

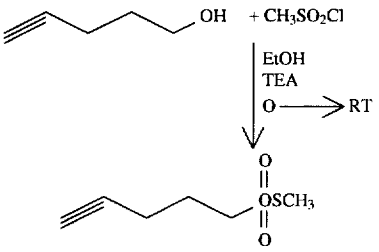

To pentyne-4-ol (Farchan Chemical Co) (42.0 g: 0.5 mols) in 500 mL ether at -5° C. (dry ice bath) is added in a rapid dropwise fashion triethylamine (104.8 mL; 0.75 mols) diluted with 100 mL ether. While maintaining the temperature at or below 15° C. throughout, methane sulfonyl chloride, (94.2 mL; 0.70 mols) diluted with 100 mL ether, is added dropwise over 45 minutes. The thick suspension is stirred an additional 30 minutes, after which the precipitate is filtered. The filter cake is washed with ether and the combined ether layers washed twice with water, then once with brine. The ether layer is then dried over anhydrous magnesium sulfate and solvent removed under reduced pressure to yield the product as a pale yellow oil; yield 64 g (79%), which is used in the next step without further purification.

A small sample is purified by bulb-to-bulb distillation, boiling point 70°-85° C., 0.15 mm Hg).

EXAMPLE 79

Preparation of S-(4-pentynyl )thiosemicarbazide, 1:1 salt with methanesulfonic acid

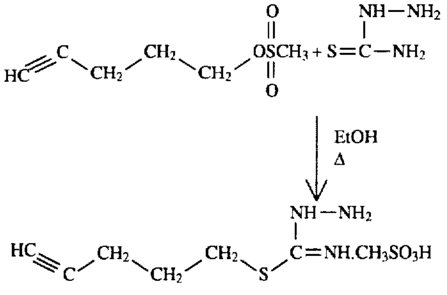

Thiosemicarbazide (27.3 g; 0.3 mols) is suspended in 200 mL ethanol and brought to reflux. Crude 4-pentynylmethanesulfonate (51.0 g; 0.32 mols), diluted with 50 mL ethanol, is added dropwise to the suspension over 40 minutes. The solids all dissolve after a few hours and refluxing it continued for 48 hours. Removal of solvent under reduced pressure yields the product as a thick amber oil which is washed three times with hot ether. The crude product is used in the next step without further purification.

EXAMPLE 80

Preparation of dimethyl 2,3-dioxosuccinate

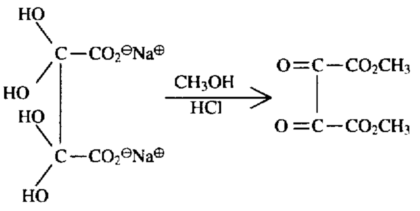

A suspension of 250 g of 2,3-dihydroxytartaric acid, disodium salt hydrate (Aldrich) in one liter of methanol is saturated at 0 to 10° C. with gaseous HCl and allowed to stand for one week at 5° C. Solids are removed by filtration and the solvent is then removed to give a thick yellow oil. Vacuum distillation of the oil gives the desired product boiling point 92°-101° C., 2.3-2.5 mm, suitable for use in the following steps.

EXAMPLE 81

Preparation of dimethyl 2H-dihydrothiopyrano[2,3-b]pyridine-6,7-dicarboxylate

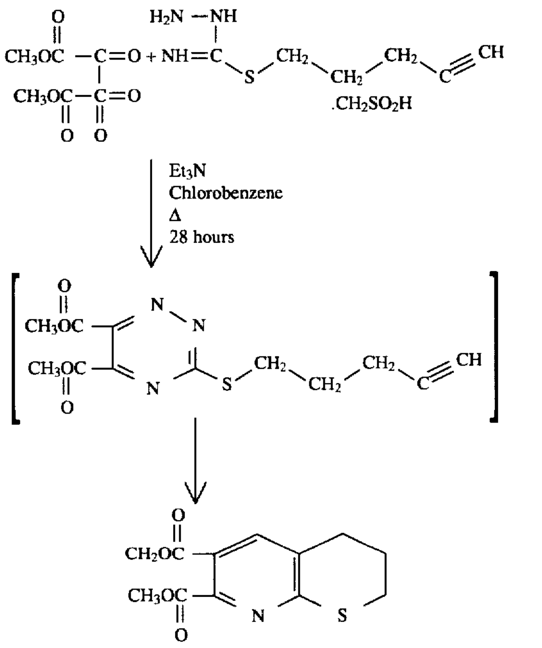

A mixture of S-(4-pentynyl)thiosemicarbazide methanesulfonic acid salt (25.0 g; 0.1 mols) in chlorobenzene (175 mL) is cooled to −5° C. in an ice-acetone bath under a nitrogen purge. Triethylamine (14.0 mL; 0.1 mol) in chlorobenzene (25 mL) is added dropwise over 30 minutes and the mixture is stirred another 20 minutes. A solution of dimethyl 2,3-dioxosuccinate (26.0 g; 0.1 tools, assuming 65% purity) in chlorobenzene (50 mL) is added dropwise over 30 minutes, causing most of the thick oil to dissolve. The ice bath is removed and the solution is brought to reflux. After refluxing for 28 hours, the solution is cooled, and solids removed by filtration. The filtrate is concentrated under reduced pressure and the residue partitioned between water and ethyl acetate. The water layer is washed with fresh ethyl acetate, and the combined organics are washed with saturated NaCl and dried over $MgSO_4$. The solvent is removed under reduced pressure, and the residual oil chromatographed (waters prep 500 HPLC; 3% ethyl acetate in methylene chloride). The fractions containing the desired product are combined and solvent is removed under reduced pressure. The product is obtained as a light beige solid (7.5 g) which is recrystallized from 2-propanol to obtain a crystalline off-white solid (6.4 g), homogeneous by TLC mp=82°–85° C.

EXAMPLE 82

Preparation of 6-(4-isopropyl-4-methyl-5-oxo-2-imidazolin-2-yl)-1H-1-methyl-pyrazolo-[3,4-b]pyridine-5-carboxylic acid

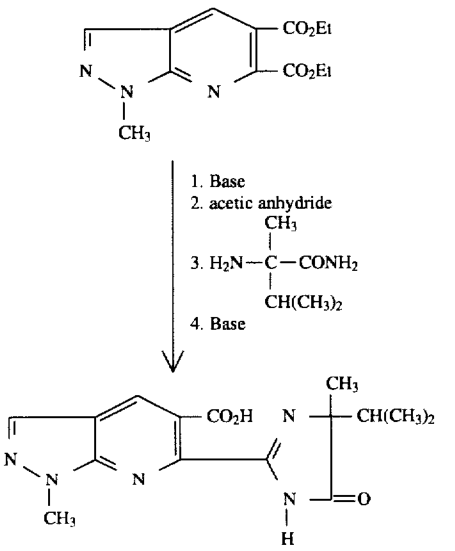

Diethyl-1-methyl-1H-pyrazolo[3,4-b]pyridine-5,6-dicarboxylate (24 g) in 200 mL of 1:1 ethanol-water is heated at reflux overnight, then concentrated on a rotary evaporator. The residue is acidified to pH 1 with 6N HCl, cooled and filtered to remove the solid diacid product, which is then washed with cold water and air dried. The yielde is (32%) of crude diacid mp 228°–229° C. (dec).

The diacid (9.g) in acetic anhydride (40 mL) is stirred at 85°–90° C. for two hours. The reaction mixture is filtered while hot and the filtrate is concentrated under reduced pressure to yield the crude anhydride as a gum. The product is dissolved in tetrahydrofuran (50 mL), 2-amino-2,3-dimethylbutyramide is then added and the mixture is stirred while heating to 40° C. for one andone-half hours and then at reflux for 16 hours. Upon completion of the reaction, the mixture is cooled to room temperature and concentrated in vacuo. The residue is dissolved in aqueous NaOH (10 g/100 mL), 100 mL) and the resulting solution is stirred at 75°–85° C. for four hours. After cooling to room temperature the reaction mixture is cooled to 10° C. and acidified to pH 2 with concentrated hydrochloric acid.

The resulting precipitate is collected by filtration, dried and purified by column chromatography on silica gel utilizing ethyl acetate-ethanol on the eluant to give the title product as a tan solid having a melting point 239°–243° C.

EXAMPLE 83

Preparation of 7-(4-isopropyl-4-methyl-5-oxo-2-imidazolin-2-yl)-4H-2,3-dihydro-4-methylpyrano[2,3-b]pyridine-6-carboxylic acid

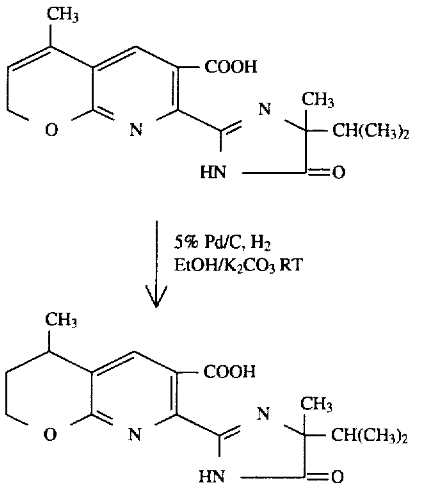

The crude 2H-pyranopyridine imidazoline carboxylic acid is suspended in 10 mL of water and to this suspension is added 10 mL of 15% aqueous potassium carbonate solution. The material dissolves to give a clear yellow-brown solution. Ethanol, 95% (40 mL) is added to the solution slowly, so that the layers do not separate. 5%/Pd/C, 100 mg is added to this solution and the mixture is agitated on a Parr hydrogenator overnight. The mixture was filtered and evaporated to dryness. The residue is taken in 50 mL of water and washed with 2×25 mL portions of methylene chloride which are discarded. The aqueous layer is made acidic with concentrated HCl to pH 1 while cooling in an ice bath and extracted with 5×50 mL portions of methylene chloride.

The combined methylene chloride extracts are dried over anhydrous sodium sulfate, filtered and the solvent is removed under reduced pressure. This gives the product as shiny, slightly, yellowish fluffy said, mp 95°–99° C.

Utilizing the procedure of Example 43, 44, 45, 82 and 83, and substituting the appropriate fused heteropyridine dicarboxylic acid and amino amide or amino thiomide yields the (imidazolin-2-yl)fused heteropyridine compounds listed in Table III below.

TABLE III (Imidazolin-2-yl)fused heteropyridine carboxylic acids

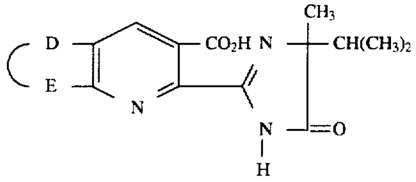

| Fused heteropyridine | mp°C. |
|---|---|
| 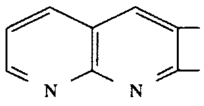 | 223.0–224.0 |
| 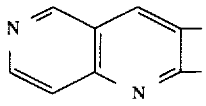 | 247.0–250.0 |
| 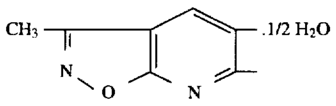 | 226.0–227.0 |
| 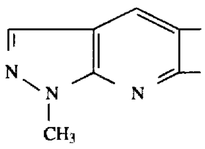 | 239.0–243.0 |
| 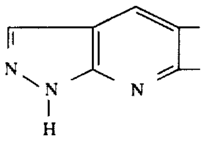 | 180.0–185.0 |
| 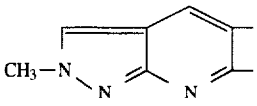 | 282.0–283.0 |
| 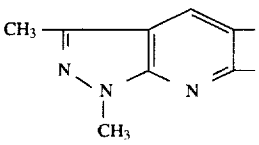 | >350 |
| 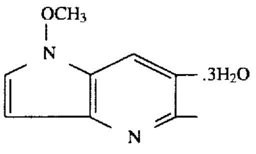 | 170.0–173.0 |
| 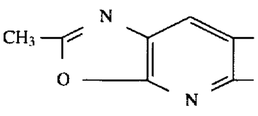 | 236.0–239.0 |
| 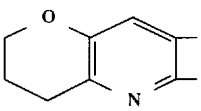 | 199.0–201.0 |

TABLE III-continued
(Imidazolin-2-yl)fused heteropyridine carboxylic acids
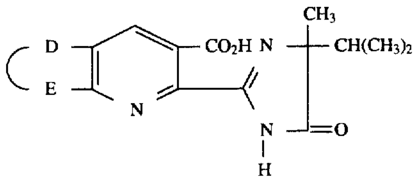
| Fused heteropyridine | mp°C. |
| --- | --- |
| 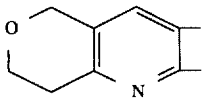 | 220.0–222.0 |
| 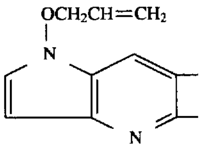 | 164.0–166.0 |
| 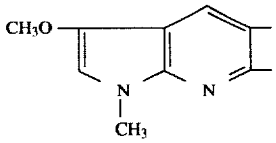 | 155.0–167.0 (dec) |
| 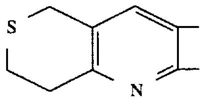 | 188.0–190.0 |
| 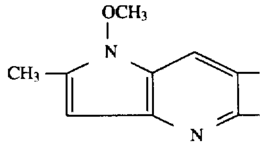 | 225.5–227.0 |
| 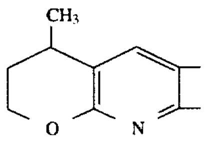 | 95.0–99.0 |
| 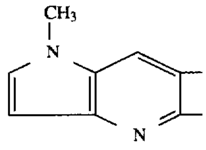 | 215.5–218.0 |
| 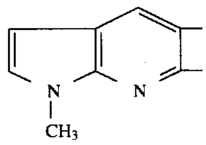 | 264.0–266.0 |
| 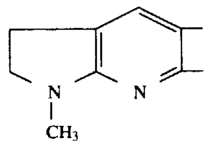 | 215.0–221.0 |
TABLE III-continued
(Imidazolin-2-yl)fused heteropyridine carboxylic acids
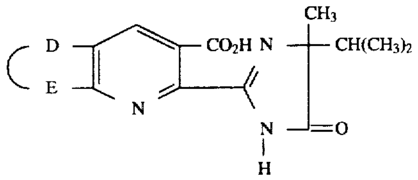
| Fused heteropyridine | mp°C. |
| --- | --- |
| 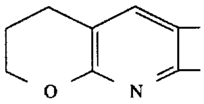 .1/2 $H_2O$ | 178.0–179.0 |
| 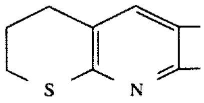 | 230.0–233.0 |
| 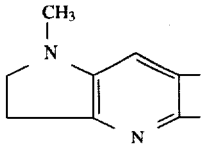 | — |
| 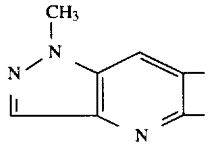 | 195.0–197.0 |
| 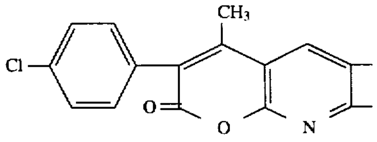 | 256.0–258.0 |
| 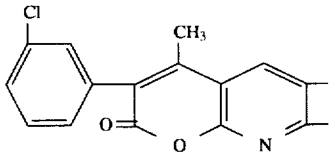 | 248.0–250.0 |
| 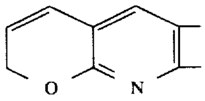 | 198.0–201.0 |
| 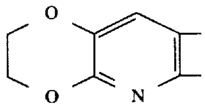 | 147.0–150.0 |
| 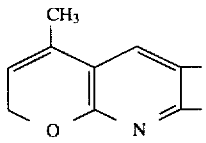 | 247.0–252.0 |
| 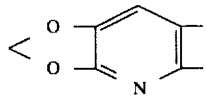 | 134–138 |

TABLE III-continued
(Imidazolin-2-yl)fused heteropyridine carboxylic acids
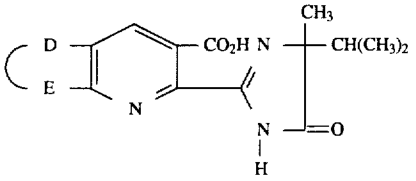
| Fused heteropyridine | mp°C. |
|---|---|
| 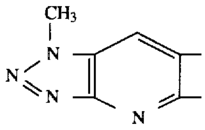 | — |
| 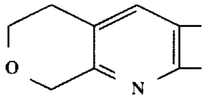 | 166–169 |
| 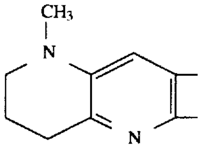 | — |
| 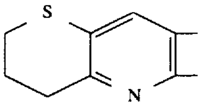 | 200.0–204.0 |
| 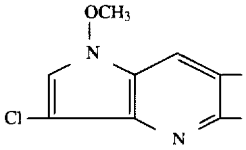 | 209.0–210.0 |
| 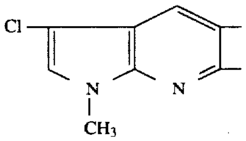 | 272.0–284.0 |
| 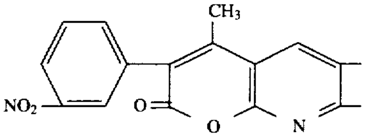 | 257.0–262.0 |
| 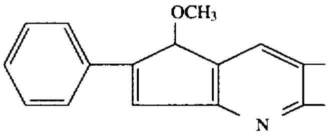 | 208.0–210.0 |
| 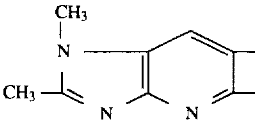 | 264.0 (dec) |
TABLE III-continued
(Imidazolin-2-yl)fused heteropyridine carboxylic acids
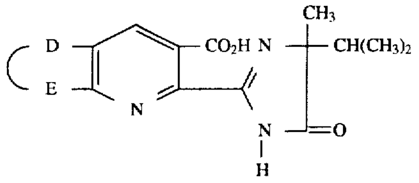
| Fused heteropyridine | mp°C. |
|---|---|
| 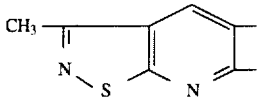 | — |
| 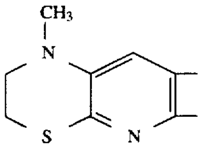 | — |
| 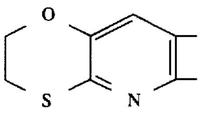 | — |
| 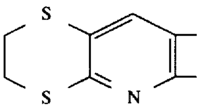 | — |
| 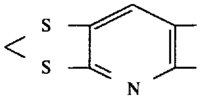 | — |
| 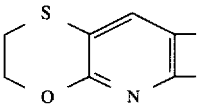 | — |
| 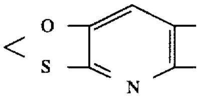 | — |
EXAMPLE 84
Preparation of 2-(4-isopropyl-4-methyl-5-oxo-2-imidazolin-2-yl)-8-oxide-1,8-naphthyridine-3-carboxylic acid
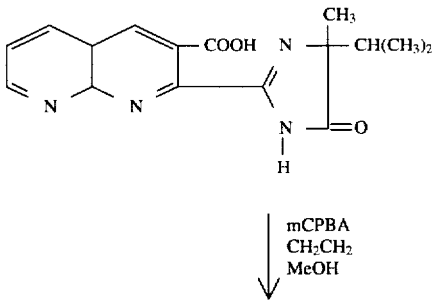

-continued

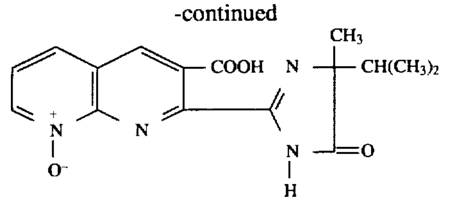

m-Chloroperbenzoic acid (37.70 g) is added in one portion of 2-(4-isopropyl-4-methyl-5-oxo-2-imidazolin-2-yl)-1,8-naphthyridine-3-carboxylic acid (27.32 g, 0.087 mol, 1 equiv) suspended in 465 mL methylene chloride and 300 mL methanol under $N_2$ and the mixture is stirred at room temperature for 15 hours. The suspension is filtered and the filtrate concentrated to a yellow solid which is recrystallized from methanol/ether, yielding the product as a dark yellow solid, (10.84 g, 37.7% yield, having a melting point 219°-221° C. (dec).

EXAMPLE 85

Preparation of methyl 7-chloro-2-(4-isopropyl-4-methyl-5-oxo-2-imidazolin-2-yl)-1,8-naphthylidine-3-carboxylate

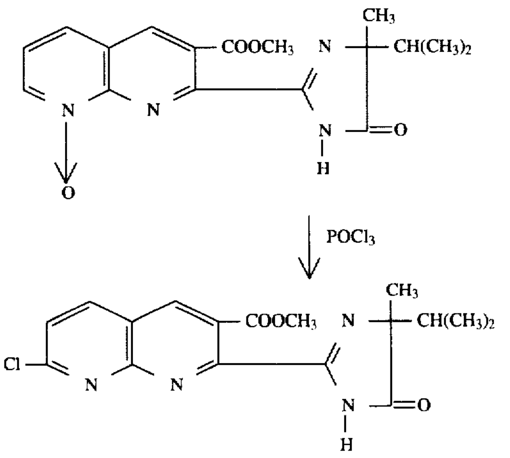

Methyl 2-(4-isopropyl-4-methyl-5-oxo-2-imidazolin-2-yl)-8-oxide-1,8-naphthylidine-3-carboxylate (4.11 g, 0.012 mol) is suspended under $N_2$ in 80 mL phosphorous oxychloride and heated to 53° C. for one hour. The solution is stripped to an oil, taken up in ethyl acetate and washed with water, a 10% sodium carbonate solution and brine. The organic layer is dried over $Na_2SO_4$, filtered and concentrated to a brown solid. The solid is purified by chromatography on silica gel, using methylene chloride and then 7:3 methylene chloride/ethyl acetate. The fractions containing the desired product are combined and the solvent removed yielding the title product as an off-white solid (1.77 g, 40.9%) having a melting point 161°-162° C.

EXAMPLE 86

Preparation of 2-isopropyl-2-methyl-7,8-dihydro-5H-pyrano[4,3-b]imidazo[2',1':5,1]pyrrolo[3,4-e]pyridine-3-(3H), Odione

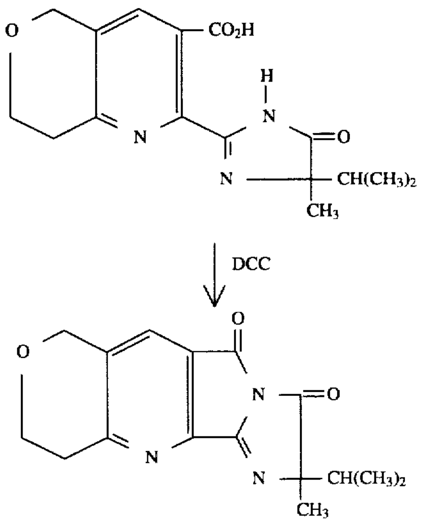

Dicyclohexylcarbodiimide (2.94 g) is added to a suspension of the imidazolinone (1.2 g) in methylene chloride (100 mL). After stirring for three days at room temperature, the mixture is filtered to remove a white solid bi-product and the filtrate is concentrated to give an oily solid which contains the product. Chromatography on silica gel using 9:1 methylene chloride:methanol gives 0.92 g of the desired product.

Using essentially the same procedure and using the appropriately substituted imidazolinyl heteropyridine carboxylic acid, gives other substituted imidazopyrroloheteropyridine-3,5-diones or 3-thione-5-ones.

EXAMPLE 87

Preparation of 3-isopropyl-3-methyl-7,8-dihydro-5H-pyrano[4,3-b]imidazo[2', 1': 5,1]pyrrolo[3,4-e-]pyridine-2(2H), 5-dione

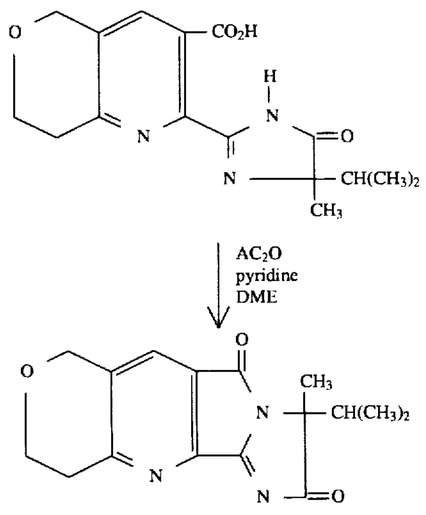

To a suspension of 6-(4-isopropyl-4-methyl-5-oxo-2-imidazolin-2-yl)-7,8-dihydro-5H-pyrano[4,3-b]pyridine-carboxylic acid (1.17 g, 3.75 mmol) in 20 mL dimethoxyethane (DME) is added 1.0 mL acetic anhydride and 0.5 mL pyridine. After stirring 24 hours at room temperature, the solids are filtered and washed with ether and the mother liquor is concentrated by adding xylene to remove pyridine. The residue is triturated with ether and combined with the first crop to give 1.10 g (100% of product as a solid.

Using essentially the same procedure and using the appropriately substituted imidazolinyl heteropyridine carboxylic acid, gives other substituted imidazopyrroloheteropyridine-2,5-diones, or 2-thione-5-ones.

EXAMPLE 88

Preparation of methyl 2-(4-isopropyl-4-methyl-5-oxo-2-imidazolin-2-yl)-7,8-dihydro-5H-pyrano[4,3-b] pyridine-3-carboxylate

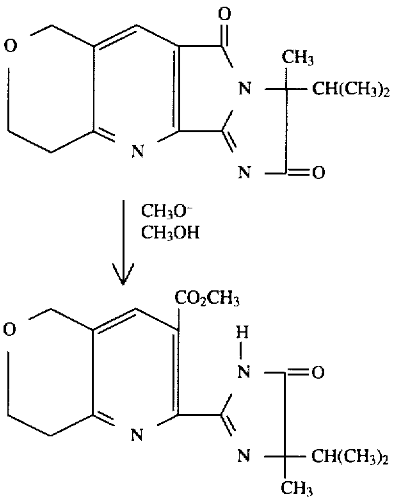

To a suspension of 2.0 g 2-isopropyl-2-methyl-7,8-dihydro-5H-pyrano[4,3-b ]imidazo[2', 1':5,1 ]pyrrolo[3,4-e]pyridine-2(2H), 5-dione in 100 mL absolute methyl alcohol is added 0.2 g of sodium methoxide over a five minute period. The temperature of the reaction is kept below 30° C. by immersion in an ice bath. After the addition was complete, the reaction mixture was kept at room temperature for 24 hours and acidified with three drops of acetic acid, and stripped in vacuo. The product was chromatographed on silica gel using methylene chloride-ethyl acetate to give 1.55 g of the ester product. After recrystallization from methylene chloride-hexane, it had mp 208°-220° C.

Utilizing essentially the same procedure and using the appropriately substituted fused hereto imidazopyrrolopyridine-2,5-dione and alcohol, gives the substituted (imidazolin-2-yl)fused heteropyridine carboxylates in Table IV below.

TABLE IV (Imidazolin-2-yl)fused heteropyridine carboxylates

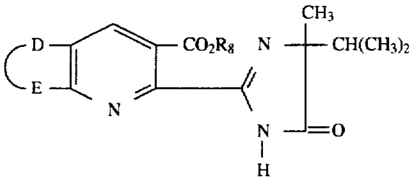

| Fused heteropyridine | $R_8$ | mp °C. |
|---|---|---|
| 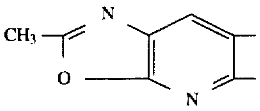 | $CH_3$ | 200.0-210.0 (dec) |
| 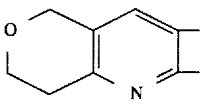 | $CH_3$ | 208.0-220.0 (dec) |
| 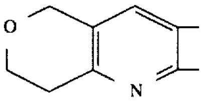 | 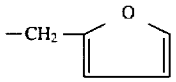 | 197.0-206.0 (dec) |
| 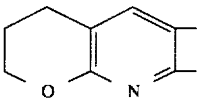 | $CH_2—C{\equiv}CH$ | — |
| 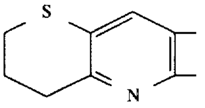 | 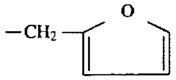 | — |
| 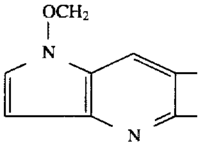 | $—CH_3$ | — |
| 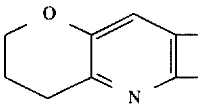 | $CH_2—C{\equiv}CH$ | — |

EXAMPLE 89

Preparation of methyl 2-(4-isopropyl-4-methyl-5-oxo-2-imidazolidinyl)-7,8-dihydro-5H-pyrano[4,3-b] pyridine-3-carboxylate Method A

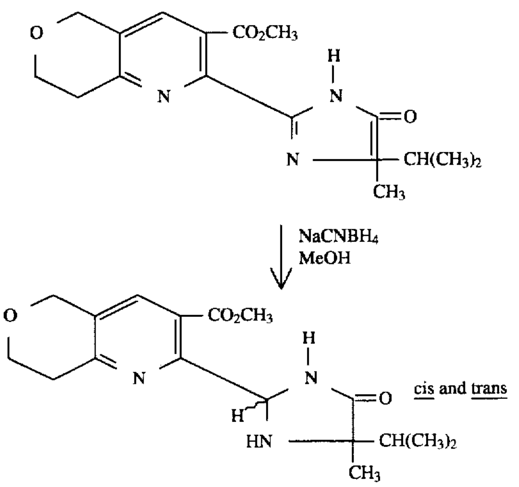

A solution of the ester in 50 mL absolute methanol is acidified to pH 3 with methanolic HCl. At 0° C. is added, all at once, 0.1 g sodium cyanoborohydride and the mixture stirred overnight at room temperature. The pH is again adjusted to 3 and an additional 0.1 g sodium cyanoborohydride is added. After 16 hours, the mixture is quenched in dilute HCl, then neutralized to pH 7 with carbonate and extracted with methylene chloride. The crude extract is stripped to a solid product which is a mixture of two isomers. These are separated by flash Chromatography on silica using ethyl acetate-methylene chloride. About 0.7 g of the cis or slower-moving isomer and 0.3 g of the faster-moving trans isomer are obtained.

Method B

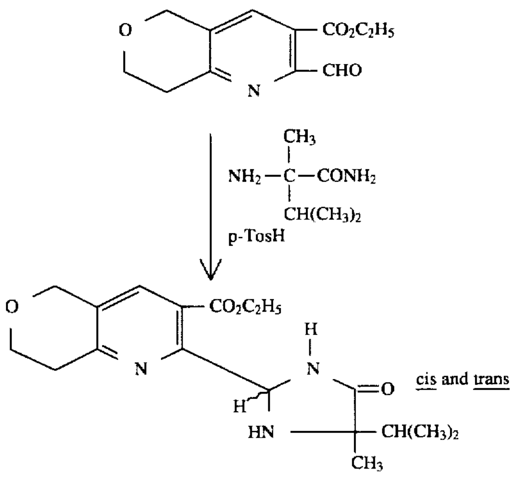

The ester aldehyde (1.0 g) and the aminoamide are dissolved in 50 mL toluene acid 0.10 g, E-toluene-sulfonic acid added. The mixture is refluxed six hours under nitrogen and the water separated using a Dean-Stark trap. It is then filtered while hot, cooled and then concentrated on a rotary evaporator. Extraction with hexane/ether gives, after cooling a white solid which is chromatographed as in Method A to give both cis- and trans-isomers.

Using essentially the same methods as A and B above, other imidazolidinyl fused heteropyridine carboxylates may be prepared.

EXAMPLE 90

Preparation of 3-isopropyl-3-methyl-1,7,8,9-b-tetrabydro-5H-pyrano[4,3-b]imidazo [2', 1': 5,1]pyrrolo[3,4-e]-pyridine 2(2), 5-dione

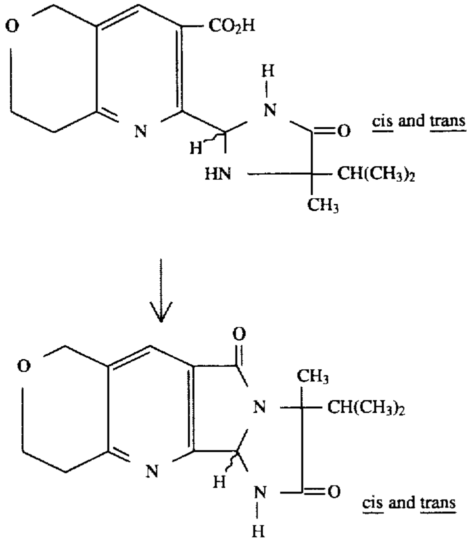

The acid (1.0 g) is suspended in 25 mL acetonitrile and 0.5 mL acetic anhydride and 0.5 mL pyridine are added. After 18 hours at room temperature, 20 mL ether is added and the mixture is filtered to obtain the product as a white solid.

Using essentially the same procedure, other imidazopyrroloheteropyridine-2,5-diones may be prepared.

EXAMPLE 91

Preparation of 2-(4-isopropyl-4-methyl-5-oxo-2-imidazolidinyl)-7,8-dihydro-5H-pyrano[4,3-b] pyridine-3-carboxylic acid

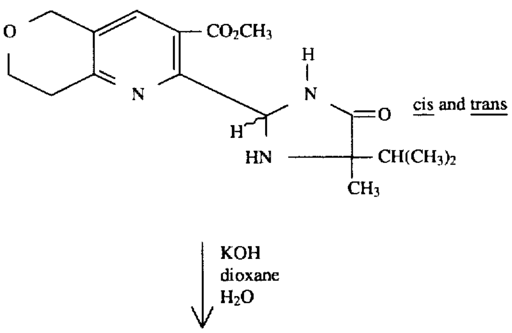

-continued

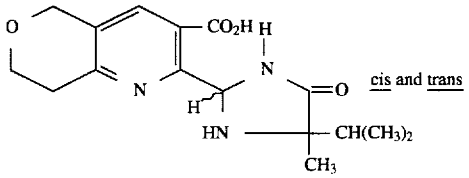

The ester (1.2 g) is stirred for 18 hours at room temperature in 75 mL dioxane containing 2 mL water and 0.5 mL 85% potassium hydroxide. The mixture is then acidified with methanolic HCl, filtered and the filtrate stripped and triturated with ether to give a white solid product.

Using essentially the same procedure, other imidazolidinylheteropyridine carboxylic acids may be prepared.

EXAMPLE 92

Preparation of diethyl 4-methyl-2-H-pyrano[2,3-b]pyridine-6,7-dicarboxylate

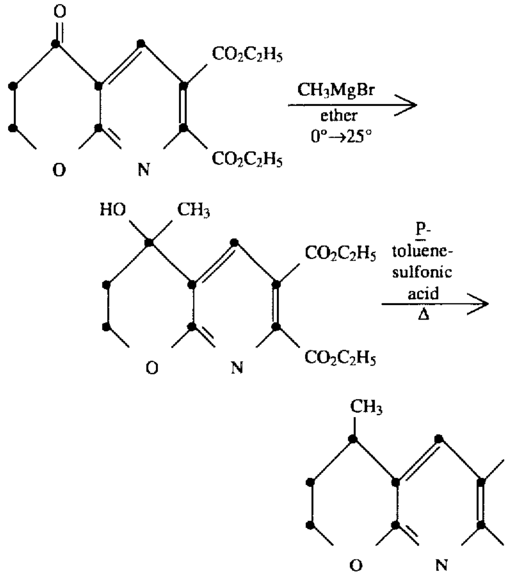

The 3,4-dihydro-4-oxo-pyrano [2,3-b ]pyridine diester (10.0 g, 0.34 mL) is dissolved in 150 mL ether and chilled to 0°, and methylmagnesium bromide is added dropwise over one hour. The reaction is then allowed to warm to room temperature, stand one hour, and is then poured onto ice water containing ammonium chloride. The organic layer is removed, dried over $MgSO_4$ and stripped to give the oily intermediate. This 4-methyl-4-hydroxy compound (5.0 g, 48%) is immediately redissolved in 100 mL toluene, 4.0 g or p-toluenesulfonic acid is added, and the mixture is heated to reflux for one hour. It is then cooled and the toluene is removed in vacuo. The residue is treated with dilute sodium bicarbonate solution and extracted with methylene chloride. The methylene chloride solution is dried over $MgSO_4$, filtered and concentrated to give, after silica gel chromatography, the 4-methyl-pyrano[2,3-b]pyridine diester as an oil (2.1 g, 44%).

EXAMPLE 93

Preparation of methyl 2-(1-acetyl-4-isopropyl-4-methyl-5-oxo-2-imidazolin-2-yl)-7,8-dihydro-5H-pyrano[4,3-b] pyridine-3-carboxylate

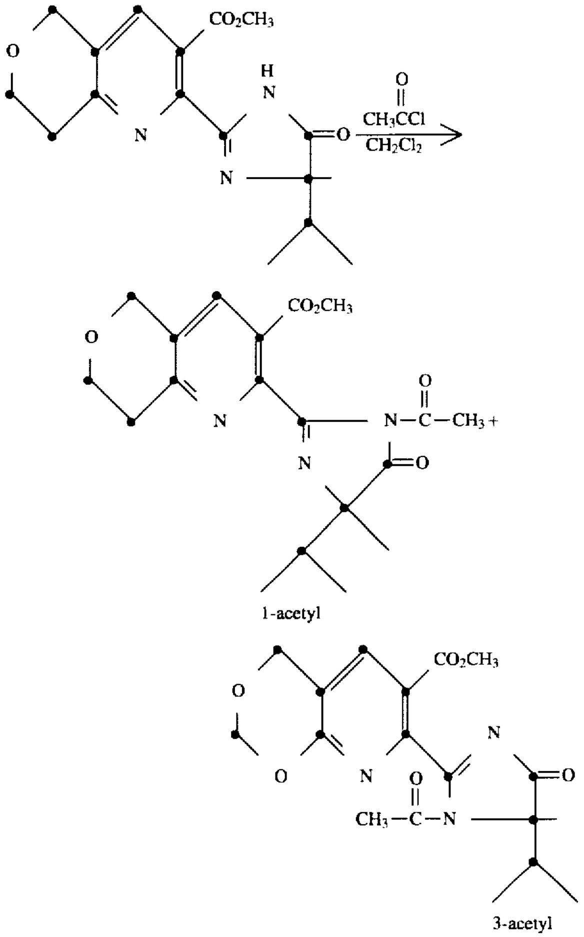

The pyranopyridine carboxylate prepared in example 88 (1.0 g is dissolved in methylene chloride (50 mL) and 1 mL triethylamine is added. The mixture is chilled in an ice bath while acetyl chloride is added (0.25 g) and then stirred for 2 h and allowed to reach room temperature. The mixture is filtered, the solvent is stripped and the residue is taken up in methylene chloride and ammonium chloride solution. The organic layer is separated, washed with brine, dried over anhydrous magnesium sulfate and concentrated to the crude product. Further purification by silica gel chromatography, eluting with methylene chloride-ethyl acetate 9:1 gives the desired 1-acetyl compound as the major product and the 3-acetyl compound as a by-product. The two materials are distinguishable by their infrared spectrum.

EXAMPLE 94

Preparation of 6-(1-acetyl-4-isopropyl-4-methyl-5-oxo72-imidazolin-2-yl )-4H-2,3-dihydro-pyrano[2,3-b]pyridine carboxylic acid

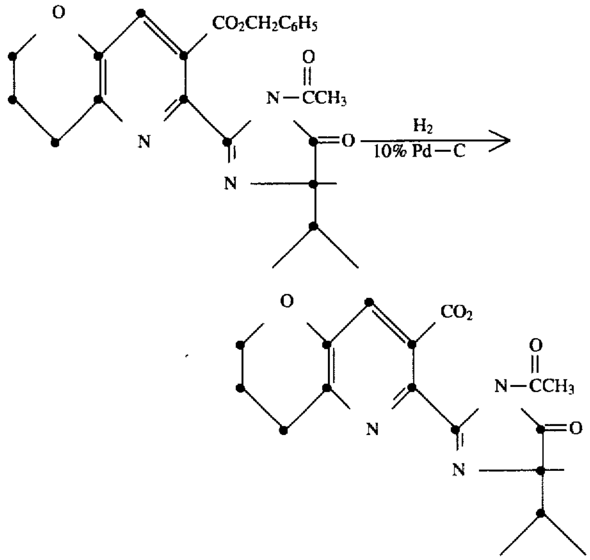

The benzylester is dissolved in 50 mL 955 ethanol and to it is added 0.100 g 10% Palladium on charcoal catalyst. The material is hydrogenated at atmospheric pressure for 6 h and then the solution is filtered, concentrated to give 0.6 g product. Using this same procedure, other N-acylated and N-sulfonated imidazolinone heteropyridine carboxylic acids are prepared.

EXAMPLE 95

Utilizing the procedures of example 45 and substituting the appropriate heterofused pyridine dicarboxylic acid anhydride and aminoamide or thioamide, other acid diamides and acid amide thioamides of the structures described in Table V below may be prepared.

TABLE V (1-Carbamoyl and 1-thiocarbamoyl-1,2-dialkyl) carbamoyl heteropyridine carboxylic acids

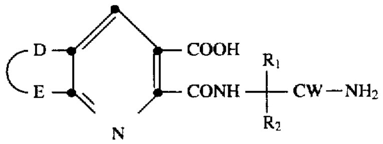

| Heteropyridine | W | $R_1$ | $R_2$ | mp °C. |
|---|---|---|---|---|
| 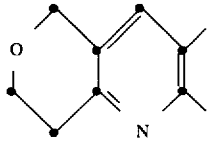 | S | $CH_3$ | $CH(CH_3)_2$ | |

TABLE V-continued (1-Carbamoyl and 1-thiocarbamoyl-1,2-dialkyl) carbamoyl heteropyridine carboxylic acids

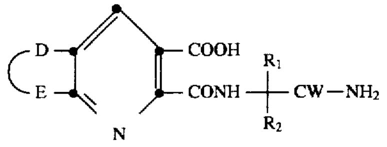

| Heteropyridine | W | $R_1$ | $R_2$ | mp °C. |
|---|---|---|---|---|
| 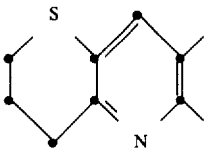 | S | $CH_3$ | $CH(CH_3)_2$ | |
| 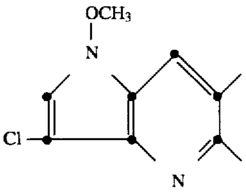 | S | $CH_3$ | $CH(CH_3)_2$ | |
| 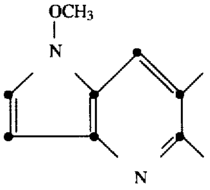 | S | $CH_3$ | $CH(CH_3)_2$ | |
| 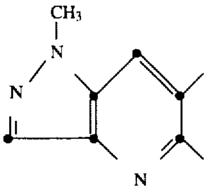 | S | $CH_3$ | $CH(CH_3)_2$ | |
| 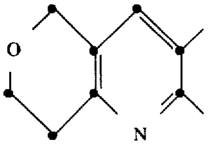 | O | $CH_3$ | $C_2H_5$ | |
| 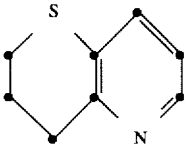 | O | $CH_3$ | $C_2H_5$ | |
| 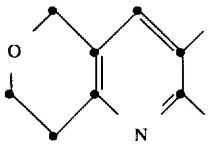 | O | $CH_3$ | cyclo-$C_3H_5$ | |

TABLE V-continued (1-Carbamoyl and 1-thiocarbamoyl-1,2-dialkyl) carbamoyl heteropyridine carboxylic acids

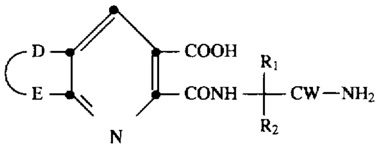

| Heteropyridine | W | $R_1$ | $R_2$ | mp °C. |
|---|---|---|---|---|
| 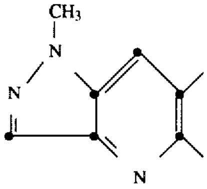 | O | $CH_3$ | t-$C_4H_9$ | |
| 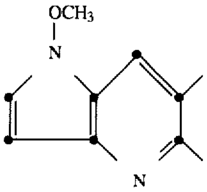 | O | $CH_3$ | n-$C_3H_7$ | |

TABLE V-continued (1-Carbamoyl and 1-thiocarbamoyl-1,2-dialkyl) carbamoyl heteropyridine carboxylic acids

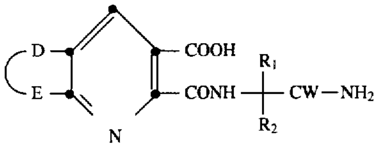

| Heteropyridine | W | $R_1$ | $R_2$ | mp °C. |
|---|---|---|---|---|
| 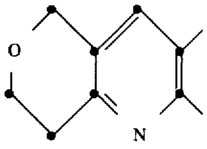 | O | $C_2H_5$ | $C_2H_5$ | |

EXAMPLE 96

Utilizing the procedures of examples 43, 44, 45, 82, 83, 86, 87, 88, 93 and 94, other (imidazolin-2-yl) fused heteropyridine compounds are prepared and are listed in Table VI.

TABLE VI (Imidazolin-2-yl) fused heteropyridine compounds

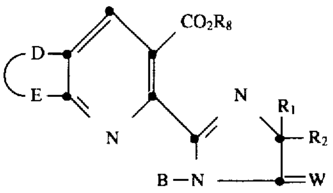

| Fused Heteropyridine | B | W | $R_1$ | $R_2$ | $R_8$ | mp °C. |
|---|---|---|---|---|---|---|
| 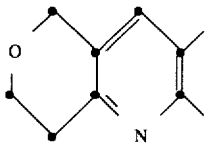 | H | S | $CH_3$ | $CH(CH_3)_2$ | H | |
| 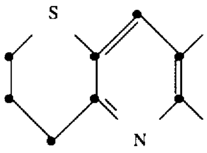 | H | S | $CH_3$ | $CH(CH_3)_2$ | H | 221-222 |
| 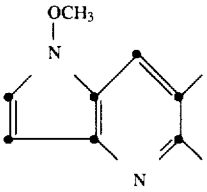 | H | S | $CH_3$ | $CH(CH_3)_2$ | H | |

TABLE VI-continued
(Imidazolin-2-yl) fused heteropyridine compounds
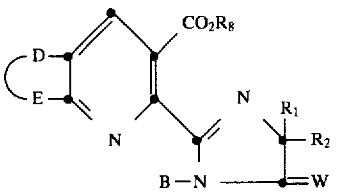
| Fused Heteropyridine | B | W | $R_1$ | $R_2$ | $R_8$ | mp °C. |
|---|---|---|---|---|---|---|
| 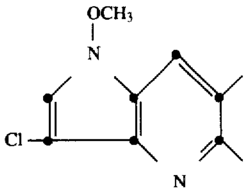 | H | S | $CH_3$ | $CH(CH_3)_2$ | H | |
| 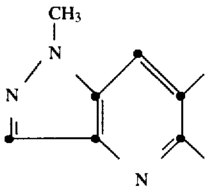 | H | S | $CH_3$ | $CH(CH_3)_2$ | H | |
| 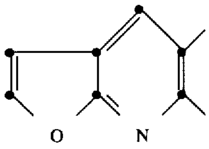 | H | O | $CH_3$ | $CH(CH_3)_2$ | $CH_2CH_2OCH_3$ | 152–154 |
| 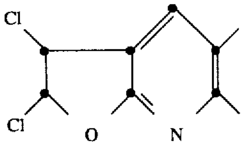 | H | O | $CH_3$ | $CH(CH_3)_2$ | $CH_3$ | 94 (dec.) |
| 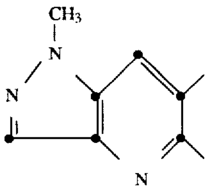 | H | O | $CH_3$ | $CH(CH_3)_2$ | $CH_2-C_6H_5$ | 81–82 |
| 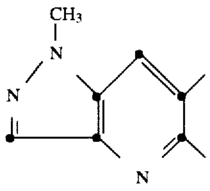 | H | O | $CH_3$ | $CH(CH_3)_2$ | $CH_2CH_2OCH_3$ | 110–112 |
| 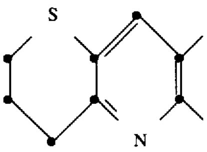 | H | O | $CH_3$ | $CH(CH_3)_2$ | $CH_3$ | 173–174 |

TABLE VI-continued
(Imidazolin-2-yl) fused heteropyridine compounds
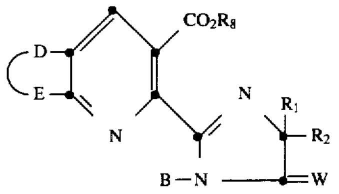
| Fused Heteropyridine | B | W | $R_1$ | $R_2$ | $R_8$ | mp °C. |
|---|---|---|---|---|---|---|
| 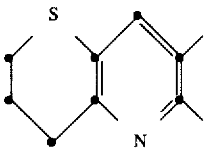 | H | O | $CH_3$ | $CH(CH_3)_2$ | $CH_2CH_2OCH_3$ | 164–167 |
| 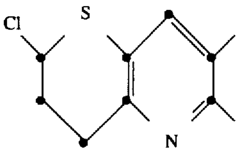 | H | O | $CH_3$ | $CH(CH_3)_2$ | $CH_3$ | 142–144 |
| 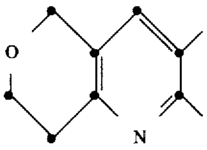 | H | O | $CH_3$ | $C_2H_5$ | H | |
| 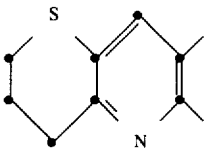 | H | O | $CH_3$ | $C_2H_5$ | H | |
| 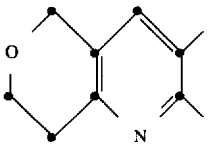 | H | O | $CH_3$ | cyclo-$C_3H_5$ | H | |
| 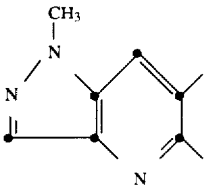 | H | O | $CH_3$ | t-$C_4H_9$ | H | |
| 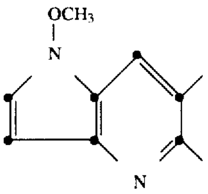 | H | O | $CH_3$ | n-$C_3H_7$ | H | |

TABLE VI-continued
(Imidazolin-2-yl) fused heteropyridine compounds
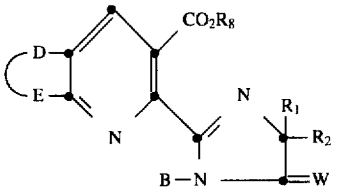
| Fused Heteropyridine | B | W | $R_1$ | $R_2$ | $R_8$ | mp °C. |
|---|---|---|---|---|---|---|
| 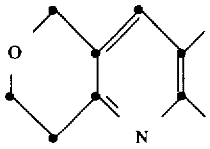 | H | O | $C_2H_5$ | $C_2H_5$ | H | |
| 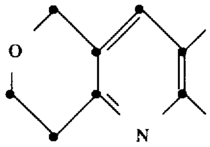 | H | O | $-(CH_2)_4CH(CH_3)-$ | | H | |
| 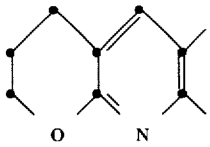 | $COCH_3$ | O | $CH_3$ | $CH(CH_3)_2$ | H | |
| 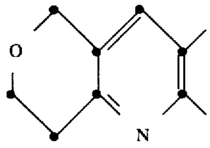 | $COCH_3$ | O | $CH_3$ | $CH(CH_3)_2$ | H | |
| 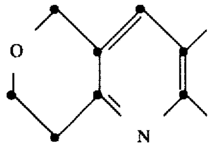 | $COCH_3$ | S | $CH_3$ | $CH(CH_3)_2$ | H | |
| 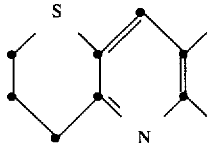 | $COCH_3$ | O | $CH_3$ | $CH(CH_3)_2$ | H | |
| 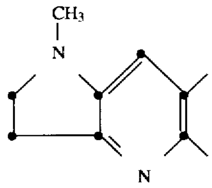 | $SO_2-C_6H_4-CH_3-p$ | O | $CH_3$ | $CH(CH_3)_2$ | H | |

TABLE VI-continued
(Imidazolin-2-yl) fused heteropyridine compounds
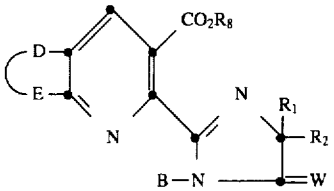
| Fused Heteropyridine | B | W | $R_1$ | $R_2$ | $R_8$ | mp °C. |
|---|---|---|---|---|---|---|
| 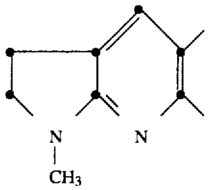 | $SO_2-C_6H_4-CH_3-P$ | O | $CH_3$ | $CH(CH_3)_2$ | H | |
| 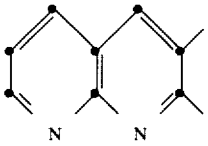 | $SO_2-C_6H_4-CH_3-P$ | O | $CH_3$ | $CH(CH_3)_2$ | H | |
| 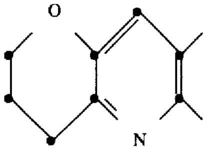 | O<br>‖<br>$CCH_3$ | O | $CH_3$ | $CH(CH_3)_2$ | H | |
| 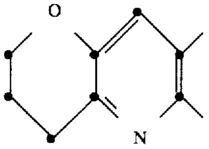 | O<br>‖<br>$CCH_3$ | S | $CH_3$ | $CH(CH_3)_2$ | H | |
| 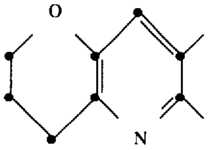 | $SO_2C_6H_4-CH_3-P$ | O | $CH_3$ | $CH(CH_3)_2$ | H | |
| 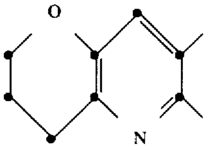 | O<br>‖<br>$CCH_3$ | O | $C_2H_5$ | $C_2H_5$ | H | |
| 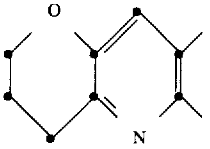 | O<br>‖<br>$CCH_3$ | O | $CH_3$ | cyclo-$C_3H_5$ | H | |
| 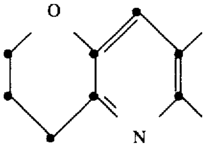 | O<br>‖<br>$CCH_3$ | O | $-(CH_2)_4-CH(CH_3)-$ | | H | |

TABLE VI-continued
(Imidazolin-2-yl) fused heteropyridine compounds
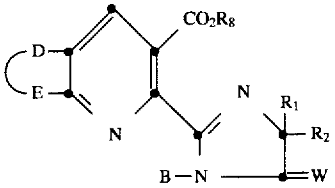
| Fused Heteropyridine | B | W | $R_1$ | $R_2$ | $R_8$ | mp °C. |
|---|---|---|---|---|---|---|
| 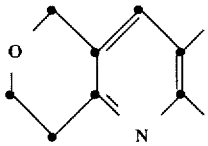 | O<br>‖<br>$CCH_3$ | S | $CH_3$ | $CH(CH_3)_2$ | $CH_3$ | |
| 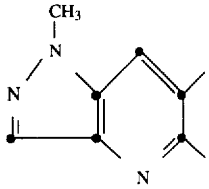 | O<br>‖<br>$CCH_3$ | S | $CH_3$ | $CH(CH_3)_2$ | $CH_3$ | |
| 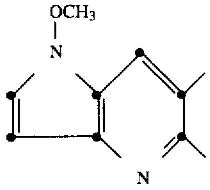 | O<br>‖<br>$CCH_3$ | S | $CH_3$ | $CH(CH_3)_2$ | $CH_3$ | |
| 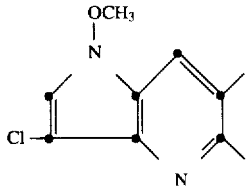 | O<br>‖<br>$CCH_3$ | S | $CH_3$ | $CH(CH_3)_2$ | $CH_3$ | |
| 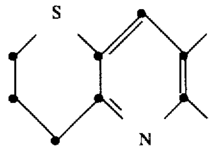 | O<br>‖<br>$CCH_3$ | S | $CH_3$ | $CH(CH_3)_2$ | $CH_3$ | |
| 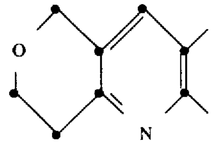 | H | O | $CH_3$ | cyclo-$C_3H_5$ | $CH_3$ | |
| 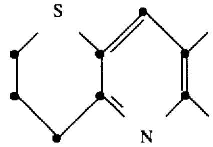 | H | O | $C_2H_5$ | $C_2H_5$ | $CH_3$ | |

TABLE VI-continued (Imidazolin-2-yl) fused heteropyridine compounds

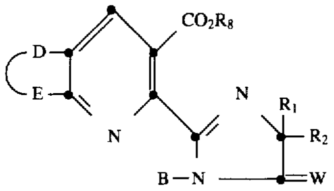

| Fused Heteropyridine | B | W | $R_1$ | $R_2$ | $R_8$ | mp °C. |
|---|---|---|---|---|---|---|
| 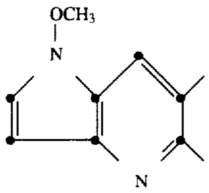 | H | O | $-(CH_2)_4-CH(CH_3)_3-$ | | $CH_3$ | |
| 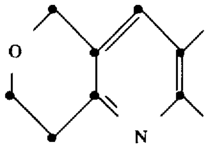 | O<br>‖<br>$CCH_3$ | O | $CH_3$ | $CH(CH_3)_2$ | $CH_3$ | |
| 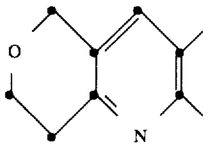 | $SO_2CH_3$ | O | $CH_3$ | $CH(CH_3)_2$ | $CH_3$ | |
| 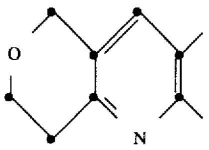 | $SO_2-C_6H_4-CH_3-\underline{P}$ | O | $CH_3$ | $CH(CH_3)_2$ | $CH_3$ | |
| 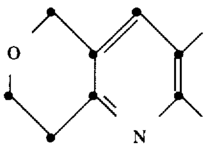 | O<br>‖<br>$C-C_6H_4$ | O | $CH_3$ | $CH(CH_3)_2$ | $CH_3$ | |
| 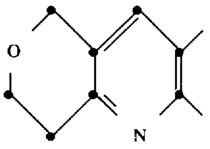 | O<br>‖<br>$CCH_3$ | O | $CH_3$ | $CH(CH_3)_2$ | $-CH_2C_6H_5$ | |
| 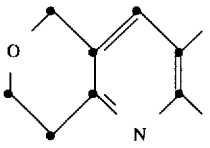 | $SO_2-C_6H_4-CH_3-\underline{P}$ | O | $CH_3$ | $CH(CH_3)_2$ | $-CH_2C_6H_5$ | |
| 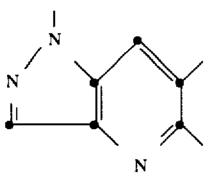 | O<br>‖<br>$CCH_3$ | O | $CH_3$ | $CH(CH_3)_2$ | $CH_3$ | |

TABLE VI-continued
(Imidazolin-2-yl) fused heteropyridine compounds
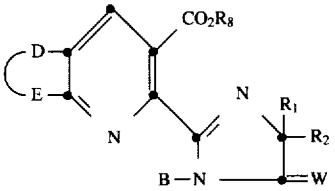
| Fused Heteropyridine | B | W | $R_1$ | $R_2$ | $R_8$ | mp °C. |
|---|---|---|---|---|---|---|
| 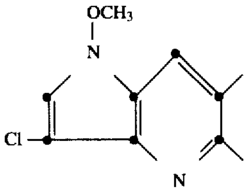 | O<br>‖<br>$CCH_3$ | O | $CH_3$ | $CH(CH_3)_2$ | $CH_3$ | |
| 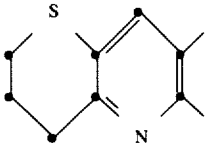 | O<br>‖<br>$CCH_3$ | O | $CH_3$ | $CH(CH_3)_2$ | $CH_3$ | |
| 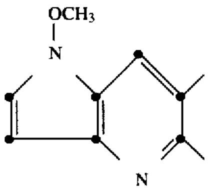 | O<br>‖<br>$CCH_3$ | O | $CH_3$ | $CH(CH_3)_2$ | $CH_3$ | |
| 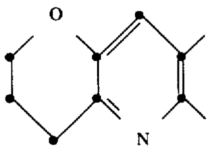 | O<br>‖<br>$CCH_3$ | O | $CH_3$ | $CH(CH_3)_2$ | $CH_2C_6H_5$ | |
| 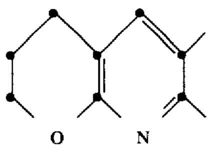 | O<br>‖<br>$CCH_3$ | O | $CH_3$ | $CH(CH_3)_2$ | $CH_2C_6H_5$ | |
| 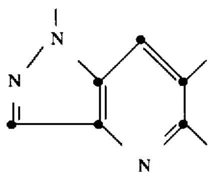 | O<br>‖<br>$CCH_3$ | O | $CH_3$ | $CH(CH_3)_2$ | $CH_2C_6H_5$ | |
| 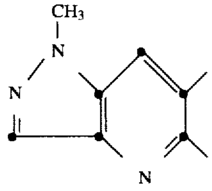 | H | S | $CH_3$ | $CH(CH_3)_2$ | $CH_3$ | |

TABLE VI-continued
(Imidazolin-2-yl) fused heteropyridine compounds
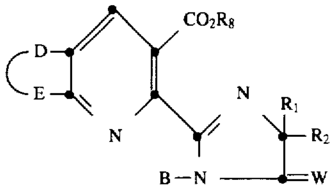
| Fused Heteropyridine | B | W | $R_1$ | $R_2$ | $R_8$ | mp °C. |
|---|---|---|---|---|---|---|
| 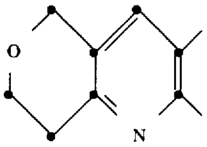 | H | S | $CH_3$ | $CH(CH_3)_2$ | $CH_3$ | |
| 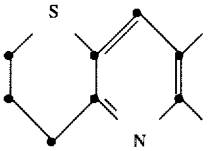 | H | S | $CH_3$ | $CH(CH_3)_2$ | $CH_3$ | 168–171 |
| 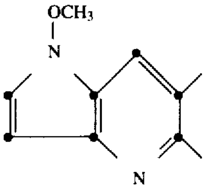 | H | S | $CH_3$ | $CH(CH_3)_2$ | $CH_3$ | |
| 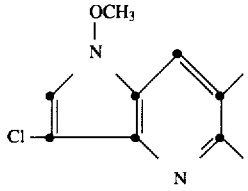 | H | S | $CH_3$ | $CH(CH_3)_2$ | $CH_3$ | |
EXAMPLE 97
Utilizing the procedure of example 86, other imidazopyrroloheteropyridine-3,5-diones are prepared and are listed in Table VII.

TABLE VII
Imidazopyrroloheteropyridine-3,5-diones
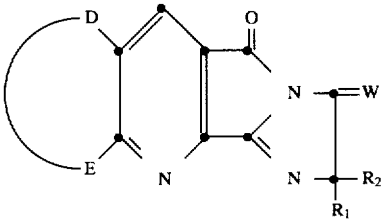
| Fused Heteropyridine | W | $R_1$ | $R_2$ | mp °C. |
|---|---|---|---|---|
| 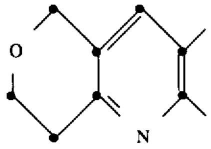 | O | $CH_3$ | $CH(CH_3)_2$ | |
| 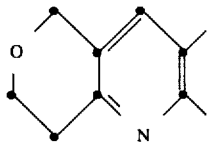 | S | $CH_3$ | $CH(CH_3)_2$ | |
| 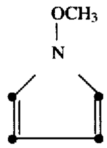 | O | $CH_3$ | $CH(CH_3)_2$ | |
| 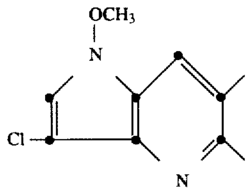 | O | $CH_3$ | $CH(CH_3)_2$ | |
| 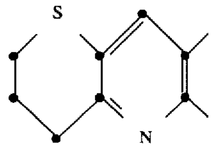 | O | $CH_3$ | $CH(CH_3)_2$ | 228–236 |
| 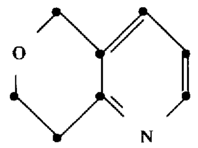 | O | $CH_3$ | $C_2H_5$ | |
| 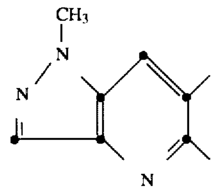 | O | $CH_3$ | $CH(CH_3)_2$ | 180–183 |

TABLE VII-continued

Imidazopyrroloheteropyridine-3,5-diones

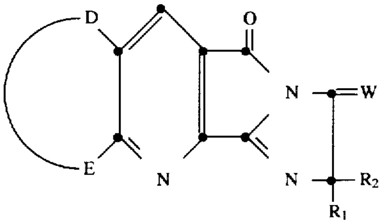

| Fused Heteropyridine | W | $R_1$ | $R_2$ | mp °C. |
|---|---|---|---|---|
| 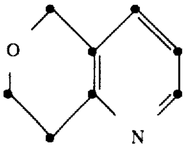 | O | $C_2H_5$ | $C_2H_5$ | |
| 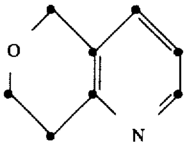 | O | $CH_3$ | cyclo-$C_3H_5$ | |
| 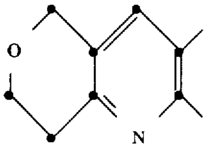 | O | $-CH_2CH_2CH_2CH_2CH(CH_3)-$ | | |

EXAMPLE 98

Utilizing the procedure of example 87, other imidazopyrroloheteropyridine-2,5-diones and imidazopyrroloheteropyridine-2-thione-5-ones are prepared and are listed in Table VIII.

TABLE VIII

Imidazopyrroloheteropyridine-2,5-diones (-2-thione-5-ones)

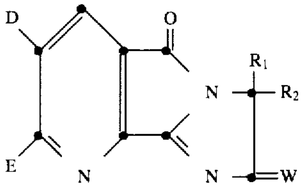

| Fused Heteropyridine | W | $R_1$ | $R_2$ | mp °C. |
|---|---|---|---|---|
| 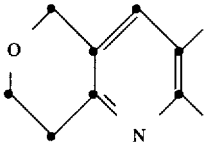 | O | $CH_3$ | $CH(CH_3)_2$ | |

TABLE VIII-continued
Imidazopyrroloheteropyridine-2,5-diones (-2-thione-5-ones)
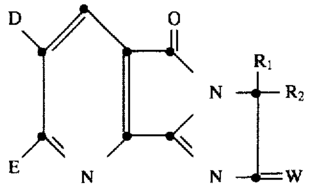
| Fused Heteropyridine | W | $R_1$ | $R_2$ | mp °C. |
|---|---|---|---|---|
| 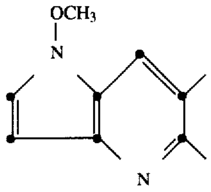 | O | $CH_3$ | $CH(CH_3)_2$ | |
| 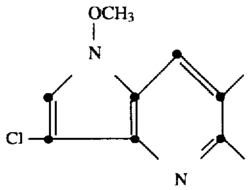 | O | $CH_3$ | $CH(CH_3)_2$ | |
| 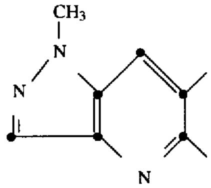 | O | $CH_3$ | $CH(CH_3)_2$ | |
| 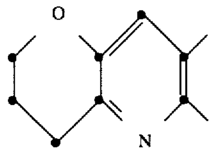 | O | $CH_3$ | $CH(CH_3)_2$ | |
| 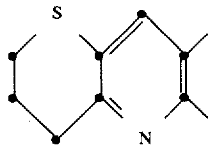 | O | $CH_3$ | $CH(CH_3)_2$ | |
| 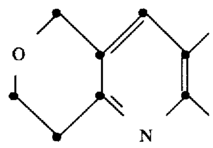 | S | $CH_3$ | $CH(CH_3)_2$ | |
| 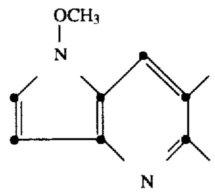 | S | $CH_3$ | $CH(CH_3)_2$ | |

TABLE VIII-continued
Imidazopyrroloheteropyridine-2,5-diones (-2-thione-5-ones)
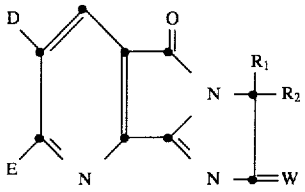
| Fused Heteropyridine | W | $R_1$ | $R_2$ | mp °C. |
|---|---|---|---|---|
| 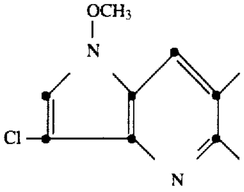 | S | $CH_3$ | $CH(CH_3)_2$ | |
| 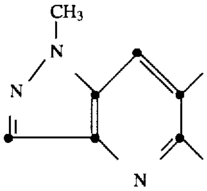 | S | $CH_3$ | $CH(CH_3)_2$ | |
| 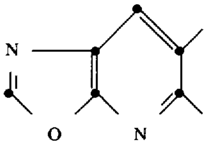 | O | $CH_3$ | $CH(CH_3)_2$ | |
| 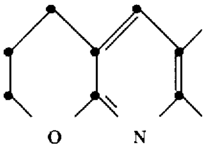 | O | $CH_3$ | $CH(CH_3)_2$ | |
| 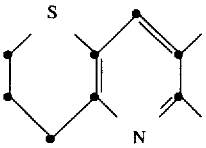 | S | $CH_3$ | $CH(CH_3)_2$ | |
| 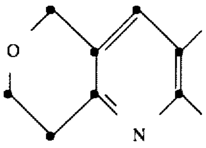 | O | $CH_3$ | cyclo-$C_3H_5$ | |
| 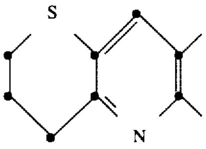 | O | $C_2H_5$ | $C_2H_5$ | |

TABLE VIII-continued

Imidazopyrroloheteropyridine-2,5-diones (-2-thione-5-ones)

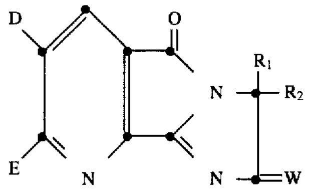

| Fused Heteropyridine | W | $R_1$ | $R_2$ | mp °C. |
|---|---|---|---|---|
| 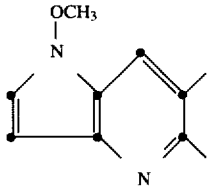 | O | $-CH_2CH_2CH_2CH_2CH(CH_3)-$ | | |

EXAMPLE 99

Utilizing the procedure of example 89, other imidazolidinyl fused heteropyridine carboxylates and carboxylic acids are prepared and are listed in Table IX.

TABLE IX

Imidazolidinyl Fused Heteropyridine Carboxylates

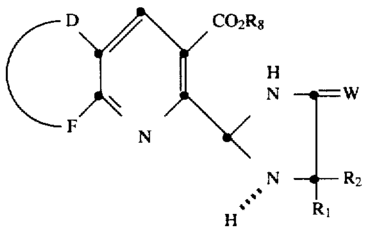

| Fused Heteropyridine | $R_8$ | $R_1$ | $R_2$ | W | mp °C. |
|---|---|---|---|---|---|
| 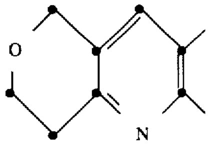 | $CH_3$ | $CH_3$ | $CH(CH_3)_2$ | O | |
| 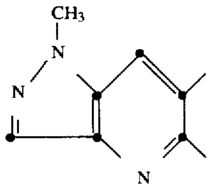 | $CH_3$ | $CH_3$ | $CH(CH_3)_2$ | O | |
| 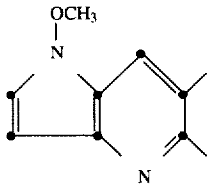 | $CH_3$ | $CH_3$ | $CH(CH_3)_2$ | O | |

TABLE IX-continued
Imidazolidinyl Fused Heteropyridine Carboxylates
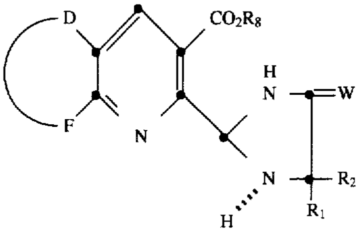
| Fused Heteropyridine | $R_8$ | $R_1$ | $R_2$ | W | mp °C. |
|---|---|---|---|---|---|
| 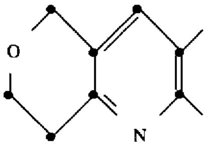 | $C_2H_5$ | $CH_3$ | $CH(CH_3)_2$ | O | |
| 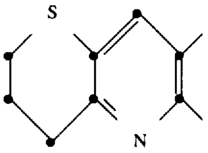 | $CH_3$ | $CH_3$ | $CH(CH_3)_2$ | O | trans 186–191<br>cis 184–191 |
| 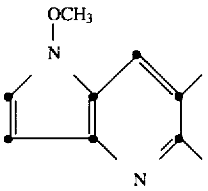 | $CH_3$ | $CH_3$ | $CH(CH_3)_2$ | O | |
| 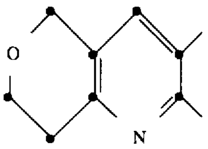 | 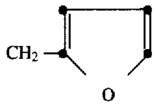 | $CH_3$ | $CH(CH_3)_2$ | O | |
| 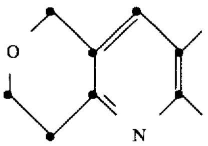 | $CH_3$ | $CH_3$ | $CH(CH_3)_2$ | S | |
| 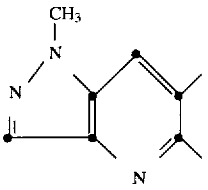 | $CH_3$ | $CH_3$ | $CH(CH_3)_2$ | S | |
| 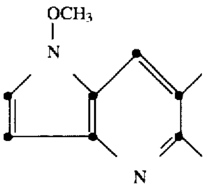 | $CH_3$ | $CH_3$ | $CH(CH_3)_2$ | S | |

TABLE IX-continued
Imidazolidinyl Fused Heteropyridine Carboxylates
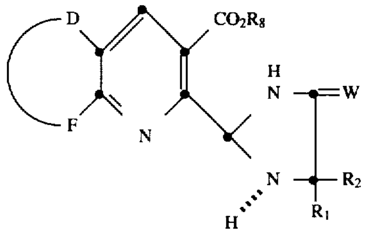
| Fused Heteropyridine | $R_8$ | $R_1$ | $R_2$ | W | mp °C. |
|---|---|---|---|---|---|
| 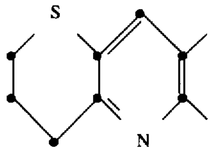 | $CH_3$ | $CH_3$ | $CH(CH_3)_2$ | S | |
| 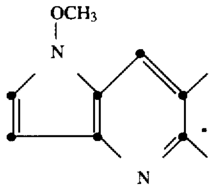 | $CH_3$ | $CH_3$ | $CH(CH_3)_2$ | S | |
| 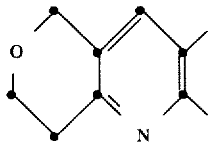 | $CH_3$ | $C_2H_5$ | $C_2H_5$ | O | |
| 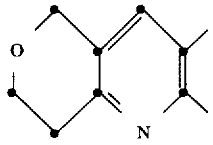 | $CH_3$ | $CH_3$ | cyclo-$C_3H_5$ | O | |
| 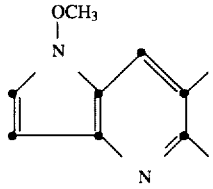 | $CH_3$ | $-(CH_2)_4CH(CH_3)-$ | | O | |
| 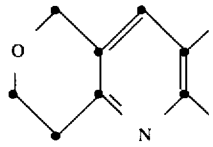 | H | $CH_3$ | $CH(CH_3)_2$ | O | |
| 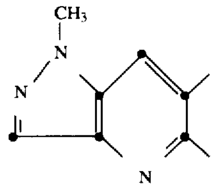 | H | $CH_3$ | $CH(CH_3)_2$ | O | |

TABLE IX-continued
Imidazolidinyl Fused Heteropyridine Carboxylates
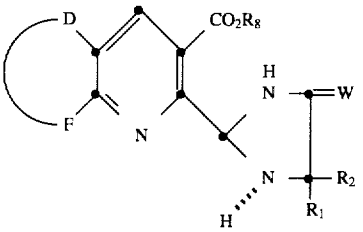
| Fused Heteropyridine | $R_8$ | $R_1$ | $R_2$ | W | mp °C. |
|---|---|---|---|---|---|
| 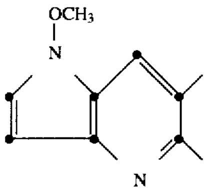 | H | $CH_3$ | $CH(CH_3)_2$ | O | |
| 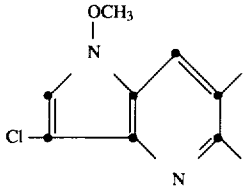 | H | $CH_3$ | $CH(CH_3)_2$ | O | |
| 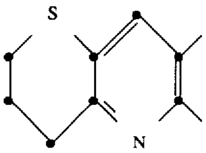 | H | $CH_3$ | $CH(CH_3)_2$ | O | |
| 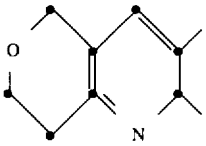 | H | $C_2H_5$ | $C_2H_5$ | O | |
| 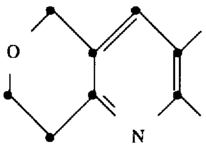 | H | $CH_3$ | cyclo-$C_3H_5$ | O | |
| 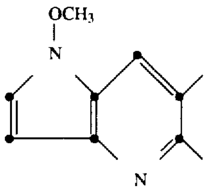 | H | $-(CH_2)_4CH(CH_3)-$ | | O | |
| 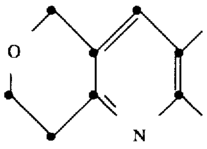 | H | $CH_3$ | $CH(CH_3)_2$ | S | |

TABLE IX-continued
Imidazolidinyl Fused Heteropyridine Carboxylates
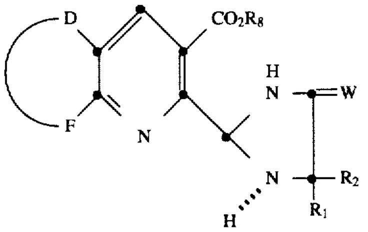
| Fused Heteropyridine | $R_8$ | $R_1$ | $R_2$ | W | mp °C. |
|---|---|---|---|---|---|
| 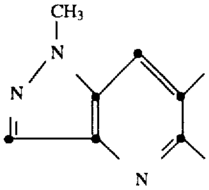 | H | $CH_3$ | $CH(CH_3)_2$ | S | |
| 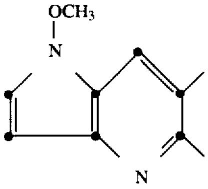 | H | $CH_3$ | $CH(CH_3)_2$ | S | |
| 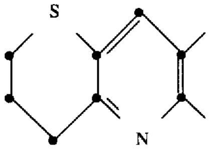 | H | $CH_3$ | $CH(CH_3)_2$ | S | |
| 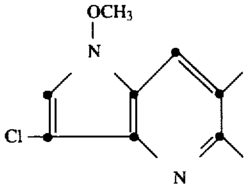 | H | $CH_3$ | $CH(CH_3)_2$ | S | |
EXAMPLE 100
Utilizing the procedures of examples 90 and 91, other imidazopyrroloheteropyridine-2,5-diones are imidazopyrroloheteropyridine-2-thione-5-ones are prepared and are listed in Table X.

TABLE X
Imidazopyrroloheteropyridine-2,5-diones (-2-thione-5-ones)
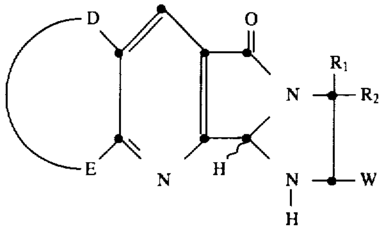
| Fused Heteropyridine | $R_1$ | $R_2$ | W | mp °C. |
|---|---|---|---|---|
| 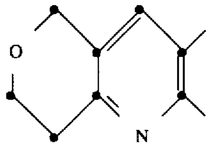 | $CH_3$ | $CH(CH_3)_2$ | O | |
| 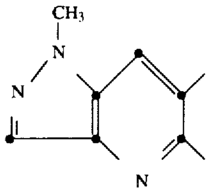 | $CH_3$ | $CH(CH_3)_2$ | O | |
| 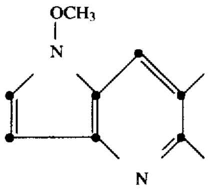 | $CH_3$ | $CH(CH_3)_2$ | O | |
| 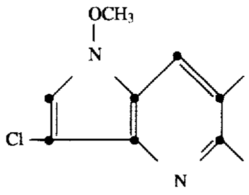 | $CH_3$ | $CH(CH_3)_2$ | O | |
| 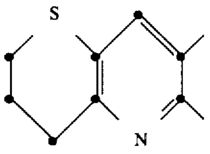 | $CH_3$ | $CH(CH_3)_2$ | O | 225–263 |
| 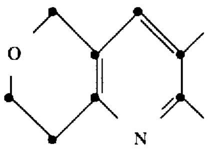 | $CH_3$ | $CH(CH_3)_2$ | S | |
| 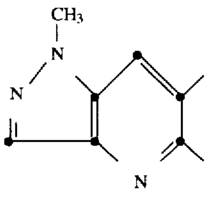 | $CH_3$ | $CH(CH_3)_2$ | S | |

TABLE X-continued

Imidazopyrroloheteropyridine-2,5-diones (-2-thione-5-ones)

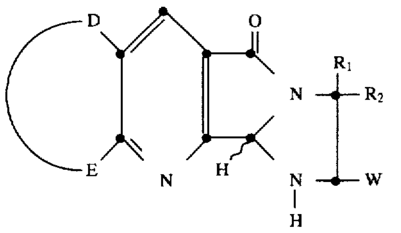

| Fused Heteropyridine | $R_1$ | $R_2$ | W | mp °C. |
|---|---|---|---|---|
| 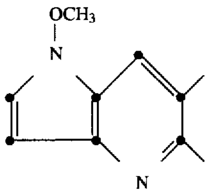 | $CH_3$ | $CH(CH_3)2$ | S | |
| 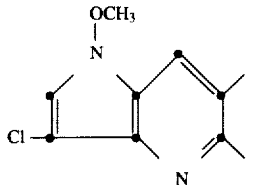 | $CH_3$ | $CH(CH_3)_2$ | S | |
| 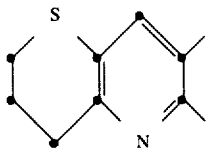 | $CH_3$ | $CH(CH_3)_2$ | S | |
| 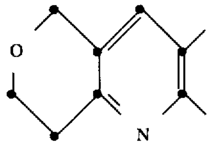 | $CH_3$ | cyclo-$C_3H_5$ | O | |
| 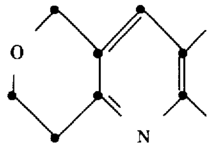 | $C_2H_5$ | $C_2H_5$ | O | |
| 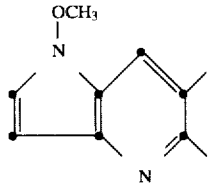 | $-CH_2CH_2CH_2CH_2-CH(CH_3)-$ | | O | |

EXAMPLE 101

Postemergence Herbicidal Evaluation of Test Compounds

The postemergence herbicidal activity of the compounds of the present invention is demonstrated by the following tests, wherein a variety of monocotyledonous and dicotyledonous plants are created with test compounds dispersed in aqueous acetone mixtures. In the tests, seedling plants are grown in jiffy flats for about two weeks. The test compounds are dispersed in 50/50 acetone/water mixtures containing 0.5% TWEEN® 20, a polyoxyethylene sorbitan monolaurate surfactant of Atlas Chemical Industries, in sufficient quantity to provide the equivalent of about 0.016 kg to 10 kg per hectare of active compound when applied to the plants through a spray nozzle operating at 40 psig for a predetermined time. After spraying, the plants are placed on greenhouse benches and are cared for in the usual manner, commensurate with conventional greenhouse practices. From four to five weeks after treatment, the seedling plants, are examined and rated according to the rating system provided below. The data obtained are recorded in Table XI below.

| Rating System | % Difference in Growth from the Check |
|---|---|
| 0 - No effect | 0 |
| 1 - Possible effect | 1–10 |
| 2 - Slight effect | 11–25 |
| 3 - Moderate effect | 26–40 |
| 5 - Definite injury | 41–60 |
| 6 - Herbicidal effect | 61–75 |
| 7 - Good herbicidal effect | 76–90 |
| 8 - Approaching complete kill | 91–99 |
| 9 - Complete kill | 100 |
| 4 - Abnormal growth, that is, a definite physiological malformation but with an overall effect less than a 5 on the rating scale. | |

In most cases the data are for a single test, but in several instances, they are average values obtained from more than one test.

| Plant Species Used | |
|---|---|
| Barnyardgrass | (*Echinochloa crusgalli*) |
| Green Foxtail | (*Setaria viridis*) |
| Purple Nutsedge | (*Cyperus rotundus* L.) |
| Wild Oats | (*Avena fatua*) |
| Quackgrass | (*Agropyron repens*) |
| Field Bindweed | (*Convolvulus arvensis* L.) |
| Cocklebur | (*Xanthium pensylvanicum*) |
| Morningglory | (*Ipomoea purpurea*) |
| Ragweed | (*Ambrosia artemisiifolia*) |
| Velvetleaf | (*Abutilon theophrasti*) |
| Barley | (*Hordeum vulgare*) |
| Corn | (*Zea mays*) |
| Rice | (*Oryza sativa*) |
| Soybean | (*Glycine max*) |
| Sunflower | (*Helianthus annus*) |
| Wheat | (*Triticum aestivum*) |

TABLE XI

| | | Post-Emergence Tests - Rates in kg/ha | | | | | | | | | |
|---|---|---|---|---|---|---|---|---|---|---|---|
| Compound | RATE | BARNY ARDGR | FOX TAIL SP | P NUT SEDGE | WILD OATS | QUACK GRASS | FLD B INDWD | MATRI CARIA | MRN GLRY SP | RAG WEED | VEL-VET LEAF |
| 2-(4-Isopropyl-4-methyl-5- | 1.000 | 9.0 | 9.0 | 6.0 | 9.0 | 9.0 | 7.0 | 2.0 | 9.0 | 2.0 | 4.0 |
| oxo-2-imidazolin-2-yl)-1,8- | .500 | 9.0 | 7.0 | 4.0 | 8.0 | 7.0 | 7.0 | 0.0 | 7.0 | 0.0 | 2.0 |
| naphthyridine-3- | .250 | 4.0 | 6.0 | 1.0 | 8.0 | 7.0 | 4.0 | 0.0 | 6.0 | 0.0 | 1.0 |
| carboxylic acid | .125 | 2.0 | 2.0 | 0.0 | 6.0 | 4.0 | 2.0 | 0.0 | 2.0 | 0.0 | 0.0 |
| 2-(4-Isopropyl-4-methyl-5- | 1.000 | 2.0 | 2.0 | 0.0 | 4.0 | 0.0 | 9.0 | 0.0 | 0.0 | 0.0 | 2.0 |
| oxo-2-imidazolin-2-yl)-1,6- | .500 | | 2.0 | 0.0 | 2.0 | 0.0 | 9.0 | 0.0 | 0.0 | 0.0 | 2.0 |
| naphthyridine-3- | .250 | 2.0 | 2.0 | 0.0 | 1.0 | 0.0 | 6.0 | 0.0 | 0.0 | 0.0 | 2.0 |
| carboxylic acid | .125 | 2.0 | 1.0 | 0.0 | 1.0 | 0.0 | 2.0 | 0.0 | 0.0 | 0.0 | 1.0 |
| 2-(4-Isopropyl-4-methyl-5- | 1.000 | 8.0 | 9.0 | 0.0 | 9.0 | 6.0 | 8.0 | 0.0 | 7.0 | 0.0 | 2.0 |
| oxo-2-imidazolin-2-yl)-1,8- | .500 | 8.0 | 9.0 | 0.0 | 6.0 | | 6.0 | 0.0 | 4.0 | 0.0 | 2.0 |
| naphthyridine-3-carboxy- | .250 | 4.0 | 8.0 | 0.0 | 2.0 | 0.0 | 4.0 | 0.0 | 2.0 | 0.0 | 0.0 |
| lic acid, 8-oxide | .125 | 2.0 | 4.0 | 0.0 | 0.0 | 0.0 | 2.0 | 0.0 | 0.0 | 0.0 | 0.0 |
| 6-(4-Isopropyl-4-methyl-5- | 1.000 | 9.0 | 9.0 | 4.0 | 8.0 | 7.0 | 6.0 | 7.0 | 4.0 | 9.0 | 7.0 |
| oxo-2-imidazolin-2-yl)-3- | .500 | 2.0 | 8.0 | 2.0 | 4.0 | 2.0 | 4.0 | 2.0 | 1.0 | 7.0 | 4.0 |
| methyl-isoxazolo[5,4-b] | .250 | 0.0 | 4.0 | 0.0 | 0.0 | 0.0 | 0.0 | 0.0 | 0.0 | 0.0 | 0.0 |
| pyridine-5-carboxylic acid | | | | | | | | | | | |
| 5-(4-Isopropyl-4-methyl-5- | 1.000 | 9.0 | 9.0 | 7.0 | 9.0 | 9.0 | 9.0 | 9.0 | 9.0 | 9.0 | 9.0 |
| oxo-2-imidazolin-2-yl)-1- | .500 | 9.0 | 9.0 | 9.0 | 9.0 | 9.0 | 9.0 | 9.0 | 9.0 | 9.0 | 9.0 |
| methoxy-1H-pyrrolo[3,2-b] | .250 | 9.0 | 9.0 | 7.0 | 9.0 | 9.0 | 9.0 | 9.0 | 9.0 | 8.0 | 9.0 |
| pyridine-6-carboxylic acid | .125 | 9.0 | 9.0 | 7.0 | 9.0 | 9.0 | 9.0 | 9.0 | 9.0 | 6.0 | 9.0 |
| 5-(4-Isopropyl-4-methyl-5- | 1.000 | 5.0 | 9.0 | 8.0 | 9.0 | 4.0 | | 3.0 | 4.0 | 4.0 | 8.0 |
| oxo-2-imidazolin-2-yl)-2- | .500 | 2.0 | 7.0 | 3.0 | 8.0 | 0.0 | 3.0 | 3.0 | 2.0 | 4.0 | 7.0 |
| methyloxazolo[5,4-b] | .250 | 1.0 | | 1.0 | 6.0 | 0.0 | 1.0 | 0.0 | 2.0 | 2.0 | 4.0 |
| pyridine-6-carboxylic acid | .125 | 0.0 | 6.0 | 0.0 | 1.0 | 0.0 | 0.0 | 0.0 | 1.0 | 0.0 | 2.0 |
| 7,8-Dihydro-2-(4-isopropyl- | 8.000 | 9.0 | | 9.0 | 9.0 | 9.0 | 9.0 | | 8.0 | 9.0 | 9.0 |
| 4-methyl-5-oxo-2-imidazol- | 1.000 | 9.0 | 9.0 | 9.0 | 9.0 | 9.0 | 9.0 | 9.0 | 9.0 | 9.0 | 9.0 |
| in-2-yl)-5H-pyrano[4,3-b] | .500 | 9.0 | 9.0 | 9.0 | 9.0 | 9.0 | 9.0 | 9.0 | 9.0 | 9.0 | 9.0 |
| pyridine-3-carboxylic acid | .250 | 9.0 | 9.0 | 9.0 | 9.0 | 9.0 | 9.0 | 2.0 | 9.0 | 9.0 | 9.0 |
| | .125 | 9.0 | 9.0 | 9.0 | 9.0 | 9.0 | 9.0 | 4.0 | 9.0 | 9.0 | 9.0 |
| 1-(Allyloxy)-5-(4- | 1.000 | 9.0 | 9.0 | 4.0 | 9.0 | 8.0 | 9.0 | 9.0 | 9.0 | 9.0 | 9.0 |
| isopropyl-4-methyl-5-oxo- | .500 | 9.0 | 9.0 | 4.0 | 9.0 | 7.0 | 9.0 | 9.0 | 9.0 | 8.0 | 9.0 |
| 2-imidazolin-2-yl)-1H- | .250 | 8.0 | 9.0 | 3.0 | 9.0 | 7.0 | 9.0 | 8.0 | 8.0 | 8.0 | 9.0 |
| pyrrolo[3,2-b]pyridine- | .125 | 7.0 | 8.0 | 3.0 | 9.0 | 6.0 | 8.0 | 7.0 | 6.0 | 7.0 | 9.0 |
| 6-carboxylic acid | | | | | | | | | | | |
| Methyl 7,8-dihydro-2-(4- | 1.000 | 9.0 | 4.0 | 6.0 | 9.0 | 9.0 | 8.0 | 0.0 | 7.0 | 5.0 | 2.0 |
| isopropyl-4-methyl-5-oxo- | .500 | 8.0 | 4.0 | 2.0 | 9.0 | 7.0 | 7.0 | 0.0 | 4.0 | 2.0 | 1.0 |
| 2-imidazolin-2-yl)-5H- | .250 | 3.0 | 2.0 | 2.0 | 8.5 | 2.0 | 7.0 | 0.0 | 3.0 | 0.0 | 0.0 |
| pyrano-[4,3-b]pyridine- | .125 | 2.0 | 1.0 | 0.0 | 7.5 | 0.0 | 6.0 | 0.0 | 0.0 | 0.0 | 0.0 |
| 3-carboxylate | | | | | | | | | | | |
| Furfuryl 7,8-dihydro-2-(4- | 1.000 | 9.0 | 9.0 | 7.0 | 9.0 | 9.0 | 9.0 | 9.0 | 9.0 | 9.0 | 9.0 |
| isopropyl-4-methyl-5-oxo- | .500 | 9.0 | 9.0 | 7.0 | 9.0 | 9.0 | 9.0 | 6.0 | 9.0 | 8.0 | 7.0 |
| 2-imidazolin-2-yl)-5H- | .250 | 9.0 | 9.0 | 6.0 | 9.0 | 9.0 | 9.0 | 7.0 | 9.0 | 8.0 | 7.0 |
| pyrano-[4,3-b]pyridine- | .125 | 9.0 | 9.0 | 5.0 | 9.0 | 9.0 | 9.0 | 0.0 | 7.0 | 6.0 | 3.0 |

TABLE XI-continued

| Compound | RATE | Post-Emergence Tests - Rates in kg/ha BARNY ARDGR | FOX TAIL SP | P NUT SEDGE | WILD OATS | QUACK GRASS | FLD B INDWD | MATRI CARIA | MRN GLRY SP | RAG WEED | VEL-VET LEAF |
|---|---|---|---|---|---|---|---|---|---|---|---|
| 3-carboxylate | | | | | | | | | | | |
| 6-(4-Isopropyl-4-methyl-5- | 1.000 | 4.0 | 0.0 | 2.0 | 9.0 | 9.0 | 9.0 | 0.0 | 7.0 | 7.0 | 2.0 |
| oxo-2-imidazolin-2-yl)-3- | .500 | 2.0 | 0.0 | 2.0 | 8.0 | 6.0 | 8.0 | 0.0 | 5.0 | 2.0 | 1.0 |
| methoxy-1-methyl-1H- | .250 | 1.0 | 0.0 | 1.0 | 8.0 | 2.0 | 2.0 | 0.0 | 4.0 | 1.0 | 0.0 |
| pyrrolo[2,3-b]-pyridine- | .125 | 0.0 | 0.0 | 0.0 | 8.0 | 0.0 | 0.0 | 0.0 | 0.0 | 2.0 | 0.0 |
| 5-carboxylic acid | | | | | | | | | | | |
| 2,3-Dihydro-6-(4-isopropyl- | 1.000 | 9.0 | 9.0 | 9.0 | 9.0 | 6.0 | 9.0 | 9.0 | 9.0 | 6.0 | 8.0 |
| 4-methyl-5-oxo-2-imidazol- | .500 | 9.0 | 9.0 | 8.0 | 9.0 | 6.0 | 7.0 | 9.0 | 9.0 | 6.0 | 6.0 |
| in-2-yl)-1-methyl-1H- | .250 | 9.0 | 9.0 | 7.0 | 9.0 | 8.0 | 7.0 | 8.0 | 9.0 | 5.0 | 4.0 |
| pyrrolo[2,3-b]- | .125 | 9.0 | 9.0 | 7.0 | 9.0 | 7.0 | 7.0 | 2.0 | 7.0 | 1.0 | 0.0 |
| pyridine-5-carboxylic acid | | | | | | | | | | | |
| 7,8-Dihydro-2-(4-isopropyl- | 1.000 | 9.0 | 9.0 | 3.0 | 9.0 | 4.0 | 6.0 | 5.0 | 8.0 | 0.0 | 3.0 |
| 4-methyl-5-oxo-2-imidazol- | .500 | 3.0 | 4.0 | 3.0 | 6.0 | 2.0 | 4.0 | | 6.0 | 0.0 | 1.0 |
| in-2-yl)-5H-thiopyrano[4, | .250 | 0.0 | 2.0 | 2.0 | 5.0 | 1.0 | 1.0 | 2.0 | 5.0 | 0.0 | 1.0 |
| 3-b]pyridine-3- | .125 | 0.0 | 0.0 | 1.0 | 3.0 | 0.0 | 1.0 | 1.0 | 2.0 | 0.0 | 0.0 |
| carboxylic acid | | | | | | | | | | | |
| 5-(4-Isopropyl-4-methyl-5- | 1.000 | 9.0 | 9.0 | 7.0 | 9.0 | 8.0 | 9.0 | 9.0 | 9.0 | 8.0 | 9.0 |
| oxo-2-imidazolin-2-yl)-1- | .500 | 9.0 | 9.0 | 9.0 | 9.0 | 8.0 | 8.0 | 9.0 | 8.0 | 8.0 | 9.0 |
| methyl-1H-pyrrolo[3,2-b] | .250 | 9.0 | 9.0 | 8.0 | 9.0 | 8.0 | 8.0 | 9.0 | 8.0 | 9.0 | 9.0 |
| pyridine-6-carboxylic acid | .125 | 9.0 | 9.0 | 8.0 | 9.0 | 8.0 | 7.0 | 8.0 | 8.0 | 2.0 | 9.0 |
| 3,4-Dihydro-7-(4-isopropyl- | 1.000 | 9.0 | 9.0 | 9.0 | 9.0 | 9.0 | 7.0 | | 8.0 | 6.0 | 9.0 |
| 4-methyl-5-oxo-2-imi- | .500 | 9.0 | 9.0 | 6.0 | 9.0 | 8.0 | 7.0 | 5.0 | 7.0 | 3.0 | 8.0 |
| dazolin-2-yl)-2H-thio- | .250 | 9.0 | 6.0 | 4.0 | 9.0 | 8.0 | 7.0 | 2.0 | 7.0 | 1.0 | 8.0 |
| pyrano[2,3-b]-pyridine-6- | .125 | 9.0 | 4.0 | 2.0 | 8.0 | 7.0 | 6.0 | 0.0 | 5.0 | 0.0 | 2.0 |
| carboxylic acid | | | | | | | | | | | |
| 3,4-Dihydro-7-(4-isopropyl- | 1.000 | 9.0 | 9.0 | 9.0 | 9.0 | 9.0 | 8.0 | 8.0 | 9.0 | 9.0 | 9.0 |
| 4-methyl-5-oxo-2-imidazol- | .500 | 9.0 | 9.0 | 9.0 | 9.0 | 9.0 | 9.0 | 5.0 | 9.0 | 8.0 | 9.0 |
| in-2-yl)-2H-pyrano[2,3-b] | .250 | 9.0 | 9.0 | 9.0 | 9.0 | 8.0 | 9.0 | 5.0 | 8.0 | 6.0 | 9.0 |
| pyridine-6-carboxylic acid | .125 | 9.0 | 9.0 | 9.0 | 9.0 | 7.0 | 8.0 | 5.0 | 7.0 | 2.0 | 9.0 |
| 6-(4-Isopropyl-4-methyl-5- | 1.000 | 9.0 | 9.0 | 9.0 | 9.0 | 9.0 | 9.0 | | 8.0 | 9.0 | 6.0 |
| oxo-2-imidazolin-2-yl)-1- | .500 | 9.0 | 9.0 | 7.0 | 9.0 | 9.0 | 7.0 | | 8.0 | 9.0 | 6.0 |
| methyl-1H-pyrrolo[2,3-b] | .250 | 9.0 | 9.0 | 8.0 | 9.0 | 9.0 | 7.0 | | 5.0 | 6.0 | 5.0 |
| pyridine-5-carboxylic acid | .125 | 9.0 | 9.0 | 8.0 | 9.0 | 9.0 | 7.0 | 2.0 | 8.0 | 5.0 | 3.0 |
| 5-(4-Isopropyl-4-methyl-5- | 1.000 | 9.0 | 9.0 | 7.0 | 9.0 | 8.0 | 9.0 | 9.0 | 9.0 | 8.0 | 9.0 |
| oxo-2-imidazolin-2-yl)-1- | .500 | 9.0 | 9.0 | 7.0 | 9.0 | 9.0 | 9.0 | 7.0 | 9.0 | 8.0 | 9.0 |
| methoxy-2-methyl-1H- | .250 | 9.0 | 9.0 | 5.0 | 9.0 | 9.0 | 9.0 | | 9.0 | 7.0 | 9.0 |
| pyrrolo-[3,2-b]pyridine-6- | .125 | 9.0 | 9.0 | 4.0 | 9.0 | 6.0 | 8.0 | | 9.0 | 6.0 | 9.0 |
| carboxylic acid | | | | | | | | | | | |

EXAMPLE 102

Preemergence Herbicidal Evaluation of Test Compounds

The preemergence herbicidal activity of the compounds of the present invention is exemplified by the following tests in which the seeds of a variety of monocotyledonous and dicotyledonous plants are separately mixed with potting soil and planted on top of approximately one inch of soil in separate pint cups. After planting, the cups are sprayed with the selected aqueous acetone solution containing test compound in sufficient quantity to provide the equivalent of about 0.016 to 10 kg per hectare of test compound per cup. The treated cups are then placed on greenhouse benches, watered and cared for in accordance with conventional greenhouse procedures. From four to five weeks after treatment, the tests are terminated and each cup is examined and rated according to the rating system set forth above. The herbicidal proficiency of the active ingredients of the present invention is evident from the test results which are recorded in Table XII below. Where more than one test is involved for a given compound, the data are averaged.

TABLE XII

| Compound | RATE | Pre-Emergence Tests - Rates in kg/ha BARNY ARDGR | FOX TAIL SP | P NUT SEDGE | WILD OATS | QUACK GRASS | FLD B INDWD | MATRI CARIA | MRN GLRY SP | RAG WEED | VEL-VET LEAF |
|---|---|---|---|---|---|---|---|---|---|---|---|
| 6-(4-Isopropyl-4-methyl-5- | .500 | 4.0 | 9.0 | 9.0 | 8.0 | 9.0 | 9.0 | 9.0 | 8.0 | 8.0 | 8.0 |
| oxo-2-imidazolin-2-yl)- | .250 | 2.0 | 6.0 | 6.0 | 4.0 | 6.0 | 6.0 | 8.0 | | 6.0 | 8.0 |
| 3-methyl-isoxazolo[5, | .125 | 0.0 | 2.0 | 4.0 | 0.0 | 0.0 | 1.0 | 0.0 | 3.0 | 5.0 | 6.0 |
| 4-b]pyridine-5- | | | | | | | | | | | |
| carboxylic acid | | | | | | | | | | | |
| 6-(4-Isopropyl-4-methyl-5- | .500 | 7.0 | 7.0 | 7.0 | 7.0 | 9.0 | 9.0 | 0.0 | 3.0 | 0.0 | 5.0 |
| oxo-2-imidazolin-2-yl)-1H- | .250 | 5.0 | 4.0 | 5.0 | 5.0 | 7.0 | 9.0 | 0.0 | 1.0 | 0.0 | 2.0 |
| pyrazolo[3,4-b]pyridine- | .125 | 1.0 | 1.0 | 3.0 | 3.0 | 3.0 | 9.0 | 0.0 | 0.0 | 0.0 | 1.0 |

TABLE XII-continued

| Compound | RATE | Pre-Emergence Tests - Rates in kg/ha BARNY ARDGR | FOX TAIL SP | P NUT SEDGE | WILD OATS | QUACK GRASS | FLD B INDWD | MATRI CARIA | MRN GLRY SP | RAG WEED | VEL-VET LEAF |
|---|---|---|---|---|---|---|---|---|---|---|---|
| 5-carboxylic acid | | | | | | | | | | | |
| 6-(4-Isopropyl-4-methyl-5-oxo-2-imidazolin-2-yl)-1-methyl-1H-pyrazolo[3,4-b]-pyridine-5-carboxylic acid | .500 | 9.0 | 9.0 | 9.0 | 9.0 | 9.0 | 9.0 | 2.0 | 9.0 | 7.0 | 4.0 |
| | .250 | 8.0 | 9.0 | 9.0 | 8.0 | 9.0 | 9.0 | 0.0 | 9.0 | 0.0 | 4.0 |
| | .125 | 5.0 | 9.0 | 9.0 | 9.0 | 9.0 | 9.0 | 0.0 | 9.0 | 0.0 | 4.0 |
| 6-(4-Isopropyl-4-methyl-5-oxo-2-imidazolin-2-yl)-2-methyl-2H-pyrazolo[3,4-b]-pyridine-5-carboxylic acid | .500 | 0.0 | 4.0 | 9.0 | 0.0 | 9.0 | 9.0 | 4.0 | 8.0 | 6.0 | 6.0 |
| | .250 | 0.0 | 0.0 | 9.0 | 0.0 | 9.0 | 7.0 | 1.0 | 4.0 | 2.0 | 5.0 |
| | .125 | 0.0 | 0.0 | 9.0 | 0.0 | 9.0 | 4.0 | 0.0 | 0.0 | 1.0 | 2.0 |
| 5-(4-Isopropyl-4-methyl-5-oxo-2-imidazolin-2-yl)-1-methoxy-1H-pyrrolo[3,2-b]pyridine-6-carboxylic acid | .500 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 8.0 | 9.0 | 9.0 | 9.0 |
| | .125 | 9.0 | 9.0 | 9.0 | 9.0 | 9.0 | 9.0 | 8.0 | 9.0 | 8.0 | 9.0 |
| 7,8-Dihydro-2-(4-isopropyl-4-methyl-5-oxo-2-imidazol-in-2-yl)-5H-pyrano[4,3-b]pyridine-3-carboxylic acid | 8.000 | 9.0 | | 9.0 | 9.0 | 9.0 | 9.0 | | 8.0 | 9.0 | 9.0 |
| | .500 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 7.0 | 9.0 | 9.0 | 9.0 |
| | .125 | 9.0 | 8.0 | 9.0 | 9.0 | 9.0 | 9.0 | 4.0 | 9.0 | 9.0 | 8.0 |
| 1-(Allyloxy)-5-(4-isopropyl-4-methyl-5-oxo-2-imidazolin-2-yl)-1H-pyrrolo[3,2-b]-pyridine-6-carboxylic acid | .500 | 9.0 | 9.0 | 9.0 | 9.0 | 9.0 | 9.0 | 9.0 | 9.0 | 9.0 | 9.0 |
| | .250 | 9.0 | 9.0 | 8.0 | 9.0 | 9.0 | 9.0 | 9.0 | 9.0 | 8.0 | 9.0 |
| | .125 | 9.0 | 9.0 | 9.0 | 9.0 | 9.0 | 8.0 | 9.0 | 9.0 | 8.0 | 9.0 |
| Methyl 7,8-dihydro-2-(4-isopropyl-4-methyl-5-oxo-2-imidazolin-2-yl)-5H-pyrano-[4,3-b]pyridine-3-carboxylate | .500 | 6.0 | 9.0 | 9.0 | 9.0 | 9.0 | 9.0 | 5.0 | 8.0 | 6.0 | 7.0 |
| | .250 | 2.0 | 7.0 | 7.0 | 9.0 | 9.0 | 8.0 | 1.0 | 4.0 | 2.0 | 5.0 |
| | .125 | 0.0 | 6.0 | 6.0 | 9.0 | 3.0 | 8.0 | 0.0 | 1.0 | 0.0 | 2.0 |
| Furfuryl 7,8-dihydro-2-(4-iso-propyl-4-methyl-5-oxo--2-imidazolin-2-yl)-5H-pyrano[4,3-b]-pyridine-3-carboxylate | .500 | 9.0 | 9.0 | 9.0 | 9.0 | 9.0 | 9.0 | 9.0 | 9.0 | 9.0 | 8.0 |
| | .250 | 9.0 | 9.0 | 9.0 | 9.0 | 9.0 | 9.0 | 9.0 | 9.0 | 9.0 | 9.0 |
| | .125 | 4.0 | 9.0 | 9.0 | 9.0 | 9.0 | 9.0 | 4.0 | 8.0 | 5.0 | 7.0 |
| 6-(4-isopropyl-4-methyl-5-oxo-2-imidazolin-2-yl)-3-methoxy-1-methyl-1H-pyrrolo[2,3-b]-pyridine-5-carboxylic acid | .500 | 4.0 | 0.0 | 6.0 | 9.0 | 8.0 | 7.0 | 2.0 | 8.0 | 8.0 | 7.0 |
| | .250 | 1.0 | 0.0 | 2.0 | 4.0 | 6.0 | 4.0 | | 8.0 | 2.0 | 2.0 |
| 2,3-Dihydro-6-(4-isopropyl-4-methyl-5-oxo-2-imidazolin-2-yl)-1-methyl-1H-pyrrolo-[2,3-b] pyridine-5-carboxylic acid | .500 | 9.0 | 9.0 | 9.0 | 9.0 | 9.0 | 9.0 | 7.0 | 9.0 | 7.0 | 7.0 |
| | .250 | 8.0 | 9.0 | 9.0 | 9.0 | 9.0 | 9.0 | 7.0 | 9.0 | 7.0 | 7.0 |
| | .125 | 6.0 | 9.0 | 9.0 | 9.0 | 9.0 | 4.0 | 6.0 | 8.0 | 4.0 | 6.0 |
| 3-(m-chlorophenyl)-7-(4-isopropyl-4-methyl-5-oxo-2-imidazolin-2-yl)-4-methyl-2-oxo-2H-pyrano[2,3-b]-pyridine-6-carboxylic acid | .500 | 2.0 | 6.0 | 0.0 | 8.5 | 1.0 | 0.0 | 0.0 | 0.0 | 0.0 | 1.0 |
| | .250 | 0.5 | 2.0 | 0.0 | 8.0 | 1.0 | 0.0 | 0.0 | 0.0 | 0.0 | 1.0 |
| | .125 | 0.0 | 0.0 | 0.0 | 7.5 | 0.5 | 0.0 | 0.0 | 0.0 | 0.0 | 0.5 |
| 3-(p-chlorophenyl-7-(4-iso-propyl-4-methyl-5-oxo-2-imidazolin-2-yl)-4-methyl-2-oxo-2H-pyrano[2,3-b]-pyridine-6-carboxylic acid | 4.000 | 6.0 | | 0.0 | 8.0 | 9.0 | 0.0 | | 4.0 | 7.0 | 6.0 |
| | .500 | 5.0 | 7.0 | 0.0 | 9.0 | 4.0 | 0.0 | 0.0 | 0.0 | 2.0 | 0.0 |
| | .250 | 0.0 | 1.0 | 0.0 | 9.0 | 1.0 | 0.0 | 0.0 | 0.0 | 0.0 | 0.0 |
| | .125 | 0.0 | 0.0 | 0.0 | 8.0 | 0.0 | 0.0 | 0.0 | 0.0 | 0.0 | 0.0 |
| 5-(4-isopropyl-4-methyl-5-oxo-2-imidazolin-2-yl)-1-methyl-1H-pyrrolo[3,2-b]-pyridine-6-carboxylic acid | .500 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 8.0 | 9.0 | 9.0 |
| | .125 | 9.0 | 9.0 | 9.0 | 9.0 | 9.0 | 9.0 | 8.0 | 4.0 | 8.0 | 9.0 |
| 3,4-Dihydro-7-(4-isopropyl-4-methyl-5-oxo-2-imidazolin-2-yl)-2H-thiopyrano[2,3-b]-pyridine-6-carboxylic acid | .500 | 2.0 | 4.0 | 6.0 | 8.0 | 6.0 | 2.0 | 0.0 | 5.0 | 6.0 | 6.0 |
| | .250 | 1.0 | 0.0 | 3.0 | 3.0 | 2.0 | 2.0 | 0.0 | 2.0 | 4.0 | 4.0 |
| | .125 | 0.0 | 0.0 | 0.0 | 1.0 | 0.0 | 1.0 | 0.0 | 0.0 | 2.0 | 2.0 |
| 3,4-Dihydro-7-(4-isopropyl-4-methyl-5-oxo-2-imidazolin-2-yl)-2H-pyrano[2,3-b]-pyri-dine-6-carboxylic acid | .500 | 9.0 | 9.0 | 9.0 | 9.0 | 9.0 | 9.0 | 4.0 | 9.0 | 8.0 | 8.0 |
| | .250 | 9.0 | 9.0 | 9.0 | 9.0 | 9.0 | 9.0 | 4.0 | 8.0 | 6.0 | 7.0 |
| | .125 | 4.0 | 9.0 | 8.0 | 9.0 | 9.0 | 8.0 | 2.0 | 6.0 | 2.0 | 5.0 |
| 6-(4-Isopropyl-4-methyl-5-oxo-2-imidazolin-2-yl)-1- | .500 | 9.0 | 9.0 | 9.0 | 9.0 | 9.0 | 9.0 | 9.0 | 9.0 | 9.0 | 8.0 |
| | .250 | 9.0 | 9.0 | 7.0 | 9.0 | 9.0 | 9.0 | 6.0 | 9.0 | 9.0 | 8.0 |

TABLE XII-continued

| | | Pre-Emergence Tests - Rates in kg/ha | | | | | | | | | |
|---|---|---|---|---|---|---|---|---|---|---|---|
| Compound | RATE | BARNY ARDGR | FOX TAIL SP | P NUT SEDGE | WILD OATS | QUACK GRASS | FLD B INDWD | MATRI CARIA | MRN GLRY SP | RAG WEED | VEL-VET LEAF |
| methyl-1H-pyrrolo[2,3-b]-pyridine-5-carboxylic acid | .125 | 7.0 | 9.0 | 8.0 | 9.0 | 9.0 | 7.0 | 2.0 | 9.0 | 9.0 | 6.0 |
| 5-(4-Isopropyl-4-methyl-5-oxo-2-imidazolin-2-yl)-1-methoxy-2-methyl-1H-pyrrolo-[3,2-b]pyridine-6-carboxylic acid | .500 | 9.0 | 9.0 | 8.0 | 9.0 | 9.0 | 9.0 | 8.0 | 9.0 | 8.0 | 9.0 |
| | .250 | 9.0 | 9.0 | 8.0 | 9.0 | 9.0 | 9.0 | 8.0 | 9.0 | 6.0 | 9.0 |
| | .125 | 9.0 | 9.0 | 7.0 | 9.0 | 9.0 | 7.0 | 8.0 | 9.0 | 6.0 | 9.0 |
| 2-(4-Isopropyl-4-methyl-5-oxo-2-imidazolin-2-yl)-1,8-naphthyridine-3-carboxylic acid | .500 | 0.0 | 2.0 | 9.0 | 6.0 | 9.0 | 9.0 | 0.0 | 8.0 | | 6.0 |
| | .250 | 0.0 | 0.0 | 9.0 | 4.0 | 9.0 | 9.0 | 0.0 | 8.0 | 0.0 | 3.0 |
| | .125 | 0.0 | 0.0 | 6.0 | 2.0 | 8.0 | 4.0 | 0.0 | 0.0 | 0.0 | 2.0 |

What is claimed is:

1. (2-Imidazolin-2-yl) fused heteropyridine compounds having the structure

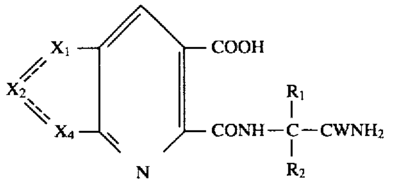

(XXII)

or

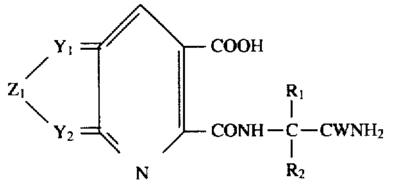

(XXIV)

wherein $R_1$ is $C_1$-$C_4$ alkyl;

$R_2$ is $C_1$-$C_4$ alkyl or $C_3$-$C_6$ cycloalkyl;

and when taken together with the carbon to which they are attached, $R_1$ and $R_2$ may represent $C_3$-$C_6$ cycloalkyl, optionally substituted with methyl;

--- represents a single or double bond;

W is O or S;

$X_1$, $X_2$, and $X_4$ are any combination of from zero to three $CR_4$ or $CR_5$; from zero to three N or $NR_3$ and from zero to two O or S;

$Y_1$ and $Y_2$ are N or $CR_4$ and are the same or different;

$Z_1$ is O, S $NR_3$ or $CR_5R_6$ with the proviso that at least one of $X_{1-4}$, $Y_{1-2}$ or $Z_1$ is a heteroatom;

$R_3$ is $C_1$-$C_4$ alkyl, which may be optionally substituted with phenyl or one or more halogens; $C_3$-$C_6$ alkenyl, optionally substituted with phenyl or one or more halogens; $C_3$-$C_6$ alkynyl, optionally substituted with phenyl or halogen; $C_1$-$C_4$ alkoxy, optionally substituted with phenyl or one or more halogens; $C_3$-$C_6$ alkenyloxy optionally substituted with phenyl or one or more halogens; $C_3$-$C_6$ alkynyloxy optionally substituted with halogen or phenyl; or $C_2$-$C_6$ alkanoyloxy, optionally substituted with halogen or phenyl;

$R_4$ is hydrogen, halogen, $C_1$-$C_6$ alkyl; $C_1$-$C_4$ alkoxy; $C_2$-$C_6$ alkanoyloxy; $C_1$-$C_4$ alkylthio; phenoxy; $C_1$-$C_4$ haloalkyl, $C_1$-$C_4$ haloalkoxy; nitro, $C_1$-$C_4$ alkoxycarbonyl; $C_1$-$C_4$ dialkylamino; $C_1$-$C_4$ alkyl-sulfonyl or phenyl, optionally substituted with one or two $C_1$-$C_4$ alkyl, $C_1$-$C_4$ alkoxy, halogen or $C_1$-$C_4$ haloalkyl;

$R_5$ $R_6$ are each hydrogen, $C_1$-$C_4$ alkyl; $C_1$-$C_4$ alkoxy, $C_1$-$C_4$ haloalkoxy, nitro, $C_1$-$C_4$ alkylsulfonyl or phenyl optionally substituted with one or two $C_1$-$C_4$ alkyl, $C_1$-$C_4$ alkoxy, halogen or $C_1$-$C_4$ haloalkyl; or any combination of these groups except when $R_5$ and $R_6$ are the same group, they are either both hydrogen or both $C_1$-$C_4$ alkyl; and when taken together, $R_5$ and $R_6$ may form a ring in which $R_5R_6$ are represented by the structure $-(CH_2)_n-$ where n is an integer of 4 or 5, or when taken together, $R_5$ and $R_6$ may form a group =O or $=NR_7$ wherein $R_7$ is phenyl, $C_1$-$C_4$ alkyl, $C_1$-$C_4$ alkoxy, $C_1$-$C_4$ alkylamino;

$R_3$, $R_4$, $R_5$ and $R_6$, when present on adjacent positions may, along with the atoms to which they are attached, form a ring and such $R_3$-$R_6$ pairs can be represented by the structure $-(CH_2)_m-$ or $-(CH)_m-$ where m is an integer of 3 or 4;

with the provisos that in structure XXII when $X_1$ is O or S at least one of $X_2$ and $X_4$ may not be $CR_4$ or $CR_5R_6$; when $X_4$ is O or S, at least one of $X_1$ and $X_2$ may not be $CR_4$ or $CR_5R_6$; in structure XXIV when $Z_1$ is O, $Y_1$ and $Y_2$ may not be $CR_4$;

--- represents a single bond between:

$X_1$ and $X_2$ when either $X_1$ or $X_2$ is S, O, $NR_3$ or $CR_5R_6$; and $X_2$ and $X_6$ in structure XXII, when either $X_2$ or $X_4$ is S, O, $NR_3$ or $CR_5R_6$; and when one of $X_{1-4}$ is oxygen, the $X_{1-4}$ to which it is attached is N, $NR_3$, $CR_4$ or or $CR_5R_6$.

2. The claim 1 wherein $R_1$ is methyl or ethyl, $R_2$ is ethyl, propyl, iso-propyl and when $R_1$ and $R_2$ are taken together, they represent a cyclohexyl ring, optionally substituted with methyl;

$R_3$ is $C_1$-$C_3$ alkyl, $C_1$-$C_4$ alkoxy, allyloxy, $CF_3O-$, $CF_2HO-$ or $CF_3$.

3. The compound according to claim 2, wherein $R_1$ is methyl and $R_2$ is isopropyl;

$R_3$ is methyl, ethyl, methoxy, ethoxy and allyloxy;

$R_4$, $R_5$; and $R_6$ are each methyl, ethyl, hydrogen, methoxy and ethoxy, or $R_5R_6$, when taken together are=0.

4. The compound according to claim 3 having structural formula XXII wherein $R_1$ is methyl, $R_2$ is isopropyl; $R_3$is methyl, $R_4$ is hydrogen; W is O; $X_1$ and $X_2$ are $CR_4$ and $X_4$ is $NR_3$.

* * * * *